US012660992B2

(12) United States Patent
Kitamura et al.

(10) Patent No.: US 12,660,992 B2
(45) Date of Patent: Jun. 23, 2026

(54) ENDOSCOPE AND OPERATION SECTION FOR ENDOSCOPE

(71) Applicant: OLYMPUS MEDICAL SYSTEMS CORP., Tokyo (JP)

(72) Inventors: Ojiro Kitamura, Hachioji (JP); Takeo Suzuki, Hachioji (JP); Hidenosuke Hase, Hachioji (JP); Hideo Sanai, Hachioji (JP); Masahiro Ashizuka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 188 days.

(21) Appl. No.: 18/443,713

(22) Filed: Feb. 16, 2024

(65) Prior Publication Data

US 2024/0277215 A1     Aug. 22, 2024

Related U.S. Application Data

(60) Provisional application No. 63/446,383, filed on Feb. 17, 2023.

(51) Int. Cl.
A61B 1/005 (2006.01)
A61B 1/00 (2006.01)

(52) U.S. Cl.
CPC ........ A61B 1/0052 (2013.01); A61B 1/00103 (2013.01); A61B 1/0057 (2013.01)

(58) Field of Classification Search
CPC .. A61B 1/00103; A61B 1/0052; A61B 1/0057
See application file for complete search history.

(56) References Cited

U.S. PATENT DOCUMENTS

| | | | |
|---|---|---|---|
| 5,993,381 A | * | 11/1999 | Ito ...................... A61B 1/00188 600/146 |
| 2007/0282371 A1 | * | 12/2007 | Lee ........................ A61B 17/29 606/205 |
| 2012/0302829 A1 | * | 11/2012 | Omoto ................... A61B 1/015 600/109 |

(Continued)

FOREIGN PATENT DOCUMENTS

| | | |
|---|---|---|
| JP | H10-314108 A | 12/1998 |
| JP | 2000-254092 A | 9/2000 |

(Continued)

*Primary Examiner* — Aaron B Fairchild
(74) *Attorney, Agent, or Firm* — Morgan, Lewis & Bockius LLP

(57) ABSTRACT

An endoscope includes: an insertion section including a distal end and a proximal end, the insertion section configured for insertion into a subject; an operation section main body connected to the proximal end of the insertion section and, the operation section main body configured to be grasped by a user. The operation section main body includes an operation knob and a switch button. The operation knob is rotatable about a center axis to move the distal end of the insertion section. The switch button is translatable in a translating direction. In a view in a longitudinal direction of the operation section main body, the center axis of the operation knob is configured to be tilted with respect to a direction that is perpendicular to each of the longitudinal direction of the operation section main body and the translating direction of the switch button.

20 Claims, 40 Drawing Sheets

(56)  References Cited

U.S. PATENT DOCUMENTS

| | | |
|---|---|---|
| 2015/0094655 A1 | 4/2015 | Fukuda et al. |
| 2017/0127913 A1 | 5/2017 | Hoshino et al. |
| 2019/0387962 A1 | 12/2019 | Nakamitsu et al. |

FOREIGN PATENT DOCUMENTS

| | | |
|---|---|---|
| JP | 2005-245545 A | 9/2005 |
| JP | 2009-165674 A | 7/2009 |
| JP | 2012-187265 A | 10/2012 |
| WO | 2014/136470 A1 | 9/2014 |
| WO | 2016/121529 A1 | 8/2016 |
| WO | 2018/135041 A1 | 7/2018 |

* cited by examiner

FIG. 55

| INCLINATION ANGLE | HUMAN SUBJECT A | HUMAN SUBJECT B | HUMAN SUBJECT C | HUMAN SUBJECT D | HUMAN SUBJECT E | HUMAN SUBJECT F | HUMAN SUBJECT G | HUMAN SUBJECT H | HUMAN SUBJECT I | HUMAN SUBJECT J |
|---|---|---|---|---|---|---|---|---|---|---|
| 1~3° | B | B | B | B | B | B | B | B | B | B |
| 4° | B | B | B | B | B | B | B | B | B | B |
| 4.5° | B | B | G | B | B | B | B | B | B | B |
| 5° | B | B | G | B | G | G | B | B | B | B |
| 5.5° | B | G | G | B | G | G | B | G | G | G |
| 6° | B | G | G | G | G | G | G | G | G | G |
| 6.5° | G | EXC | EXC | EXC | EXC | EXC | EXC | EXC | EXC | EXC |
| 7° | G | EXC | EXC | EXC | EXC | EXC | EXC | EXC | EXC | EXC |
| 7.5° | EXC | EXC | EXC | EXC | G | EXC | G | EXC | G | EXC |
| 8° | EXC | G | G | EXC | G | G | EXC | G | EXC | EXC |
| 8.5° | G | B | G | G | B | G | G | G | EXC | EXC |
| 9° | G | B | G | G | B | B | G | G | G | G |
| 9.5° | B | B | B | G | B | B | B | G | G | G |
| 10° | B | B | B | B | B | B | B | G | B | B |
| 10.5° | B | B | B | B | B | B | B | B | B | B |
| 11° | B | B | B | B | B | B | B | B | B | B |
| 12~30° | B | B | B | B | B | B | B | B | B | B | legend
B not good
G good
EXC excellent

ENDOSCOPE AND OPERATION SECTION FOR ENDOSCOPE

RELATED APPLICATION DATA

This application is based on and claims priority under 35 U.S.C. § 119 to U.S. Provisional Application No. U.S. 63/446,383, filed on Feb. 17, 2023, the entire contents of which are incorporated herein by reference.

FIELD OF DISCLOSURE

The present disclosure is a disclosure related to an endoscope including a bending operation mechanism that realizes a bending operation of a bending section by operating a bending operation member provided in an operation section main body and to the operation section of the endoscope.

BACKGROUND

In the related art, endoscopes have widely been used in the medical field, the industrial field, and the like. Typically, an endoscope is configured to include an insertion section that has flexibility and is formed into an elongated tube shape and an operation section that is provided continuously from a proximal end of the insertion section and includes various operation members and the like on an outer surface. In such a case, a bending section that is formed to be freely bent is provided in a partial region of the insertion section near a distal end.

The bending section is provided near the distal end of the insertion section and has a configuration to receive an operation input from a predetermined operation member (referred to as a bending operation member or a bending operation knob) provided in the operation section main body and realize active bending in four directions, namely upward, downward, leftward, and rightward around a long axis of the insertion section. Therefore, the endoscope in the related art includes, inside the operation section main body, a bending operation mechanism that operates in conjunction with the bending operation member.

Here, the bending operation member typically includes a plurality of independent operation members in order to perform bending operations in four directions, namely upward, downward, leftward, and rightward, for example. Specifically, the bending operation member is typically configured to include two independent bending operation members, namely a bending operation member that performs a bending operation in up-down (UD) direction) and an operating member that performs a bending operation in a left-right (LR) direction, for example.

Various endoscopes in such a form have been proposed by, for example, Japanese Patent Application Laid Open Publication No. 2012-187265, Japanese Patent Application Laid Open Publication No. 2000-254092, and the like and have generally been put into practical use.

SUMMARY

An endoscope includes: an insertion section including a distal end and a proximal end, the insertion section configured for insertion into a subject; an operation section main body connected to the proximal end of the insertion section and, the operation section main body configured to be grasped by a user. The operation section main body includes an operation knob and a switch button. The operation knob is rotatable about a center axis to move the distal end of the insertion section. The switch button is translatable in a translating direction. In a view in a longitudinal direction of the operation section main body, the center axis of the operation knob is configured to be tilted with respect to a direction that is perpendicular to each of the longitudinal direction of the operation section main body and the translating direction of the switch button.

An endoscope according to another aspect of the present disclosure includes: an operation section main body configured to be grasped by a user. The operation section main body includes an operation knob and a switch button. The operation knob is rotatable about a center axis. The switch button is translatable in a translating direction. In a view in a longitudinal direction of the operation section main body, the center axis of the operation knob is configured to be tilted with respect to a direction that is perpendicular to each of the longitudinal direction of the operation section main body and the translating direction of the switch button.

BRIEF DESCRIPTION OF THE DRAWINGS

FIG. 55 is a diagram illustrating results of inspecting relationships between inclination angles of the bending operation knob of the endoscope and operability.

DETAILED DESCRIPTION

Figure 1:
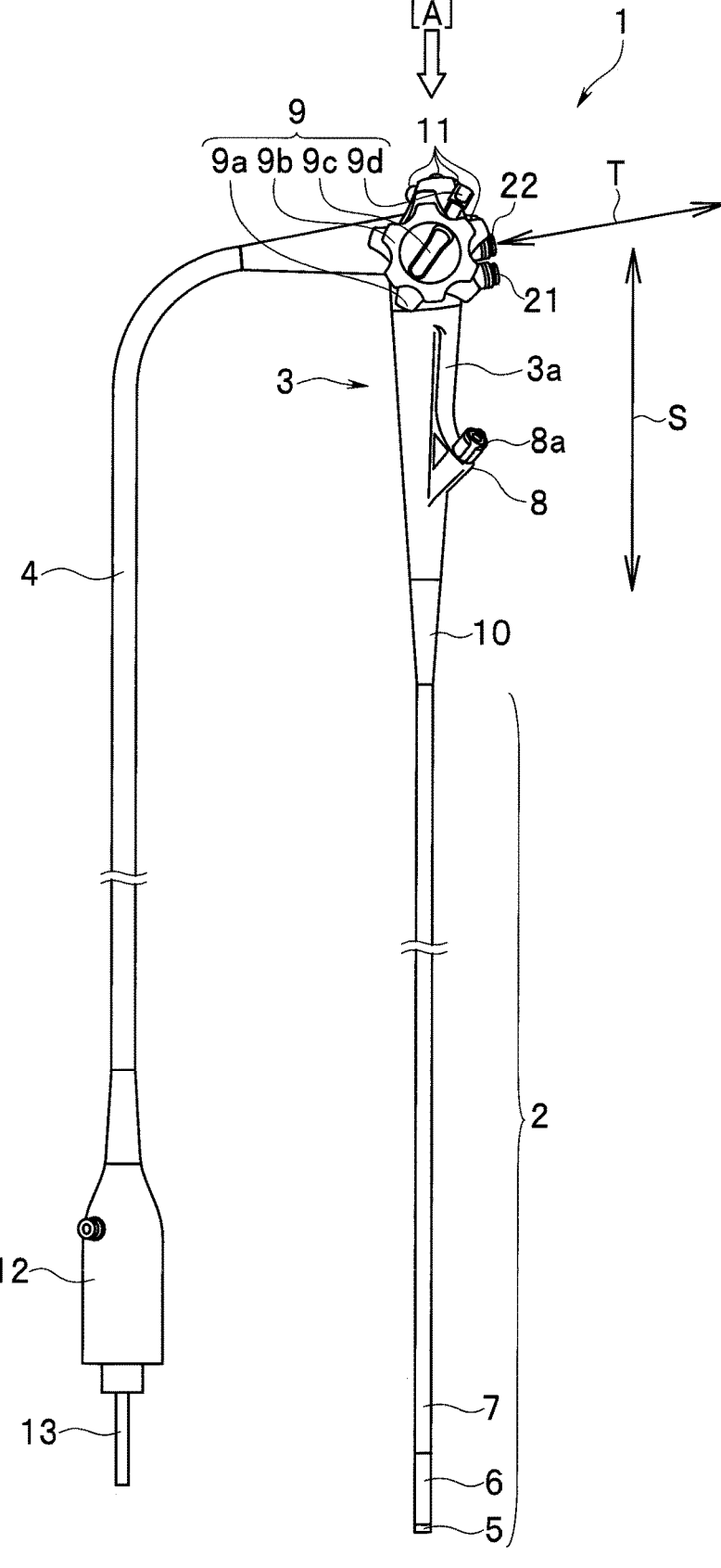
FIG. 1 is a schematic configuration example of an endoscope to which the present disclosure is applied.

Typically, a user performs operations of various operation members including a bending operation member provided in an operation section by using left-hand fingers while grasping the operation section with a left hand, for example, when the user uses an endoscope in the form in the related art as disclosed in Japanese Patent Application Laid Open Publication No. 2012-187265, Japanese Patent Application Laid Open Publication No. 2000-254092, or the like described above.

At the same time, the user performs an operation of inserting an insertion section into a body cavity of a subject by using a right hand, a fine adjustment operation related to a position, an orientation, and the like of the insertion section after the insertion into the body cavity, and the like. In such a case, there is a trend that the user performs an operation on the bending operation member mainly by using only a thumb of the left hand.

As described above, if a bending operation in an up-down direction and a bending operation in a right-left direction are continuously performed for a long time period mainly by using only the thumb of the left hand, the endoscope configured by the bending operation member including the plurality of independent operation members may lead to pain, fatigue, and the like of fingers, which may inhibit operability. Also, in a case where a plurality of bending operation members is operated by using only one finger (thumb), it is difficult to perform operations in different directions at the same time.

Thus, if left-hand fingers other than the thumb (for example, a middle finger, a ring finger, and the like) can also be used for the bending operations, for example, it is possible to expect an improvement in operation efficiency.

However, fingers of a user with a small size of hands or with short fingers other than the thumb may not reach the operation members depending on the size (outer circumferential length) of the grasped part of the operation section of the endoscope in the related art. In such a case, it is difficult to perform operations on the operation members by using the fingers other than the thumb.

On the other hand, in a case where a plurality of bending operation members are operated in different directions at the same time, in a case where a bending operation member and another operation member are operated at the same time, and the like, some user may temporarily release the right hand holding the insertion section and perform an operation on the operation member with the right hand, for example.

In such a case, the insertion section is placed on a surgical table or the like or is temporarily held by a person who is different from the user, such as an assistant, which may lead to a difficulty in fine adjustment of the insertion section. At the same time, problems that the endoscope is operated by a plurality of persons and the operation itself becomes complicated may occur.

According to the present disclosure described below, an endoscope including a bending operation mechanism that realizes a bending operation of a bending section provided near a distal end of an insertion section by operating a bending operation member provided in an operation section main body provides a configuration capable of realizing an improvement in operability, and it is thus possible to provide an endoscope and an operation section for an endoscope capable of contributing to shortening of procedure time period by using the endoscope and contributing to reduction of invasiveness in a subject (patient).

Hereinafter, the present disclosure will be described on the basis of illustrated embodiments. Each drawing used for the following description is schematically illustrated. In each of the drawings, each component is thus illustrated with a recognizable size in the drawing. Therefore, dimensional relationships of the respective members, scales, and the like in the drawings may be differently illustrated for each component. The present disclosure is not limited only to the illustrated forms in regard to the number or amount, each shape, a ratio of each size, each relative positional relationship, and the like of each component described in each drawing.

First, a schematic configuration for an endoscope to which the present disclosure is applied will be briefly described below by using FIG. 1. FIG. 1 is a schematic configuration example illustrating a schematic configuration of the endoscope to which the present disclosure is applied.

As an example of the endoscope to which the present disclosure is applied, a gastrointestinal endoscope which mainly assumes inside of organs in a gastrointestinal system as a target of observation and treatment will be described as an example.

As illustrated in FIG. 1, a configuration of an endoscope 1 to which the present disclosure is applied is basically same as a configuration of a gastrointestinal endoscope in the related art. Also, the following description will be given on the assumption that the endoscope 1 to which the present disclosure is applied is a so-called single-use endoscope in a form in which the endoscope is discarded after a single use, for example.

The endoscope 1 is configured to include an insertion section 2, an operation section 3, a universal cable 4, and the like.

The insertion section 2 is a long member that is inserted into a body cavity of a subject such as a living body from a side of a distal end. The insertion section 2 has a form in which a distal end section 5, a bending section 6, and a flexible tube section 7 are continuously connected in the order from the side of the distal end. The insertion section 2 is formed into a substantially elongated tube shape as a whole. The insertion section 2 includes a distal end and a proximal end, the insertion section is configured for insertion into the subject.

The distal end section 5 is located at the distal end of the insertion section 2. Various configuration members (not illustrated) such as an image pickup unit, an illumination unit, and the like are provided inside the distal end section 5.

Here, the image pickup unit is an electronic device unit including a photoelectric conversion element that acquires image information (stationary images and movies) of an observation target (for example, a body cavity inner wall of an organ or the like) inside the body cavity of the subject, an optical lens, and the like.

The illumination unit is a configuration unit including an optical element that emits a light beam guided from a light source device (not illustrated), which will be described later, forward from a distal end surface of the distal end section 5 and illuminates an observation target region including an affected site or the like inside the body cavity of the subject and the like.

The bending section 6 is continuously connected to a proximal end of the distal end section 5. The bending section 6 is configured to be actively bendable due to an action of the bending operation mechanism including a bending operation member, which will be described later. In such a case, the bending section 6 is configured to be continuously bendable in four directions, namely upward, downward, leftward, and rightward around a long axis of the insertion section 2. In other words, the bending section 6 is provided on the side of the distal end of the insertion section 2 and is bent in a direction intersecting a longitudinal direction of the insertion section 2.

The flexible tube section 7 is continuously connected to the proximal end of the bending section 6. The flexible tube section 7 is connected to extend from a distal end of the operation section 3. In other words, the operation section 3 is connected to a proximal end of the flexible tube section 7 of the insertion section 2. The operation section 3 is configured to include a treatment instrument insertion port 8, a bending operation knob (operation knob) 9 that is a bending operation member, a bend preventing portion 10, a plurality of operation members 11, an air feeding/water feeding button (switch button) 21, a suction button (switch button) 22, and the like.

The operation section 3 has a substantially box shape as a whole and includes an operation section main body 3a configuring a grasping section that a user of the endoscope 1 grasps with fingers. The operation section main body 3a is a configuration member that is provided continuously from a side of a proximal end of the insertion section 2 and is gripped by the user. The insertion section 2 is connected to extend from the operation section main body 3a of the operation section 3 in one direction as described above. Here, the part where the operation section 3 and the insertion section 2 are connected is provided with the bend preventing portion 10 which is a connection member. Note that a direction indicated by an arrow S in FIG. 1 will be referred to as a longitudinal direction of the operation section main body 3a. The operation section main body 3a is connected to the proximal end of the insertion section 2 and, the operation section main body 3a is configured to be grasped by the user. The operation section main body 3a includes the operation knob 9 and a switch button 21 or 22. The connection member 10 is configured to connect a distal end of the operation section main body 3a to a proximal end of the insertion section 2 having a distal end configured for insertion into the subject.

The treatment instrument insertion port 8 is provided at a predetermined position near the distal end of the operation section 3. The treatment instrument insertion port 8 is a proximal end-side opening section that communicates with a treatment instrument insertion channel (not illustrated) of the insertion section 2. The treatment instrument insertion channel is connected, on the side of the distal end, to a distal end opening (not illustrated) of the distal end section 5. Such a configuration can cause a distal end of a treatment instrument (not illustrated) inserted from the treatment instrument insertion port 8 to project outward from the distal end opening of the distal end section 5. The treatment instrument insertion port 8 is provided with a forceps cap 8a that is a forceps pipe sleeve.

The bending operation knob 9, the plurality of operation members 11, the air feeding/water feeding button 21, and the suction button 22 are provided at predetermined positions on an outer surface of the operation section main body 3a, respectively.

Among the components, the bending operation knob 9 is a configuration member that is disposed in the operation section main body 3a to be rotatable about a predetermined rotation shaft and performs an operation of moving the side of the distal end of the insertion section 2. In such a case, the bending operation knob 9 is a rotation-type operation member that rotates about a center axis Ax (see FIGS. 2 and 3, which will be described later). The bending operation knob 9 is configured by three rotation-type operation members (9a, 9b, and 9c) and one lever-type operation member (lever) (9d) although details will be described later. The operation knob 9 is rotatable about the center axis Ax to move the distal end of the insertion section 2. The operation section can include the lever 9d provided between the operation knob 9 and the operation section main body 3a, the lever 9d is configured to operate the insertion section 2.

The air feeding/water feeding button 21 and the suction button 22 are switch buttons that are provided in the operation section main body 3a and perform advancing and retreating motions to execute operations to realize other functions of the endoscope 1. In such a case, a direction in which the switch buttons (the air feeding/water feeding button 21 and the suction button 22) are pressed and advances and retreats (an arrow T in FIG. 1; hereinafter, referred to as an advancing and retreating direction (translating direction) T of the switch buttons) is a direction in which the universal cable 4 extends with respect to the operation section main body 3a.

The plurality of operation members 11 are video-system operation switch that are allocated to perform operations (stopping, recording, photometry switching, image enlargement, and the like) on an endoscope image, for example. In the endoscope 1 illustrated in FIG. 1, a configuration example in which four press button-type operation members are provided, for example, is illustrated. The switch button 21 or 22 is translatable in a translating direction T.

The center axis Ax of the operation knob 9 can be adjusted between a first configuration and a second configuration. In a view in a longitudinal direction S of the operation section main body 3a, in the first configuration, the center axis Ax of the operation knob 9 is configured to be adjusted such that the center axis Ax of the operation knob 9 is perpendicular to each of the longitudinal direction S of the operation section main body 3a and the translating direction T of the switch button 21 or 22. In the view in the longitudinal direction S of the operation section main body 3a, in the second configuration, the center axis Ax of the operation knob 9 is configured to be tilted with respect to a direction that is perpendicular to each of the longitudinal direction S of the operation section main body 3a and the translating direction T of the switch button 21 or 22. The center axis Ax of the operation knob 9 is configured to be tilted such that the operation knob 9 is tilted toward a side of the operation section main body 3a where the switch button 21 or 22 is located. The center axis Ax of the operation knob 9 is configured to be changed a tilted angle between a first angle and a second angle with respect to at least one of the longitudinal direction S of the operation section main body 3a and the translating direction T of the switch button 21 or 22. The first angle and the second angle can be not less than 1 degree and is not more than 30 degrees, and the first angle and the second angle can be different.

The air feeding/water feeding button 21 is an operation button and a switch button for performing sending control of a fluid to be sent from a fluid sending section (not illustrated) provided in the distal end section 5 to outside. For example, air feeding is performed by blocking a small hole at a center of the air feeding/water feeding button 21 with a finger. Also, water feeing is performed by pressing the air feeding/water feeding button 21.

In other words, the air feeding/water feeding button 21 is a switch button that performs operations to give and receive a fluid between the operation section 3 and the distal end of the insertion section 2.

The suction button 22 is a control operation button for setting a negative pressure inside the treatment instrument insertion channel (not illustrated). For example, it is possible to set a negative pressure inside the treatment instrument insertion channel by the pressing operation being performed on the suction button 22, and thereby to suction mucus or the like in the vicinity of the distal end section 5 from the distal end opening (not illustrated) of the treatment instrument insertion channel.

The universal cable 4 is a composite cable extending from one side surface of the operation section 3. A scope connector 12 is located at a distal end of the universal cable 4.

The scope connector 12 is a connector member that includes an electric contact that is connected to a video processor (not illustrated) that is an external device including a light source device. The scope connector 12 is configured to further include a light guide connector 13 and the like.

A light guide bundle (not illustrated), various signal lines (not illustrated), and the like are inserted from the scope connector 12 to the universal cable 4, the operation section 3, and the distal end section 5 of the insertion section 2. Here, the light guide bundle is a configuration member that transmits a light beam emitted from a light source device included in a video processor, which is not illustrated, to the distal end section 5 of the insertion section 2. The light beam transmitted to the distal end section 5 by the light guide bundle is emitted from the illumination unit (not illustrated) provided in the distal end section 5 as illumination light for irradiating an observation target.

Also, the various signal lines include, for example, an image pickup cable that transmits an image signal (image data) acquired by the image pickup unit (not illustrated) provided inside the distal end section 5 to the video processor (not illustrated), a control signal cable that transmits a control signal issued by the video processor to a configuration unit such as the image pickup unit, and the like.

First Embodiment

The present disclosure is applied to the endoscope 1 configured as described above. A configuration of an endoscope according to a first embodiment of the present disclosure will be described below in detail.

Figure 2:
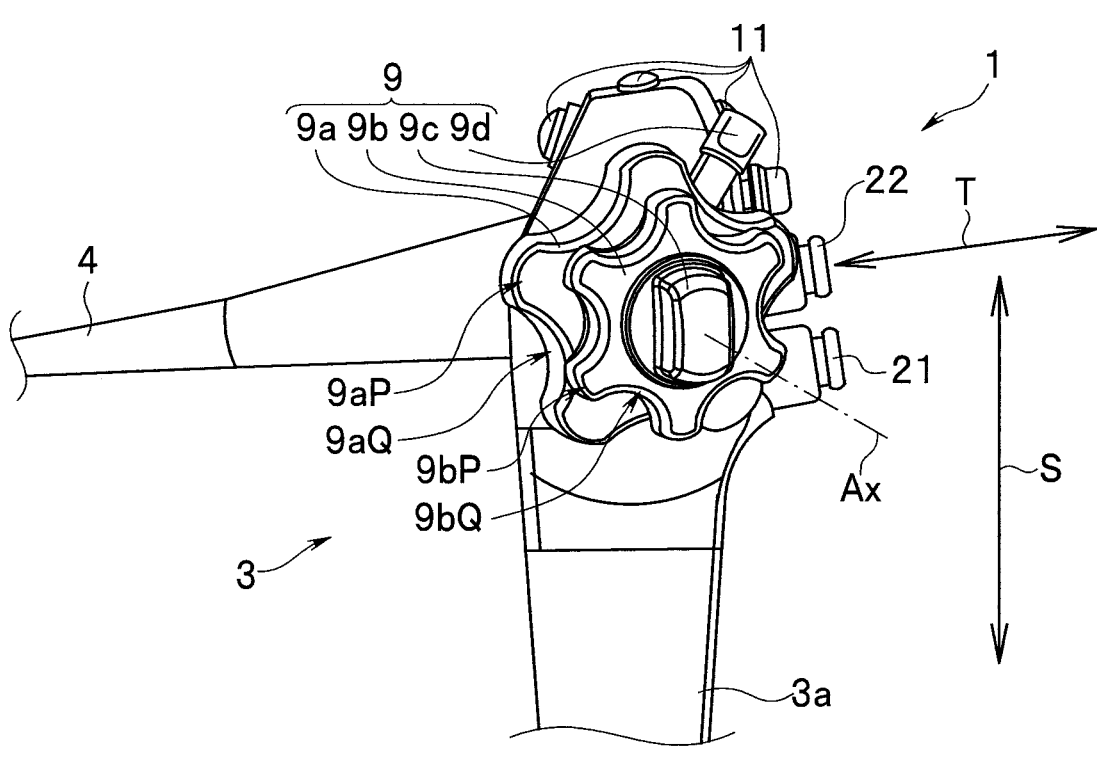
FIG. 2 is a main part enlarged perspective view illustrating an operation section in an endoscope according to a first embodiment of the present disclosure in an enlarged manner.
Figure 3:
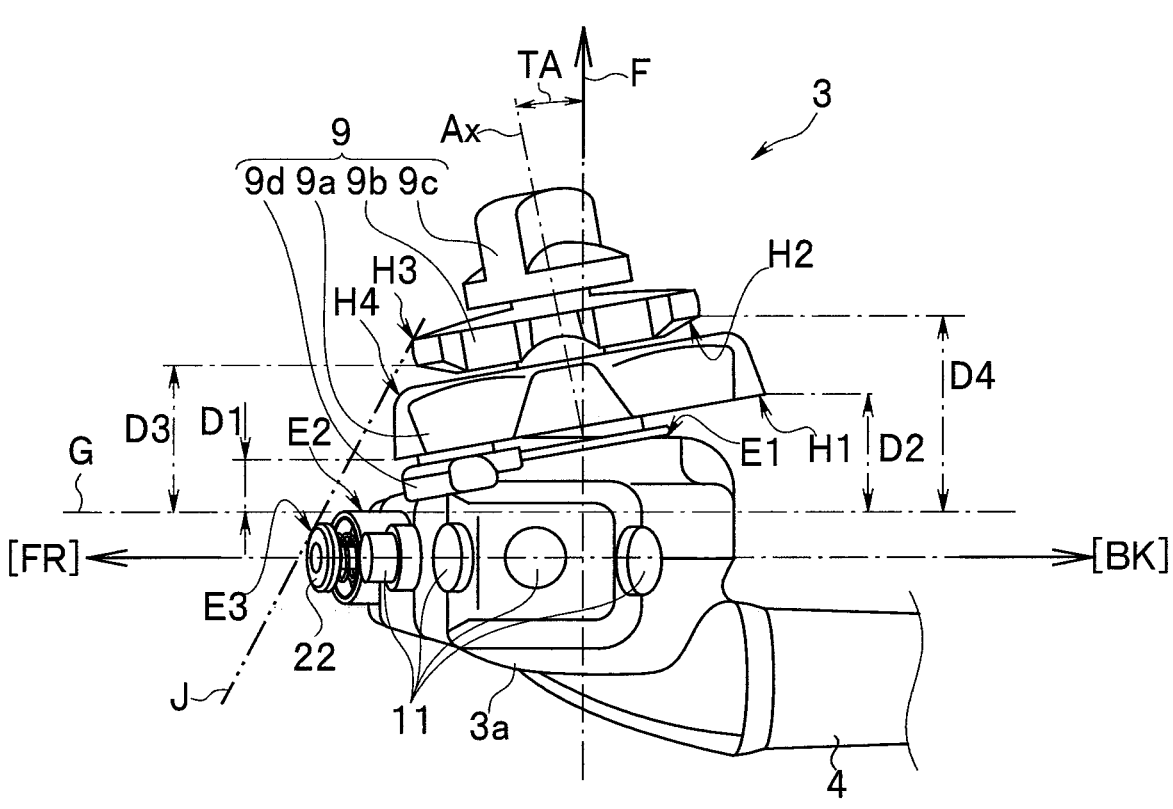
FIG. 3 is a plan view of the endoscope according to the first embodiment of the present disclosure when seen in a direction of an arrow [A] in FIG. 1.

FIG. 2 is a main part enlarged perspective view illustrating an operation section in the endoscope according to the first embodiment in an enlarged manner. FIG. 3 is a plan view of the endoscope according to the first embodiment of the present disclosure when seen in a direction of an arrow [A] in FIG. 1.

A bending operation knob 9 in the endoscope according to the first embodiment is an operation member that acts on a bending operation mechanism, which is not illustrated, and causes a bending section 6 to be actively bent around a long axis of an insertion section 2. Specifically, the bending operation knob 9 includes a plurality of operation members (9a, 9b, 9c, and 9d), each of which is used when a bending operation of the bending section 6 is performed, or when a bent state of the bending section 6 is fixed, or when the fixing state of the bending section 6 is released. The insertion section 2 includes the bending section 6 connecting a distal end section to a flexible tube section 7. The bending section 2 that is configured to bend in a direction that intersects the longitudinal direction S of the operation section main body 3a.

Here, a bending wire is a wire member that is a long member inserted into and disposed inside the insertion section 2 and the operation section 3 between a distal end of the bending section 6 and the bending operation knob 9. Note that illustration of the configuration of the bending operation mechanism including the bending wire is omitted in FIGS. 1 to 3 on the assumption that a mechanism that is substantially same as the mechanism applied to a typical endoscope in the related art is applied, and detailed description will be omitted.

The bending operation knob 9 is an operation member that performs a bending operation on the bending section 6. The bending operation knob 9 includes a UD bending operation knob 9a, an RL bending operation knob 9b, an RL bending fixation knob 9c, and a UD bending fixation lever 9d.

The UD bending operation knob 9a is a first operation knob that is a rotation-type operation member contributing to a bending operation of the bending section 6 in the up-down (UD) direction. The RL bending operation knob 9b is a second operation knob that is a rotation-type operation member contributing to a bending operation of the bending section 6 in the left-right (LR) direction. The RL bending fixation knob 9c is a rotation-type operation member to fix rotation of the RL bending operation knob 9b at a predetermined position. The UD bending fixation lever 9d is a lever-type operation member to fix rotation of the UD bending operation knob 9a at a predetermined position. The operation knob 9 includes the first operation knob 9a and the second operation knob 9b, the first operation knob 9a and the second operation knob 9b are arranged along the center axis Ax of the operation knob 9 with the first operation knob 9a closer to the operation section main body 3a than the second operation knob 9b.

The UD bending operation knob 9a, the RL bending operation knob 9b, the RL bending fixation knob 9c, and the UD bending fixation lever 9d are rotatably located on a same axis. In such a case, the UD bending fixation lever 9d, the UD bending operation knob 9a, the RL bending operation knob 9b, and the RL bending fixation knob 9c are disposed in the order from the side close to an operation section main body 3a to overlap along a center axis Ax (see FIGS. 2 and 3) of the bending operation knob 9.

Each of the UD bending operation knob 9a, the RL bending operation knob 9b, the RL bending fixation knob 9c, and the UD bending fixation lever 9d is configured to be able to rotate forward and backward within a predetermined range around the center axis Ax of the bending operation knob 9.

Note that each of the UD bending operation knob 9a and the RL bending operation knob 9b is formed into a form in which a plurality of projecting sections (9aP and 9bP) and recessed sections (9aQ and 9bQ) are alternately aligned in a circumferential direction at an outer peripheral portion. With such a form, the UD bending operation knob 9a and the RL bending operation knob 9b are formed into a shape suitable to perform a rotating operation with a small amount of force caused by fingers.

In the endoscope 1 according to the first embodiment of the present disclosure, the center axis Ax of the bending operation knob 9 is disposed to be inclined (or be tilted) with respect to a direction (see an arrow F in FIG. 3) that is perpendicular to each of a longitudinal direction S (see FIGS. 1 and 2) of the operation section main body 3a and an advancing and retreating direction T (see FIGS. 1 and 2) of a switch button when seen from above the operation section 3 in the longitudinal direction S. In a view in a direction that is perpendicular to each of the longitudinal direction S of the operation section main body 3a and the translating direction T of the switch button 21 or 22, the center axis Ax of the operation knob 9 is configured to be tilted toward a location on the operation section main body 3a where the insertion section 2 is connected.

In other words, the bending operation knob 9 is disposed such that the center axis Ax is inclined with respect to a surface (hereinafter, referred to as an operation knob end surface; see a reference sign E1 in FIG. 3) on which the bending operation knob 9 is located in the operation section main body 3a as illustrated in FIG. 3.

In such a case, as for the inclination of the center axis Ax, the center axis is inclined toward an operation section front side FR (see FIG. 3) in the advancing and retreating direction T of the switch buttons (21 and 22). An inclination angle TA (see FIG. 3) here is set to an acute angle.

In other words, the center axis Ax of the bending operation knob 9 is disposed to be inclined in a direction in which the bending operation knob 9 approaches the side where the switch buttons (21 and 22) are provided.

Here, the center axis Ax of the bending operation knob 9 is disposed to be inclined by a predetermined angle within a range of an angle of not less than 1 degree and not more than 30 degrees with respect to the direction F that is perpendicular to each of the longitudinal direction S and the advancing and retreating direction T of the switch buttons. The operation knob 9 is configured to be tilted to form the acute angle that is not less than 1 degree and is not more than 30 degrees. The acute angle is not less than 5 degrees and is less than 10 degrees.

FIG. 55 is a diagram illustrating results of inspecting relationships between inclination angles of the bending operation knob of the endoscope and operability. The inspection results are results obtained by asking a plurality of subjects randomly extracted from subjects with different conditions, such as hand sizes, body sizes, and sex differences, whether operability was good or not good depending on inclination angles of the bending operation knob. In FIG. 55, the inclination angles of the bending operation knob and degrees of improvement in operability with respect to a state where the bending operation knob is not inclined (or is not tilted) (inclination angle=0 degree) are illustrated.

Note that in FIG. 55, the reference sign "B" indicates "not good" and represents an answer that a difficulty is found in utilization or no change is felt in operability. The reference sign "G" indicates "good" and represents an answer that a slight improvement is felt in operability. The reference sign "EXC" indicates "excellent" and represents an answer that an improvement is felt in operability.

In consideration of the inspection results in FIG. 55, the center axis Ax of the bending operation knob 9 can be disposed to be inclined by a predetermined angle within a range of an angle of not less than 5 degrees and less than 10 degrees with respect to the direction F that is perpendicular to each of the longitudinal direction S and the advancing and retreating direction T of the switch buttons.

Further, the center axis Ax of the bending operation knob 9 is disposed to be inclined at an angle of about 7.5 degrees with respect to the direction F that is perpendicular to each of the longitudinal direction S and the advancing and retreating direction T of the switch buttons.

The bending operation knob 9 is configured to include at least a UD bending operation knob 9a and an RL bending operation knob 9b from the side close to the operation section main body 3a along the center axis Ax of the bending operation knob 9 as described above. In such a case, a distance (see reference signs D1 and D2 in FIG. 3) between a line (see a reference sign G in FIG. 3) that passes through an end surface (see a reference sign E2 in FIG. 3) of the switch buttons (21 and 22) and is parallel to the advancing and retreating direction T of the switch button and an outermost peripheral portion of a lower end surface (a reference sign H1 in FIG. 3) of the UD bending operation knob 9a when seen from above in the longitudinal direction S (see FIG. 3) is set in the operation section 3 such that a distance D2 on a side (an operation section back side BK; see FIG. 3) where the switch buttons (21 and 22) are not provided is longer than a distance D1 on a side (an operation section front side FR) where the switch buttons (21 and 22) are provided (D2>D1).

Similarly, a distance between a line (first line) G that passes through the switch button end surface E2 and is parallel to the advancing and retreating direction T of the switch buttons and a lower end surface (a reference sign H2 in FIG. 3) of the RL bending operation knob 9b when seen from above in the longitudinal direction S (see FIG. 3) is set such that a distance D4 on a side (operation section back side BK) where the switch buttons are not provided is longer than a distance D3 on a side (operation section front side FR) where the switch buttons are provided (D4>D3).

An imaginary line that passes through an end surface of the switch button 21 or 22 and that is parallel to the translating direction T of the switch button 21 or 22 defines the first line G. In the view in the longitudinal direction S of the operation section main body 3a, a shortest distance between the first line G and an end surface of the first operation knob 9a is longer on a first side D2 of the center axis Ax of the operation knob 9 where the switch button 21 or 22 is not provided than on a second side D1 of the center axis Ax of the operation knob 9 where the switch button 21 or 22 is provided. In the view in the longitudinal direction S of the operation section main body 3a, a shortest distance between the first line G and an end surface of the second operation knob 9b is longer on a first side D4 of the center axis Ax of the operation knob 9 where the switch button 21 or 22 is not provided than on a second side D3 of the center axis Ax of the operation knob 9 where the switch button 21 or 22 is provided.

Incidentally, a virtual line J that connects an end section E3 of the switch buttons (21 and 22) and an end section H3 of the RL bending operation knob 9b when the operation section 3 is seen in the longitudinal direction S (for example, when seen from above) is assumed in the operation section 3 as illustrated in FIG. 3.

In such a case, the operation section 3 in the endoscope 1 according to the first embodiment has a structure in which an end section H4 of the UD bending operation knob 9a is disposed not to stick out from the virtual line J in an ordinary state.

More specifically, the operation section 3 has a structure in which end section H4 at the part where the projecting portion 9aP of the UD bending operation knob 9a projects to a maximum extent in a radial direction from the center axis A does not sticks out from the virtual line J connecting the end section E3 of the switch buttons to the end section H3 at the part where the projecting portion 9bP of the bending operation knob 9b projects to the maximum extent in the radial direction from the center axis Ax.

In other words, the operation section 3 has a structure in which a ridgeline of the end section H4 at the part of the UD bending operation knob 9a projecting to the maximum extend in the radial direction from the center axis Ax is disposed not to stick out from the virtual line J connecting a ridgeline of the end section H3 at the part of the RL bending operation knob 9b projecting to the maximum extent in the radial direction from the center axis Ax to a ridgeline of the end section E3 of the switch buttons as illustrated in FIG. 3 when seen in the longitudinal direction S (from above, for example).

Also, the air feeding/water feeding button 21 and the suction button 22 as a plurality of switch buttons are disposed in the direction which is the longitudinal direction of the operation section 3 as illustrated in FIG. 2 and the like. In such a case, the end section H4 of the UD bending operation knob 9*a* is disposed not to stick out from the virtual line J connecting the end section E3 of the switch buttons to the end section H3 of the RL bending operation knob 9*b* when the operation section 3 is seen from above in the longitudinal direction S (see FIG. 3).

Note that the plurality of switch buttons (21 and 22) is set such that projecting amounts by which the switch buttons (21 and 22) project from the outer surface of the operation section main body 3*a* are substantially the same.

Also, in the aforementioned configuration example, an example in which the two operation knobs (9*a* and 9*b*) are configured such that the UD bending operation knob 9*a* has a larger diameter than the diameter of the RL bending operation knob 9*b* is illustrated. However, the sizes of the knobs are not limited to the illustrative configuration example. For example, the UD bending operation knob 9*a* and the RL bending operation knob 9*b* may be configured to have substantially the same diameters.

Even in a case where such a configuration is employed, for the end section H4 of the UD bending operation knob 9*a* can be disposed not to stick out from the virtual line J connecting the end section E3 of the switch buttons to the end section H3 of the RL bending operation knob 9*b* when the operation section 3 is seen from above in the longitudinal direction S (see FIG. 3).

Incidentally, the bending operation mechanism that realizes a bending operation of the bending section 6 by acting in conjunction with a rotating operation of the bending operation knob 9 which is a bending operation member is located inside the operation section main body 3*a*.

Figure 4:
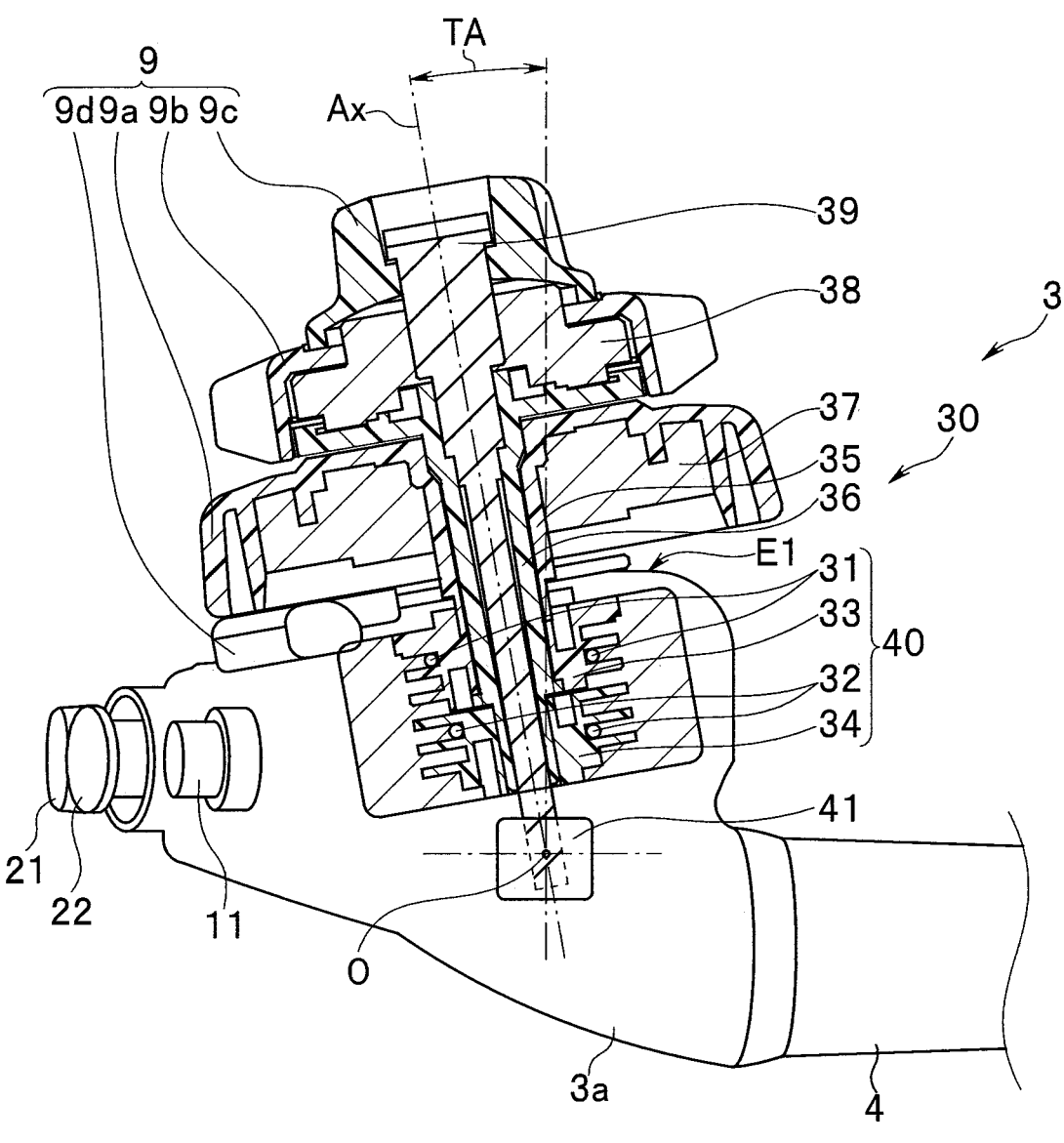
FIG. 4 is a sectional view illustrating a schematic configuration of a bending operation mechanism including a bending operation member of the endoscope according to the first embodiment of the present disclosure.

As the bending operation mechanism that is applied to the endoscope 1 according to the first embodiment of the present disclosure, a mechanism with a configuration that is substantially the same as the configuration of the mechanism applied in a typical endoscope in the related art as described above. FIG. 4 is a diagram illustrating, in a section, a schematic configuration of the bending operation mechanism including the bending operation member in the endoscope according to the first embodiment of the present disclosure.

The bending operation mechanism 30 includes bending wires (31 and 32), a pulley unit 40 including pulleys (33 and 34), rotation shaft members (35 and 36), brake mechanisms (37 and 38), a fixing shaft 39, a fixing base 41, and the like. Note that the bending operation mechanism 30 includes the bending operation knob 9 which is a bending operation member. The operation section main body 3*a* can include at least one pulley 33 and/or 34 around which at least one wire 31 and/or 32 is wound. The at least one rotation shaft 35 and/or 36 of the at least one pulley 33 and/or 34 parallel to or coaxial with the center axis Ax of the operation knob 9. Rotation of the operation knob 9 about the center axis Ax causes the at least one wire 31 and/or 32 to pull the bending section 6 to bend the bending section 6.

The bending wires are wire members that are long members and cause the bending section 6 to be bent by pulling a distal end site of the bending section 6 in conjunction with each of rotation of the UD bending operation knob 9*a* and rotation of the RL bending operation knob 9*b*. The bending wires include first bending wires (UD) 31 and second bending wires (RL) 32.

A pair of first bending wires (UD) 31 and a pair of second bending wires (RL) 32 are provided. The first bending wires (UD) 31 include a pair of wires that contribute to a bending operation in the up-down direction. The second bending wires (RL) 32 include a pair of wires that contribute to a bending operation in the left-right direction.

The pulley unit 40 is formed to include pulleys (33 and 34), a pulley case and a wire cover, which are not illustrated, and the like. Among the components, the pulleys are disc-shaped members around which each of the bending wires (31 and 32) is wound by rotating in conjunction with each of rotation of the UD bending operation knob 9*a* and rotation of the RL bending operation knob 9*b*. The pulleys include a first pulley (UD) 33 and a second pulley (RL) 34. The first pulley (UD) 33 is connected to the UD bending operation knob 9*a* through the rotation shaft member (35), rotates in conjunction with rotation of the UD bending operation knob 9*a*, and reels in the first bending wire (UD) 31. The second pulley (RL) 34 is connected to the RL bending operation knob 9*b* through the rotation shaft member (36), is rotated in conjunction with rotation of the RL bending operation knob 9*b*, and reels in the second bending wire (RL) 32. A first pulley 33 is connected to the first operation knob 9*a* and a second pulley 34 is connected to the second operation knob 9*b*. Rotation of the first operation knob 9*a* about the center axis Ax causes a first wire 31 to pull the bending section 6 to bend the bending section 6 in a first direction, and rotation of the second operation knob 9*b* about the center axis Ax causes a second wire 32 to pull the bending section 6 to bend the bending section 6 in a second direction, the second direction different from the first direction.

Each rotation shaft member is a shaft member provided between the UD bending operation knob 9*a* or the RL bending operation knob 9*b* and each corresponding pulley (33 or 34) and transmits each of the rotation forces of the bending operation knob 9 (9*a* and 9*b*) to each pulley (33 or 34).

The rotation shaft members are provided along the center axis Ax. In such a case, the rotation shaft members are set in parallel to or coaxial with the center axis Ax of the bending operation knob 9. The rotation shaft members include the first shaft member (UD) 35 and the second shaft member (RL) 36.

The first shaft member (UD) 35 is a rotation shaft member that transmits a rotation force of the UD bending operation knob 9*a* to the first pulley (UD) 33. The second shaft member (RL) 36 is a rotation shaft member that transmits a rotation force of the RL bending operation knob 9*b* to the second pulley (RL) 34.

The brake mechanism is a mechanism for holding each of rotation positions of the UD bending operation knob 9*a* and the RL bending operation knob 9*b*. The brake mechanism includes the RL bending fixation knob 9*c* and the UD bending fixation lever 9*d*.

The brake mechanism includes a first brake mechanism (UD) 37 and a second brake mechanism (RL) 38. The first brake mechanism (UD) 37 acts on the UD bending operation knob 9*a* and holds a rotation position of the UD bending operation knob 9*a*. The second brake mechanism (RL) 38 acts on the RL bending operation knob 9*b* and holds a rotation position of the RL bending operation knob 9*b*.

Note that the brake mechanism is a part that is not related directly to the present disclosure. Therefore, for details of the brake mechanism, detailed illustration and description will be omitted on the assumption that the same mechanism as the mechanism applied to the bending operation mechanism in the endoscope in the related art is applied.

The fixing shaft 39 is a shaft member that penetrates through the RL bending fixation knob 9*c*, the first brake mechanism (UD) 37, and the second shaft member (RL) 36. The fixing shaft 39 has a function of transmitting rotation of the RL bending fixation knob 9*c* to the first brake mechanism (UD) 37.

The fixing base 41 is a pedestal member that supports the fixing shaft 39 and maintains an inclined state (tilted state). The fixing base 41 includes two plate members disposed such that the fixing shaft 39 is sandwiched, for example. The fixing shaft 39 in such a case has an inclination center at a predetermined position (reference sign O) in the vicinity of the distal end.

The fixing base 41 is fixed to an internal fixing section (not illustrated) of the operation section main body 3a. Alternatively, the fixing base 41 may be in a form in which the fixing base 41 is formed integrally with an inner wall surface of the operation section main body 3a.

In the thus configured bending operation mechanism 30, the center axis Ax of the bending operation knob 9 is disposed to be inclined by a predetermined angle in a predetermined direction with respect to the operation knob end surface E1 of the operation section main body 3a as described above and is fixed at the fixing base 41 such that the state is maintained.

Figure 5:
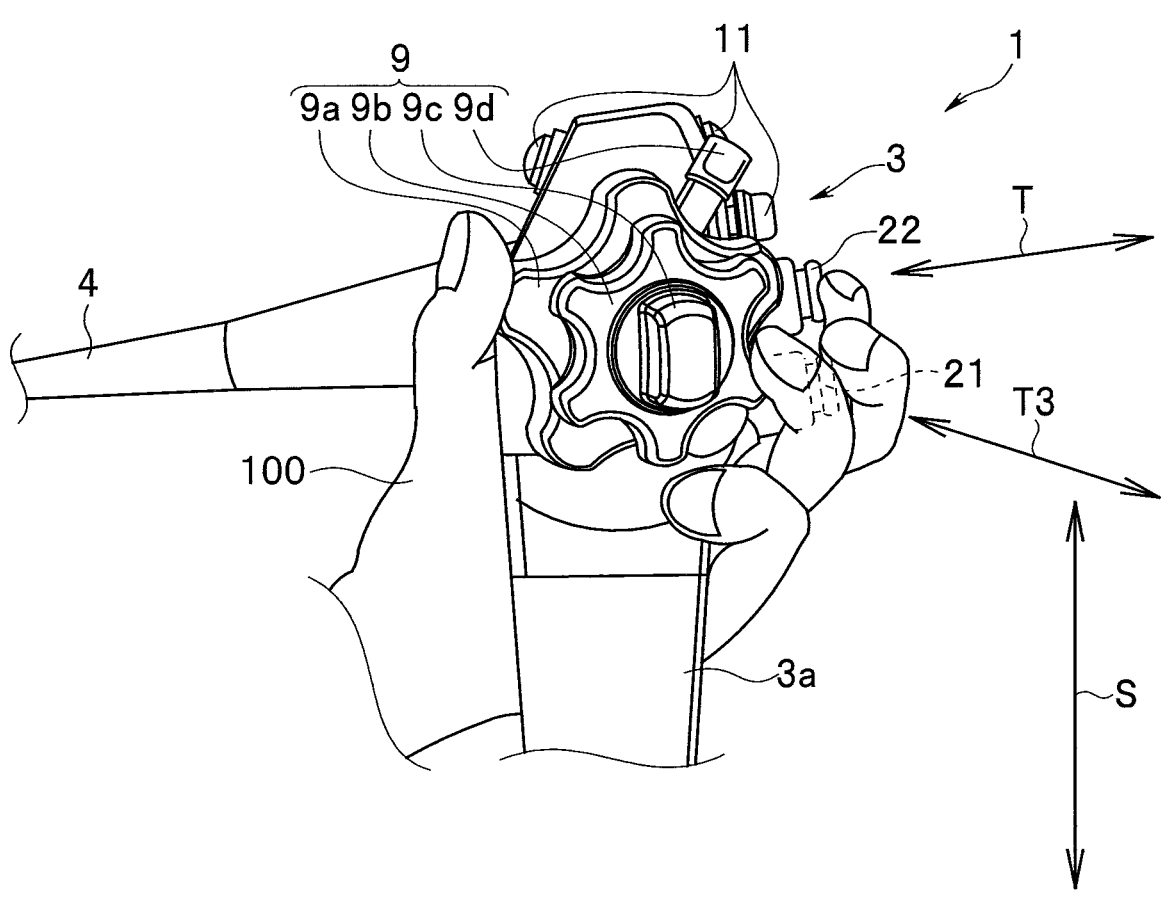
FIG. 5 is a conceptual diagram of a state where a user grasps and operates an operation section main body at the time of utilization of the endoscope according to the first embodiment of the present disclosure in a view from a side.
Figure 6:
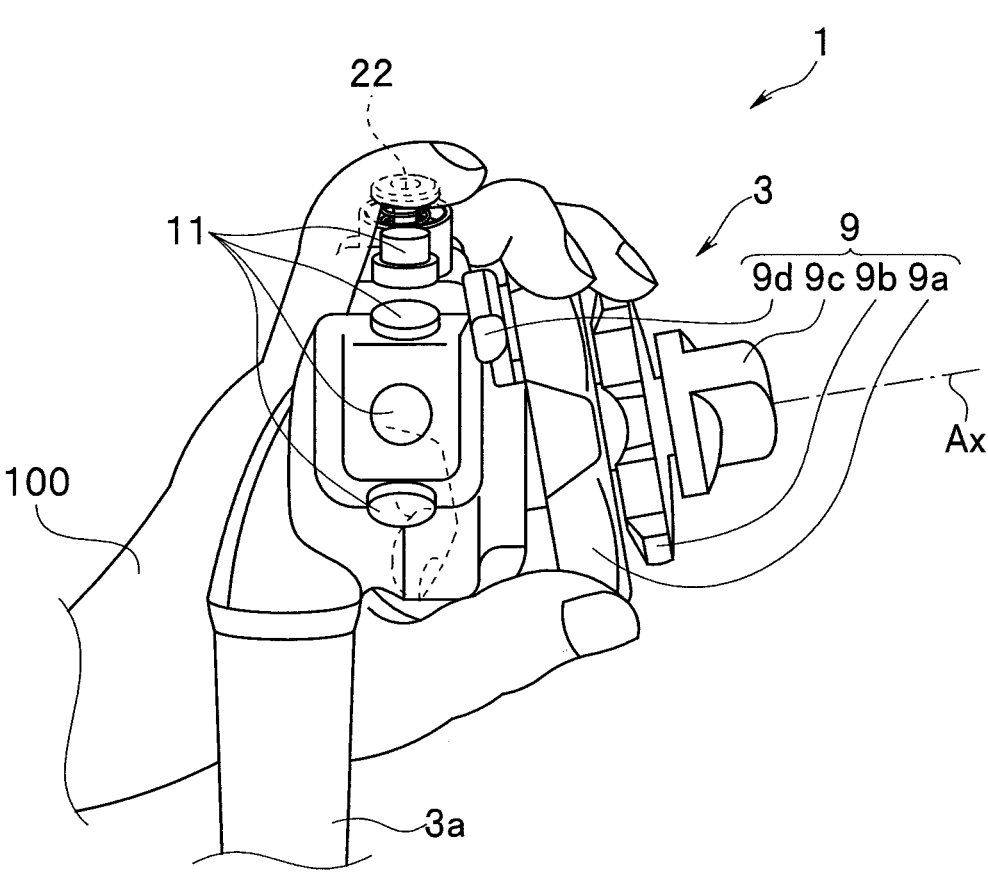
FIG. 6 is a conceptual diagram of the state where the user grasps and operates the operation section main body at the time of utilization of the endoscope according to the first embodiment of the present disclosure in a view from above.

Effects of the thus configured endoscope 1 according to the first embodiment of the present disclosure will be described below. FIGS. 5 and 6 are diagrams conceptually illustrating a state where the user grasps and operates the operation section main body when the user uses the endoscope according to the first embodiment of the present disclosure. Out of the drawings, FIG. 5 illustrates a side surface (a surface on the side where the bending operation knob is disposed) of the endoscope, and FIG. 6 illustrates a plane seen from above the endoscope according to the first embodiment of the present disclosure.

When the endoscope 1 is used, the user grasps the operation section main body 3a of the operation section 3 by using a left hand 100 in an ordinary case. Typically, the user causes a site between a thumb and an index finger to abut the vicinity of the site where the universal cable 4 extends behind the operation section main body 3a when the user grasps the operation section main body 3a. The thumb of the left hand 100 is thus naturally disposed at a position where the bending operation knob 9 can be operated.

If the fingers other than the thumb of the left hand 100 are stretched in the state, the middle finger, and the ring finger, for example, are disposed at positions where the bending operation knob 9 can be operated from the front side of the operation section main body 3a. Also, the index finger is disposed at a position where the switch buttons (21 and 22) are easily operated in the advancing and retreating direction T in a naturally stretched state. Here, the operation section main body 3a is brought into a state where the operation section main body 3a is grasped by the site between the thumb and the index finger and the little finger.

As described above, according to the first embodiment, the center axis Ax of the bending operation knob 9 provided in the operation section main body 3a of the operation section 3 is disposed to be inclined (or be tilted) with respect to the direction F that is perpendicular to each of the longitudinal direction S and the advancing and retreating direction T of the switch buttons when seen from above the operation section 3 in the longitudinal direction S of the operation section main body 3a in the endoscope including the bending operation mechanism that realizes the bending operation of the bending section by operating the bending operation member provided in the operation section main body.

In such a case, as for the inclination of the center axis Ax, the center axis Ax is inclined toward the operation section front side FR in the advancing and retreating direction T of the switch buttons. The inclination angle TA here is an acute angle.

In other words, the center axis Ax of the bending operation knob 9 is disposed to be inclined in the direction in which the bending operation knob 9 approaches the side where the switch buttons (21 and 22) are provided.

In such a case, the center axis Ax of the bending operation knob 9 is disposed to be inclined by a predetermined angle within a range of an angle of not less than 1 degree and not more than 30 degrees with respect to the direction F that is perpendicular to each of the longitudinal direction S and the advancing and retreating direction T of the switch buttons.

The center axis Ax of the bending operation knob 9 can be disposed to be inclined by a predetermined angle within a range of an angle of not less than 5 degrees and less than 10 degrees with respect to the direction F that is perpendicular to each of the longitudinal direction S and the advancing and retreating direction T of the switch buttons (see FIG. 55).

The center axis Ax of the bending operation knob 9 can be disposed to be inclined by an angle of about 7.5 degrees with respect to the direction F that is perpendicular to each of the longitudinal direction S and the advancing and retreating direction T of the switch buttons (see FIG. 55).

With such a configuration, the endoscope 1 according to the first embodiment of the present disclosure can be easily used without imparting a burden on the fingers other than the thumb from among the fingers of the left hand grasping the operation section main body 3a of the operation section 3 as well for the operation of the bending operation knob 9 and switch operations. It is thus possible to facilitate a one-hand operation of the endoscope regardless of individual differences in hand sizes, finger lengths, and the like of users. Therefore, it is possible to contribute to an improvement in operability of the endoscope and to contribute to reduction of a burden during utilization.

Furthermore, it is possible to realize an improvement in operability of the endoscope, to thereby contribute to shortening of the procedure time period, and thus to curb fatigue of the user. At the same time, it is possible to reduce invasiveness in the subject (patient).

Incidentally, the entire mechanism that also includes the bending operation mechanism including the bending operation knob is disposed inside the operation section main body in an inclined state in the first embodiment of the present disclosure. If the configuration unit is disposed to be inclined with respect to a casing inner wall surface when the configuration unit is disposed inside the operation section main body with a substantially box shape in such a manner, there is a trend that a region where the configuration unit occupies inside the casing increases and a large useless region is generated.

On the other hand, in a case of a so-called single-use endoscope in the form in which the endoscope is discarded after a single use, for example, the internal structure of the operation section main body is further simplified for the reason that it is possible to simplify a watertight structure or the like. In consideration of the point, there is large room that allows a structure change for the internal structure of the operation section main body in the case of the single-use endoscope. Therefore, the configuration according to the first embodiment of the present disclosure is optimally applied to a single-use endoscope, in particular, and can be easily applied.

The single-use endoscope can include a single-use component and a multi-use component. The single-use component is disposed or returned to manufacturer of after being used once, and the multi-use component is a reusable component that is repeatedly used.

First Modification

A modification described below is further conceivable for the endoscope 1 according to the first embodiment of the present disclosure.

In the aforementioned endoscope 1 according to the first embodiment, the configuration example in which the center axis Ax of the bending operation knob 9 is disposed to be inclined by a predetermined angle (an angle of about 5 degrees to about 10 degrees, for example) on the side where the switch buttons (21 and 22) are located in the advancing and retreating direction T (see FIG. 5) of the switch buttons is illustrated.

In an endoscope that is conceivable as a first modification, the center axis Ax of the bending operation knob 9 is disposed to be further inclined toward the side where the insertion section 2 is provided in a view in the direction that is perpendicular to each of the longitudinal direction S and the advancing and retreating direction T of the switch buttons.

In other words, the first modification is configured such that the center axis Ax of the bending operation knob 9 is disposed to be inclined in a direction indicated by an arrow T3 in FIG. 5 in addition to the inclination in the direction indicated by the arrow T in FIG. 5. Here, the direction indicated by the arrow T3 in FIG. 5 is a direction in which the middle finger and the ring finger of the left hand easily act when the user grasps the operation section main body 3a, for example.

According to the configuration of the first modification, it is possible to contribute to a further improvement in operability with such a configuration.

Second Modification

Figure 7:
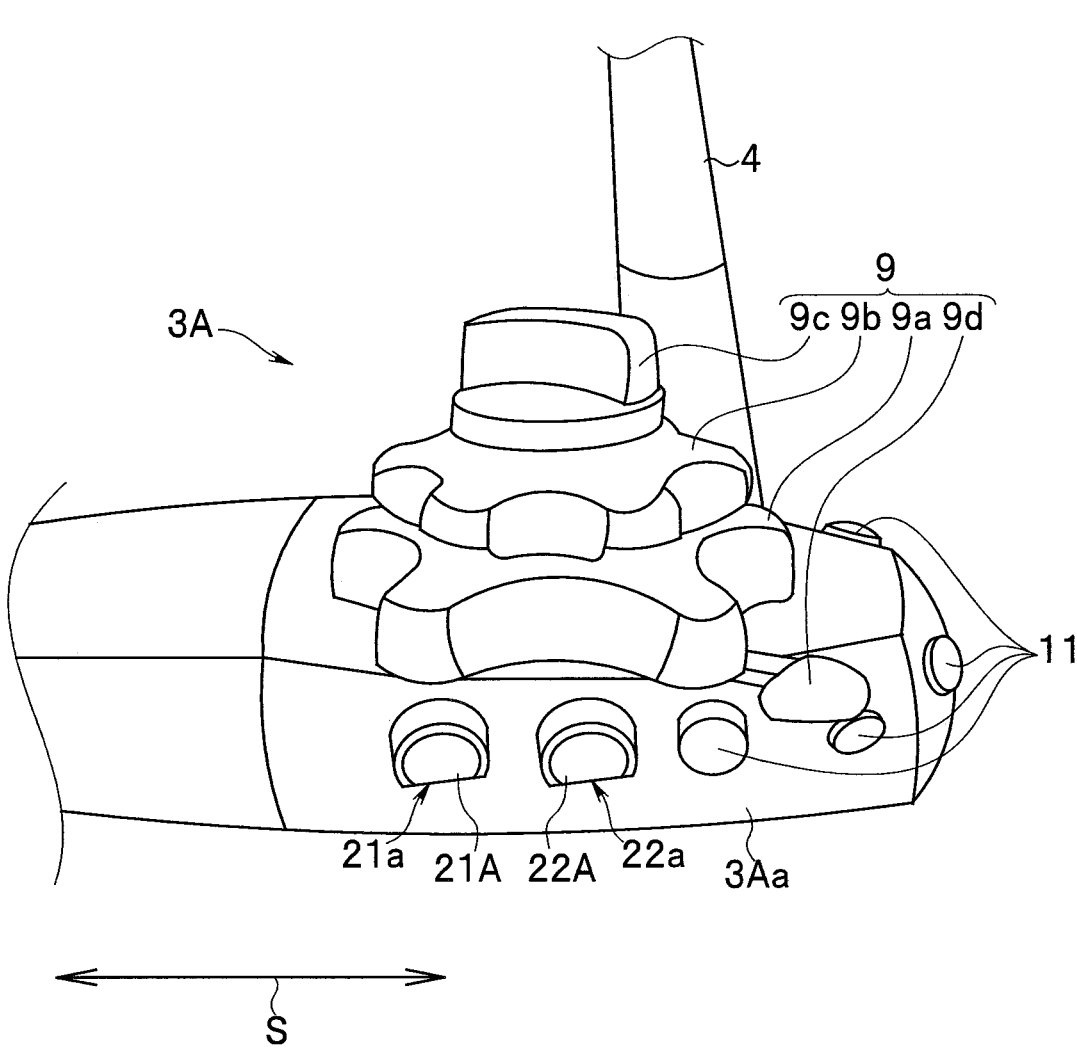
FIG. 7 is a plan view illustrating a second modification of an operation section in the endoscope in FIG. 1 and illustrating a side surface (a disposition surface of a switch button) of the operation section main body.
Figure 8:
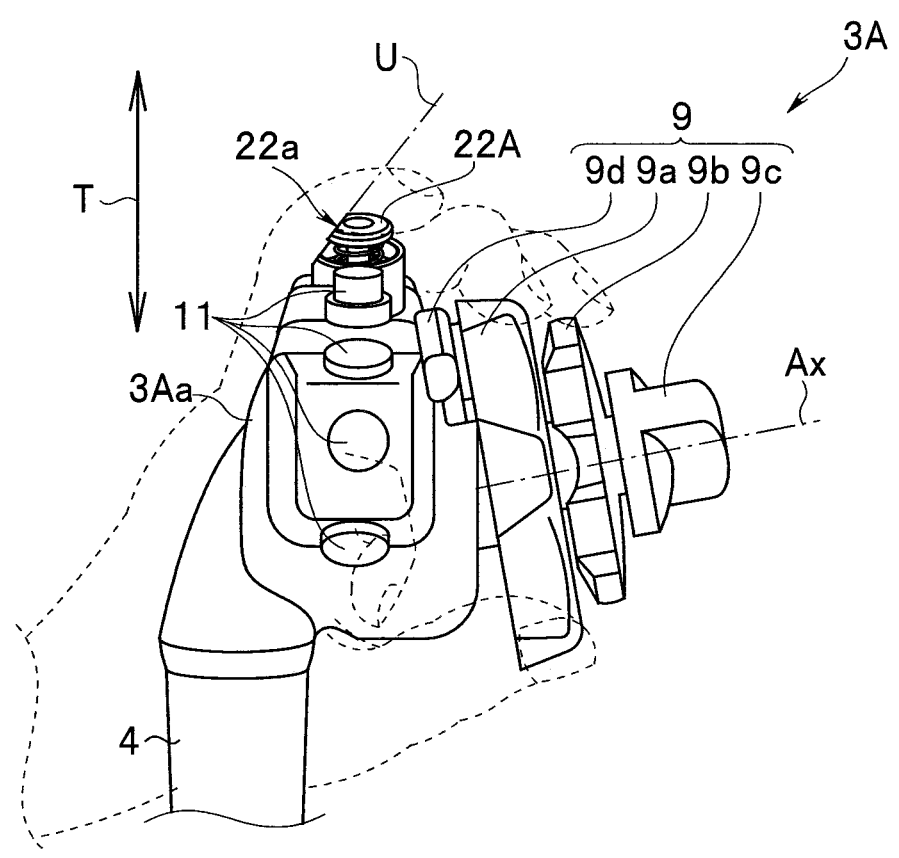
FIG. 8 is a plan view of the operation section main body in FIG. 7 in a view from above.

FIGS. 7 and 8 are diagrams illustrating a modification (second modification) of the operation section in the endoscope. Out of the drawings, FIG. 7 is a plan view illustrating a side surface (a surface on which the switch buttons are located) of an operation section main body. FIG. 8 is a plan view of the operation section main body in a view from above.

In the second modification, the shapes of the switch buttons are different. In other words, end surfaces of switch buttons provided in an operation section main body 3Aa of the operation section 3A illustrated as the second modification is provided with tapered surfaces (21a and 22a) inclined with respect to the advancing and retreating direction T of the switch buttons when seen from above in the longitudinal direction S (see FIG. 8). The other configurations are same as the configurations in the aforementioned first embodiment.

Specifically, a tapered surface (21a or 22a) is formed on each of end surfaces of switch buttons (21A and 22A) as illustrated as an example in FIGS. 7 and 8. Note that any configuration may be employed as long as at least one of the plurality of switch buttons is provided with the tapered surface of the switch button.

In the case of the configuration in which the bending operation knob 9 is disposed to be inclined as described above, an outer peripheral portion of the bending operation knob 9 is disposed in proximity to the switch buttons. In such a case, a trend that a space where fingers access the switch buttons is lightly narrowed is observed. The point may be a factor inhibiting operability of the switch buttons.

Thus, it is considered that the switch buttons are disposed in a direction away from the bending operation knob 9 on a side surface of the operation section main body 3Aa. In the case where such disposition is employed, the switch buttons are disposed at positions close to bases of the fingers. Operability may thus be inhibited.

Thus, a configuration in which tapered surfaces (21a and 22a) are provided at predetermined positions of the switch buttons (21A and 22A) is employed in the second modification. Such a configuration in which the tapered surfaces are provided lead to a configuration in which it is possible to secure a wider region where the fingers access the switch buttons (only the reference sign 22A is illustrated in FIG. 8) as illustrated in FIG. 8. In a view in the longitudinal direction S of the operation section main body 3a, an end surface of the switch button 21 or 22 includes the tapered surface 21a or 22a that is inclined with respect to the translating direction T of the switch button 21 or 22.

Therefore, according to the configuration of the second modification, it is possible to obtain effects that are same as the effects of the aforementioned first embodiment without inhibiting operability of the endoscope 1.

Note that an outline U (see FIG. 8) of the tapered surfaces (21a and 22a) of end surfaces of the switch buttons may be set in accordance with the inclination angle of the center axis Ax of the bending operation knob 9. In such a case, a form in which the outline U is set to be parallel to the center axis Ax of the bending operation knob 9 is also conceivable depending on setting of the inclination angle of the center axis Ax of the bending operation knob 9 although illustration is omitted.

Also, a form in which a part of components configuring the switch buttons (21A and 22A) is configured to be hidden by the end surface of the bending operation knob 9 when seen in the direction that perpendicularly intersecting the advancing and retreating direction T of the switch buttons (21A and 22A) (that is, when seen in the direction facing the switch button located surface; see FIG. 7) is also conceivable depending on the setting of the inclination angle of the center axis Ax of the bending operation knob 9.

Also, in the configuration examples illustrated in the first embodiment and each modification described above, configuration examples, in which the plurality of switch buttons are formed into substantially cylindrical shapes as a whole with surfaces to be pressed by fingers formed into substantially circular shapes. However, the shapes of the switch buttons are not limited to the aforementioned configuration examples. For example, a form in which at least the pressed surfaces are formed into substantially quadrangular shapes instead of the switch buttons with the circular shapes may be employed. The switch buttons with the configuration may have substantially cylindrical overall shapes, or the overall shapes of the switch buttons may be formed into substantially quadrangular prism shapes in accordance with the quadrangular shapes of the pressed surfaces.

In the case where such a configuration is employed, each switch button can be disposed such that one side of the quadrangular shape of the pressed surface substantially perpendicularly intersects the center axis of the bending operation knob.

It is possible to avoid interference with the inclined bending operation knob while securing the area of the pressed surface by forming the pressed surface of the switch button into the substantially quadrangular shape as described above.

Also, height dimensions (that is, dimensions of projection from the surface of the operation section main body) of the plurality of switch buttons (21 and 22) may be set to be lower. Employing such a configuration allows the fingers to more easily reach the switch buttons when the user grasps the operation section main body. It is thus possible to contribute to an improvement in operability.

Second Embodiment

Figure 9:
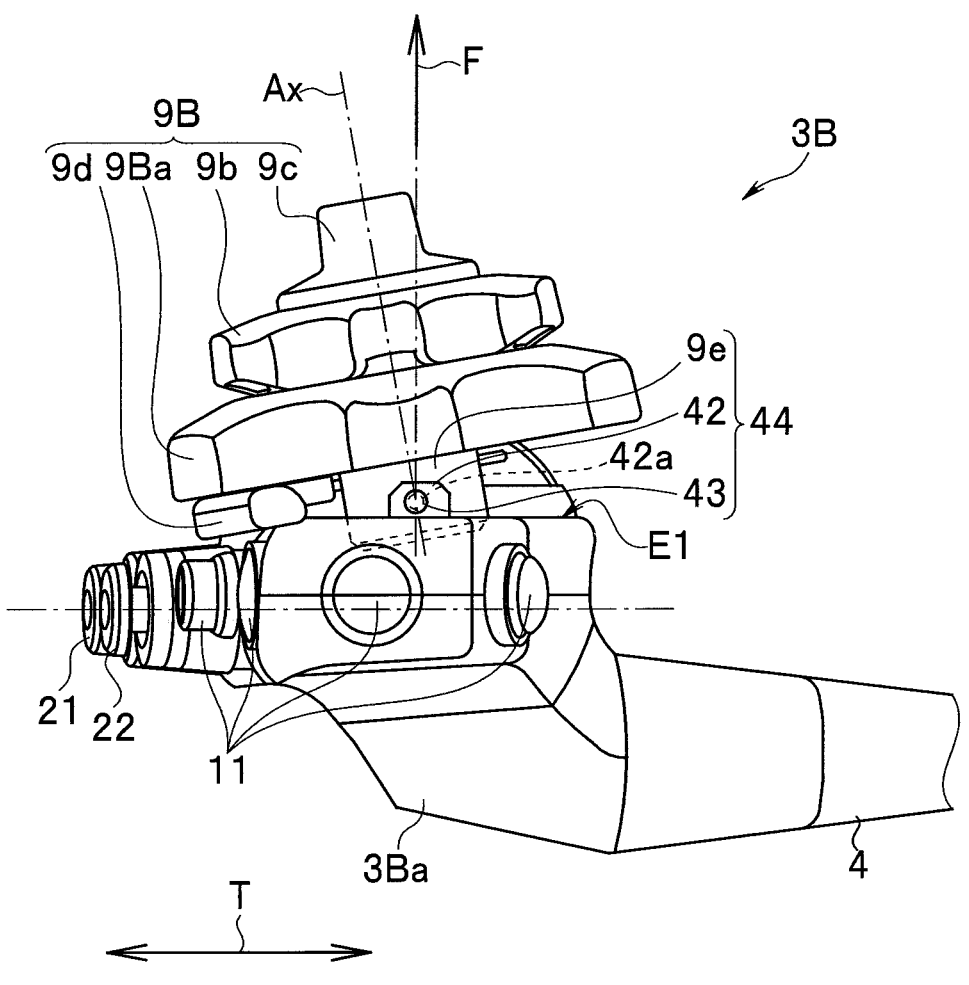
FIG. 9 is a plan view of an operation section main body of an endoscope according to a second embodiment of the present disclosure in a view from above.
Figure 10:
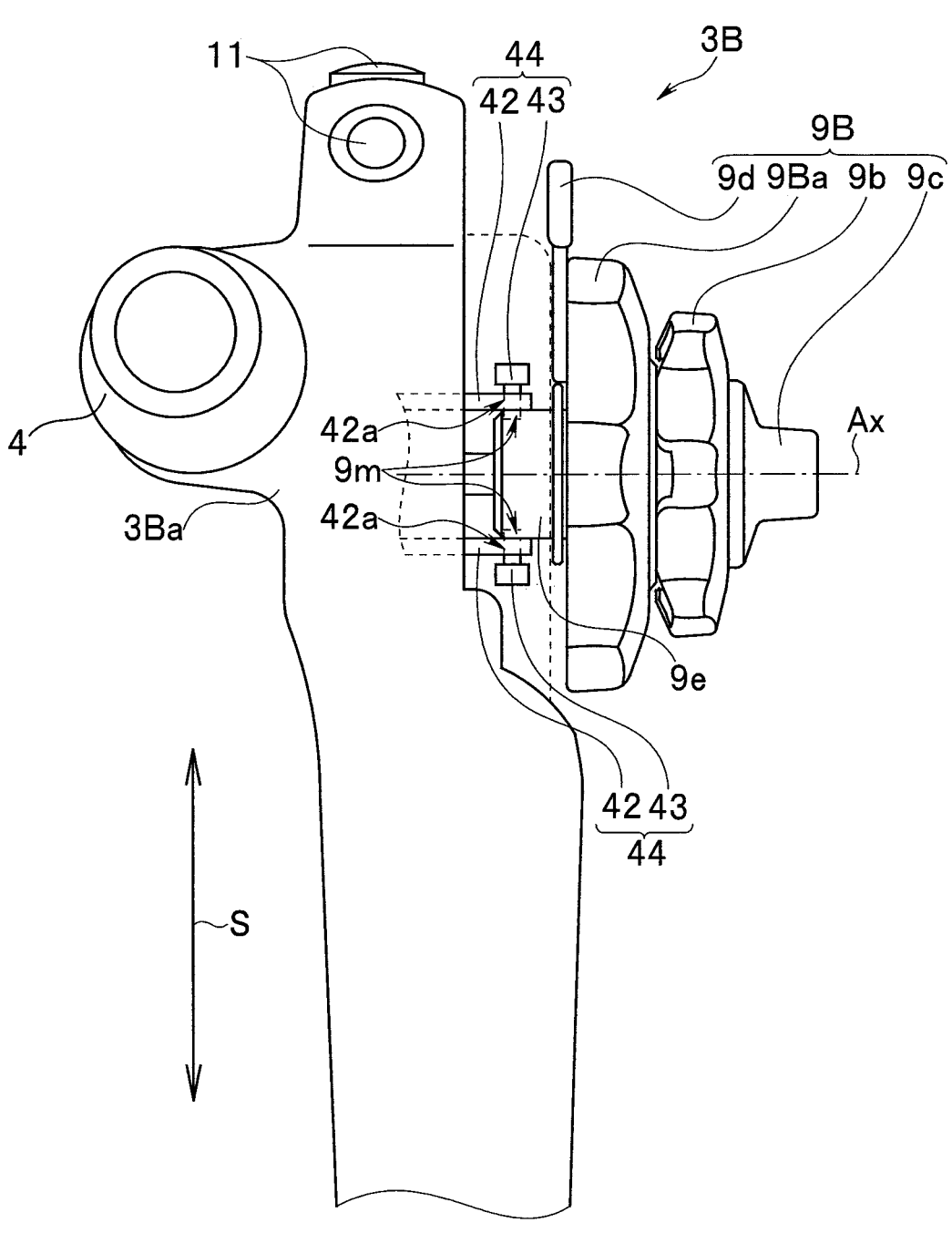
FIG. 10 is a plan view of the operation section main body in FIG. 9 in a view from the back.
Figure 11:
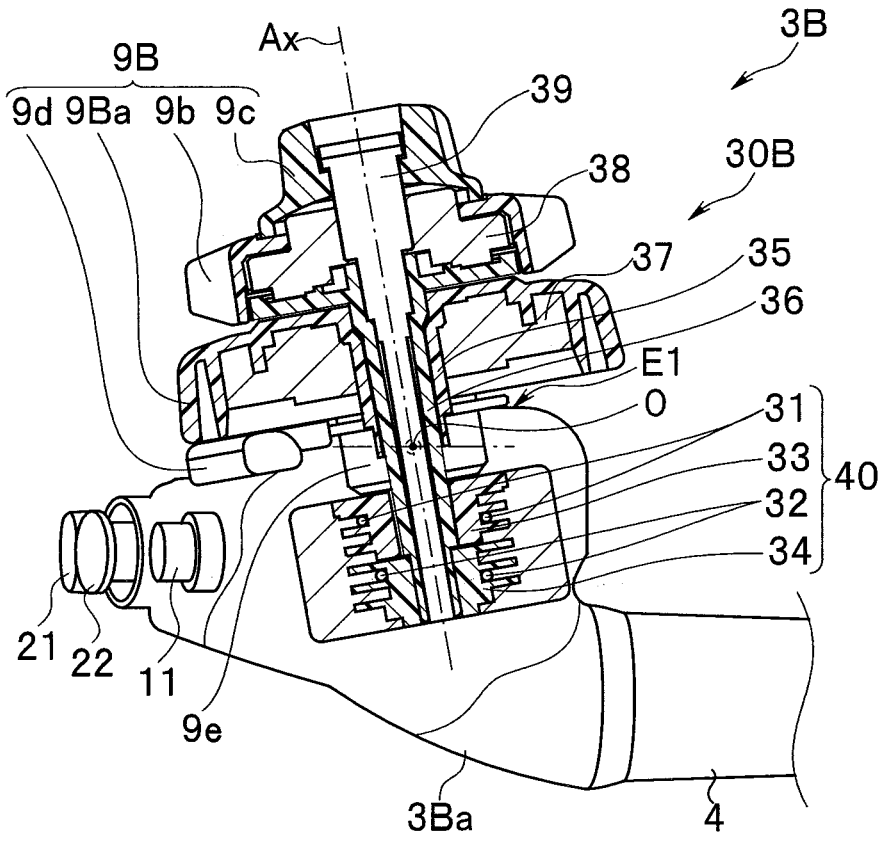
FIG. 11 is a sectional view schematically illustrating main parts of a bending operation mechanism including a bending operation member in the operation section main body in FIG. 9.

Next, a second embodiment of the present disclosure will be described. FIGS. 9 to 11 are diagrams illustrating a second embodiment of the present disclosure. Among the drawings, FIG. 9 is a plan view of an operation section main body in a view from above. FIG. 10 is a plan view of the operation section main body in FIG. 9 in a view from the back. FIG. 11 is a sectional view schematically illustrating main parts of a bending operation mechanism including a bending operation member in the operation section main body in FIG. 9. Note that FIGS. 9 to 11 are illustrated with a part of the operation section main body omitted in order to illustrate an internal mechanism of the operation section.

An endoscope according to the second embodiment of the present disclosure basically has a configuration that is substantially same as the configuration of the aforementioned endoscope according to the first embodiment. In the second embodiment, the bending operation member is configured to have an inclination center O located at a position different from the position in the configuration in the first embodiment. Therefore, same configuration members as the configuration members in the aforementioned first embodiment will be denoted by same reference signs in the following description, and description will be omitted. Also, illustration other than the main parts is omitted to explain the second embodiment. Only configurations that are different from the configurations in the aforementioned first embodiment will be described below in detail.

An operation section 3B of an endoscope according to the second embodiment of the present disclosure includes a bending operation mechanism 30B including a bending operation knob 9B which is a bending operation member and an inclination maintaining mechanism 44.

The bending operation knob 9B is provided in an operation section main body 3Ba of the operation section 3B. The bending operation knob 9B includes a UD bending operation knob 9Ba, an RL bending operation knob 9*b*, an RL bending fixation knob 9*c*, a UD bending fixation lever 9*d*, and a fixed member 9*e*.

Among the components, the RL bending operation knob 9*b*, the RL bending fixation knob 9*c*, and the UD bending fixation lever 9*d* have configurations that are same as the configurations in the aforementioned first embodiment. The UD bending operation knob 9Ba is different from the UD bending operation knob in the aforementioned first embodiment in that the UD bending operation knob 9Ba includes the fixed member 9*e*.

The fixed member 9*e* is a member provided in the UD bending operation knob 9Ba. Not that the fixed member 9*e* is also a member that functions as a part of the inclination maintaining mechanism 44. The fixed member 9*e* is a configuration member with which the fixing base 41 in the aforementioned first embodiment is replaced. A detailed configuration of the fixed member 9*e* will be described later (see FIG. 11).

The bending operation mechanism 30B includes bending wires (31 and 32), a pulley unit 40 including pulleys (33 and 34), rotation shaft members (35 and 36), brake mechanisms (37 and 38), a fixing shaft 39, and the like as illustrated in FIG. 11. Note that the bending operation mechanism 30B includes the bending operation knob 9B which is a bending operation member. A configuration of the bending operation mechanism 30B is substantially the same as the configuration in the aforementioned first embodiment.

The inclination maintaining mechanism 44 is a configuration unit that maintains a center axis Ax of the bending operation knob 9 in a state where the center axis Ax is inclined by a predetermined angle. The inclination maintaining mechanism 44 includes a fixing plate member 42, a fixing screw 43, and the fixed member 9*e* as illustrated in FIGS. 9 and 10.

A first end (proximal end) of the fixed member 9*e* is fixed to an internal fixing section (not illustrated) of the UD bending operation knob 9Ba. In such a case, the fixed member 9*e* has a substantially cylindrical shape. The fixed member 9*e* is disposed with the center axis Ax caused to coincide with the center axis Ax of the UD bending operation knob 9B and extends in a direction along the center axis Ax of the UD bending operation knob 9Ba. Note that a first shaft member (UD) 35B is inserted into the fixed member 9*e* (see FIG. 11).

The fixing plate member 42 is located at the internal fixing section (not illustrated) of the operation section main body 3Ba. The fixing plate member 42 includes at least two plate-shaped members (see FIG. 10). The fixed member 9*e* is disposed to be sandwiched between the two plate-shaped members of the fixing plate member 42. A through-hole 42*a* with a circular shape into which the fixing screw 43 is caused to be inserted is formed in each of the plate-shaped members of the fixing plate member 42.

The fixing screw 43 is a fastening member that includes a male screw section to be screwed into the fixed member 9*e* with the fixing plate member 42 sandwiched. Therefore, a female screw hole section 9*m* (see FIG. 10) is formed at each of positions facing each other with the center axis Ax sandwiched at a predetermined position on the outer circumferential surface of the fixed member 9*e*. Here, the female screw hole section 9*m* is a hole extending in a direction that perpendicularly intersects the center axis Ax of the bending operation knob 9B. Therefore, the fixing screw 43 screwed into and located at the female screw hole section 9*m* is provided to project outward from the outer circumferential surface of the fixed member 9*e* in the direction that perpendicularly intersects the center axis Ax of the bending operation knob 9B.

With such a configuration, the fixing screw 43 is inserted into the through-hole 42*a* in the fixing plate member 42, and the male screw section of the fixing screw 43 is then screwed into and fastened to the female screw hole section 9*m* in the fixed member 9*e* in the inclination maintaining mechanism 44. The inclination angle of the center axis Ax of the bending operation knob 9B is thus maintained at a predetermined angle.

Thus, the inclination maintaining mechanism 44 has a function of supporting the fixing shaft 39 and maintaining the predetermined inclined state. In other words, the inclination maintaining mechanism 44 is provided as a configuration unit with which the fixing base 41 in the aforementioned first embodiment is replaced. The inclined state of the rotation shaft (fixing shaft 39) in such a case is set to have an inclination center O at a predetermined position in the middle of the fixing shaft 39 (the center axis Ax of the bending operation knob).

In other words, the center axis Ax of the bending operation knob 9B is disposed to be inclined with respect to the direction F that is perpendicular to each of the longitudinal direction S of the operation section main body 3Ba and the advancing and retracting direction T when seen from above the operation section 3B in the longitudinal direction S that is same as the aforementioned first embodiment, in the endoscope according to the second embodiment as well.

In other words, the bending operation knob 9B is disposed such that the center axis Ax is inclined with respect to the operation knob end surface E1 where the bending operation knob 9B is located in the operation section main body 3Ba as illustrated in FIG. 9. In such a case, the inclination of the center axis Ax can be substantially the same as the aforementioned first embodiment.

Note that an air feeding/water feeding button 21 and a suction button 22 as switch buttons provided on the outer surface of the operation section main body 3Ba and a plurality of operation members 11 are located similarly to the aforementioned first embodiment.

It is possible to obtain effects and advantages that are same as the effects and advantages of the aforementioned first embodiment in the thus configured endoscope according to the second embodiment of the present disclosure as well.

Third Embodiment

Figure 12:
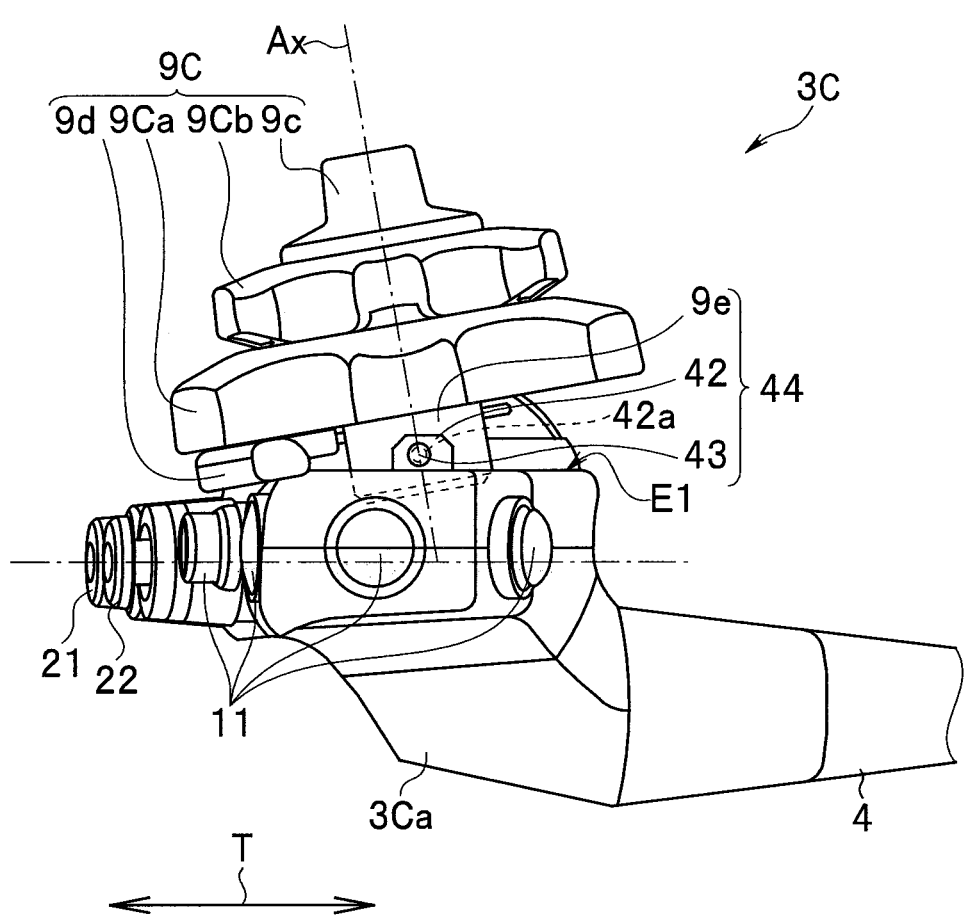
FIG. 12 is a plan view of an operation section main body of an endoscope according to a third embodiment of the present disclosure in a view from above.
Figure 13:
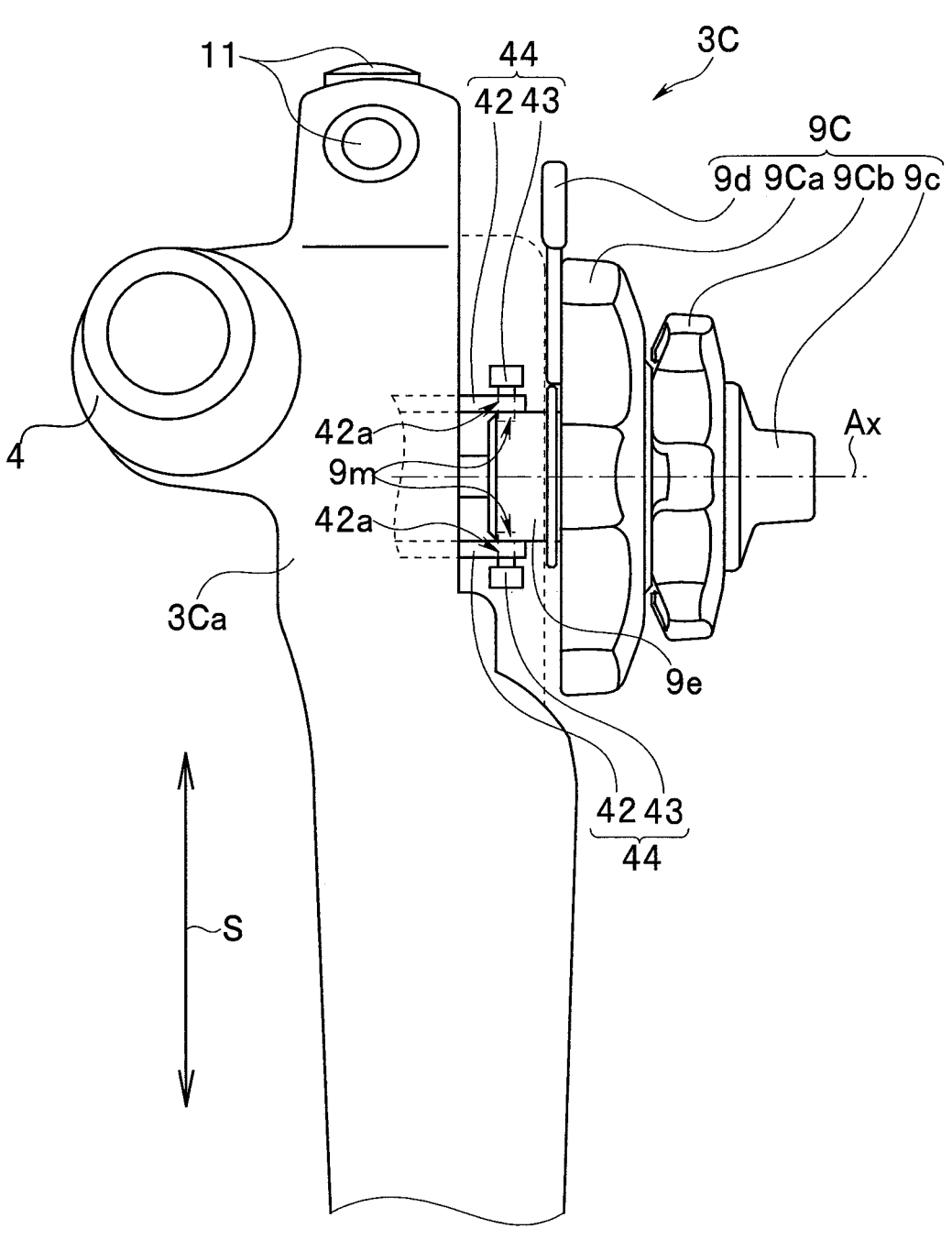
FIG. 13 is a plan view of the operation section main body in FIG. 12 in a view from the back.
Figure 14:
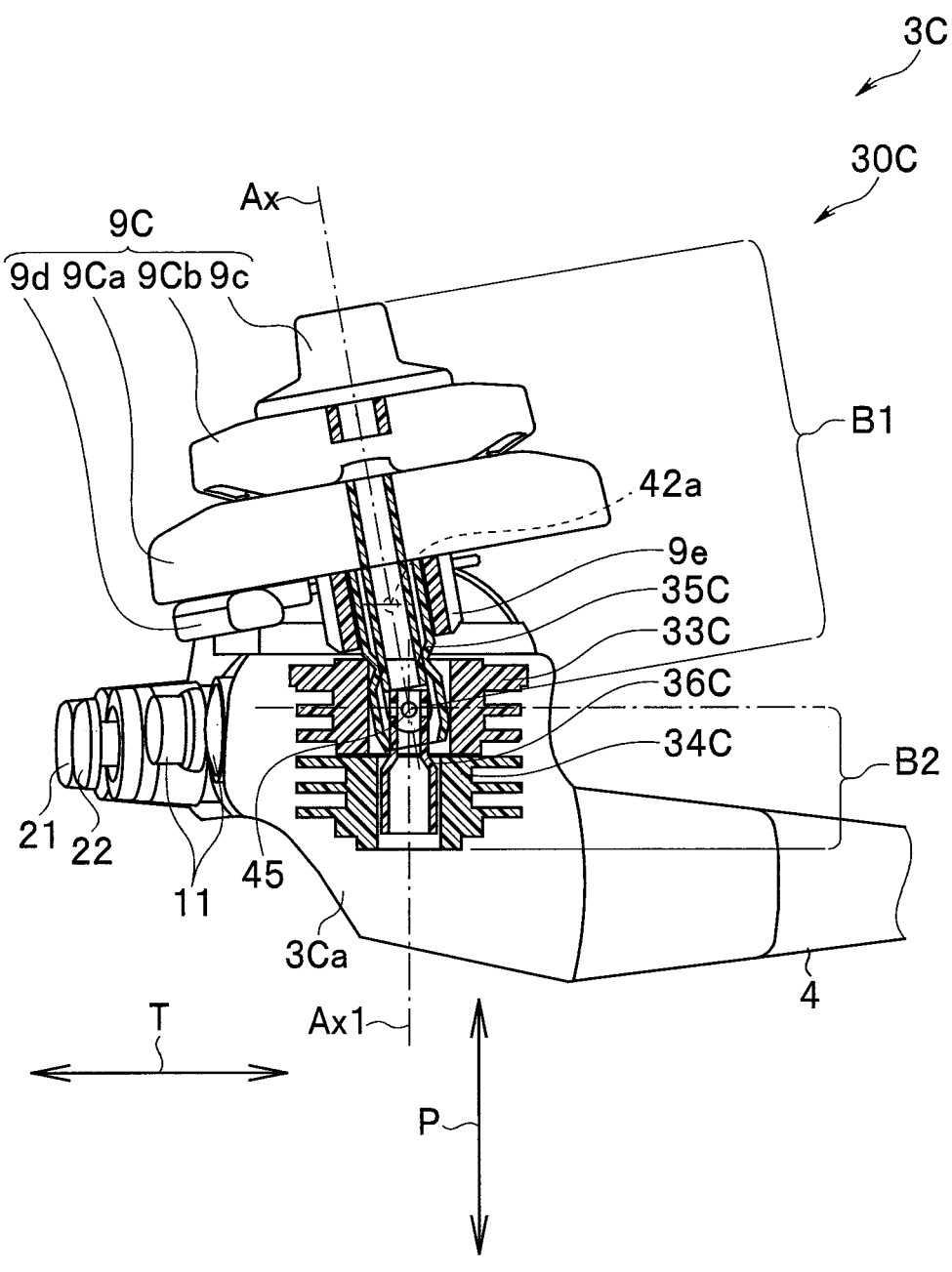
FIG. 14 is a sectional view schematically illustrating main parts of a bending operation mechanism including a bending operation member in FIG. 13.

Next, a third embodiment of the present disclosure will be described. FIGS. 12 to 17 are diagrams illustrating the third embodiment of the present disclosure. Among the drawings, FIG. 12 is a plan view of an operation section main body in a view from above (a diagram corresponding to FIGS. 3 and 9). FIG. 13 is a plan view of the operation section main body in FIG. 12 in a view from the back (corresponding to FIG. 10). FIG. 14 is a sectional view schematically illustrating main parts of a bending operation mechanism including a bending operation member (a diagram corresponding to FIGS. 4 and 11). Note that FIGS. 12 to 14 are illustrated with a part of the operation section main body omitted in order to illustrate an internal mechanism of the operation section.

Figure 15:
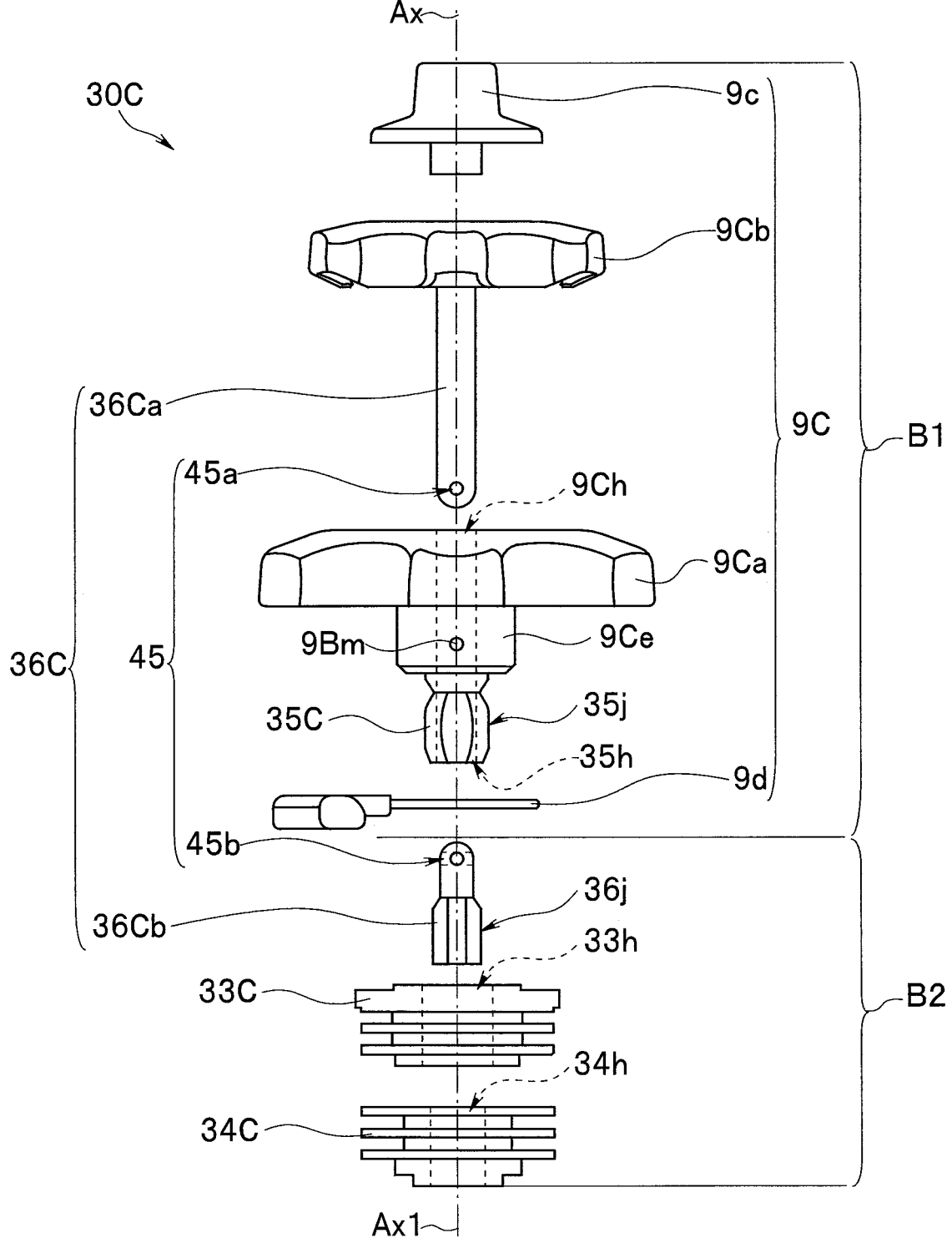
FIG. 15 is an exploded view illustrating main parts of the bending operation mechanism including the bending operation member in FIG. 14.
Figure 16:
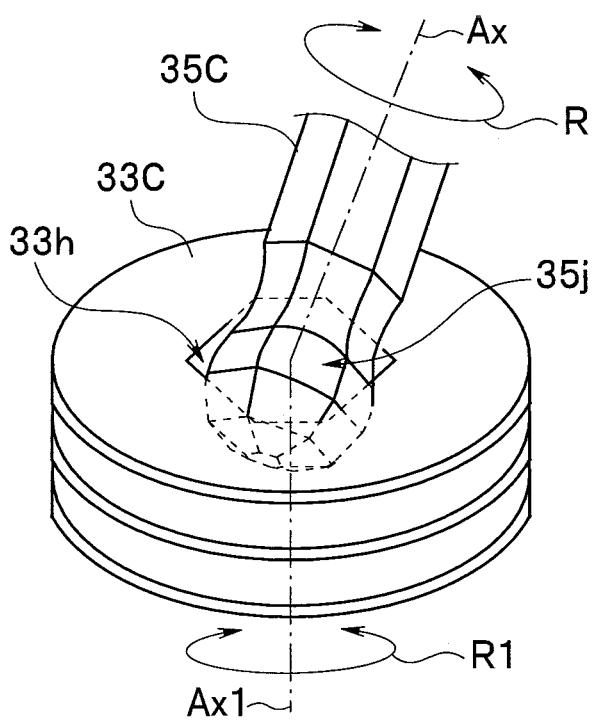
FIG. 16 is a conceptual diagram illustrating a connection part of a first shaft member and a first pulley from among configuration members in FIG. 15 in an enlarged manner.
Figure 17:
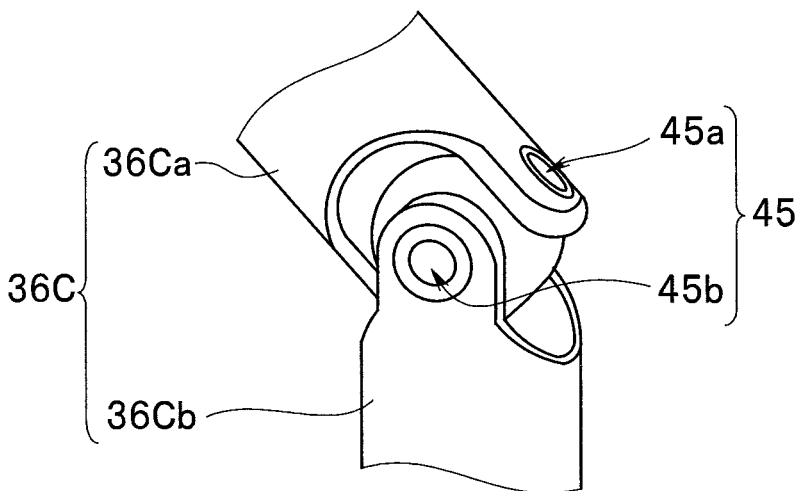
FIG. 17 is a conceptual diagram illustrating a universal joint provided in a second shaft member from among the configuration members in FIG. 15.

FIG. 15 is an exploded view illustrating main parts of the bending operation mechanism including the bending operation member in an exploded manner. FIG. 16 is a diagram conceptually illustrating a connection part between a first shaft member and a first pulley in an enlarged manner. FIG. 17 is a diagram conceptually illustrating a universal joint provided in a second shaft member.

An endoscope according to the third embodiment of the present disclosure basically has a configuration that is substantially same as the configurations of the aforementioned endoscopes according to the first and second embodiments. In the third embodiment, a configuration of the bending operation mechanism including the bending operation member, a configuration of a mechanism that transmits a rotation force of the bending operation member to a pulley is slightly different from the configurations in the first and second embodiments. Therefore, the configuration members that are same as the configuration members in the aforementioned first embodiment will be denoted by same reference signs in the following description, and description will be omitted. Also, illustration other than the main parts is omitted when the third embodiment is explained. Also, only configurations that are different from the configuration in the aforementioned first embodiment will be described below in detail.

An operation section 3C of the endoscope according to the third embodiment of the present disclosure includes a bending operation mechanism 30C (see FIGS. 14 and 15) including a bending operation knob 9C which is a bending operation member.

The bending operation knob 9C is provided in an operation section main body 3Ca of the operation section 3C. The bending operation knob 9C includes a UD bending operation knob 9Ca, an RL bending operation knob 9Cb, an RL bending fixation knob 9c, a UD bending fixation lever 9d, and a fixed member 9e.

Among the components, the RL bending fixation knob 9c, the UD bending fixation lever 9d, and the fixed member 9e have configurations that are same as the configurations in the aforementioned first embodiment. Also, the UD bending operation knob 9Ca is same as the UD bending operation knob in the aforementioned second embodiment in that the UD bending operation knob 9Ca includes the fixed member 9e.

Here, the fixed member 9e has a configuration that is substantially same as the configuration in the aforementioned second embodiment. In other words, the fixed member 9e is a configuration member included in an inclination maintaining mechanism 44 (see FIG. 11). The inclination maintaining mechanism 44 in the third embodiment is in the same form as the form in the aforementioned second embodiment.

The bending operation mechanism 30C (see FIGS. 14 and 15, in particular) are provided inside the operation section main body 3Ca. The bending operation mechanism 30C includes bending wires (not illustrated), a pulley unit including pulleys (33C and 34C), rotation shaft members (35C and 36C), a brake mechanism (not illustrated), and the like. Note that the bending operation mechanism 30C includes the bending operation knob 9C which is a bending operation member.

The pulley is a disc-shaped member around which each bending wire is wound by rotating in conjunction with each of rotation of the UD bending operation knob 9Ca and rotation of the RL bending operation knob 9Cb. The pulleys include a first pulley (UD) 33C and a second pulley (RL) 34C. The first pulley (UD) 33C is connected to the UD bending operation knob 9Ca through the rotation shaft member (35C) and reels in the first bending wire (UD) in conjunction with rotation of the UD bending operation knob 9Ca. The second pulley (RL) 34C is connected to the RL bending operation knob 9Cb through the rotation shaft member (36C) and reels in the second bending wire (RL) in conjunction with rotation of the RL bending operation knob 9Cb.

Note that the first pulley (UD) 33C includes a through-hole 33h (see FIG. 15) penetrating through the center. The through-hole 33h is formed into a shape with a polygonal section such as a hexagonal section with which a hexagon wrench can engage, for example. Also, a distal end 35j of the first shaft member (UD) 35C, which will be described later, engages with the through-hole 33h (see FIG. 16). Here, once the first shaft member (UD) 35C rotates in a direction of an arrow R (see FIG. 16) around a center axis Ax, the first pulley (UD) 33C rotates in a direction of an arrow R1 (see FIG. 16) around a center axis (rotation shaft) Ax1. In such a manner, the first shaft member (UD) 35C transmits a rotation force of the UD bending operation knob 9Ca to the first pulley (UD) 33C. The center axis Ax of the operation knob 9 C is configured to be tilted with respect to the center axis Ax1 of the at least one pulley 33C and/or 34 C.

Also, the second pulley (RL) 34C includes a through-hole 34h (see FIG. 15) penetrating through the center. The through-hole 34h is formed into a shape with a polygonal section such as a hexagonal section with which a hexagon wrench can engage, for example. Also, a distal end 36*j* of a second shaft 36Cb of the second shaft member (RL) 36C, which will be described later, engages with the through-hole 34*h*. In such a manner, the second shaft member (RL) 36C transmits a rotation force of the RL bending operation knob 9Cb to the second pulley (RL) 34C.

Note that the pulley unit including the pulleys (33C and 34C) is fixed to the inside of the operation section main body 3Ca. In such a case, the center axis Ax1 of the pulleys (33C and 34C) is set to be parallel to a direction P (see FIG. 14) that is perpendicular to each of a longitudinal direction S (see FIG. 13) and an advancing and retreating direction T (see FIGS. 12 and 14) of switch buttons as illustrated in FIG. 14.

Each rotation shaft member is a shaft member that is provided between the UD bending operation knob 9Ca or the RL bending operation knob 9Cb and each corresponding pulley (33C or 34C) and transmits each rotation force of the bending operation knob 9C (9Ca and 9Cb) to each pulley (33C or 34C).

Here, the rotation shaft members in the third embodiment of the present disclosure have mechanisms that are freely folded in the middle of the shafts as illustrated in FIG. 14. In other words, the rotation shaft members include the first shaft member (UD) 35C and the second shaft member (RL) 36C.

The first shaft member (UD) 35C is a rotation shaft member that transmits a rotation force of the UD bending operation knob 9Ca to the first pulley (UD) 33C. The first shaft member (UD) 35C has a substantially cylindrical shape and includes a hollow part 35*h* (see FIG. 15). A first end (proximal end) of the first shaft member (UD) 35C is fixed to an internal fixing section (not illustrated) of the UD bending operation knob 9Ca. In such a case, the first shaft member (UD) 35C is disposed with the center axis caused to coincide with the center axis Ax of the UD bending operation knob 9Ca and extends in a direction along the center axis Ax of the UD bending operation knob 9Ca.

The distal end 35*j* which is the second end of the first shaft member (UD) 35C is formed into a so-called ball point shape, for example (see FIG. 15). The distal end 35*j* engages with the through-hole 33*h* (see FIG. 16) of the first pulley (UD) 33C. With such a configuration, the first shaft member (UD) 35C can transmit a rotation force of the UD bending operation knob 9Ca to the first pulley (UD) 33C (see FIG. 16) even in a case where the first shaft member (UD) 35C engages with the through-hole 33*h* of the first pulley (UD) 33C in an inclined state.

The second shaft member (RL) 36C is a rotation shaft member that transmits a rotation force of the RL bending operation knob 9*b* to the second pulley (RL) 34C. The second shaft member (RL) 36C is inserted into a center hole 9Ch (see FIG. 15) of the UD bending operation knob 9Ca and the hollow part 35*h* of the first shaft member (UD) 35C. The second shaft member (RL) 36C includes a first shaft 36Ca, a second shaft 36Cb, and a universal joint 45.

A first end (proximal end) of the first shaft 36Ca is fixed to an internal fixing section (not illustrated) of the RL bending operation knob 9Cb. In such a case, the first shaft 36Ca is disposed with the center axis caused to coincide with the center axis Ax of the RL bending operation knob 9Cb and extends in a direction along the center axis Ax of the RL bending operation knob 9Cb. A first joint section 45*a* (see FIGS. 15 and 17) configuring a part of the universal joint 45 is provided at a second end (distal end) of the first shaft 36Ca.

A second joint section 45*b* (see FIGS. 15 and 17) configuring another part of the universal joint 45 is provided at a first end (proximal end) of the second shaft 36Cb. Also, the distal end 36*j* which is a second end of the second shaft 36Cb is formed into a so-called hexagon wrench shape with a polygonal section, such as a hexagonal prism, for example.

Here, the universal joint 45 is formed by the first joint section 45*a* of the first shaft 36Ca and the second joint section 45*b* of the second shaft 36Cb (see FIG. 17). The universal joint 45 couples the first shaft 36Ca to the second shaft 36Cb and configures the second shaft member (RL) 36C. With such a configuration, the second shaft (RL) 36C is in the form in which the second shaft member (RL) 36C can be coupled to be freely folded at a predetermined midway position (coupled part) and can transmit rotation about the shaft.

In other words, the universal joint 45 is provided in the middle of the second shaft member (RL) 36C that is provided along the center axis Ax of the bending operation knob 9C and the center axis Ax1 of the pulleys and transmits a rotation force of the RL bending operation knob 9Cb to the second pulley (RL) 34C. In such a case, the universal joint 45 is disposed inside the first pulley (UD) 33C when the bending operation mechanism 30C is brought into a state where the bending operation mechanism 30C is incorporated in the operation section main body 3Ca.

Note that in the third embodiment of the present disclosure, a form based on a universal joint scheme is illustrated as a configuration example of the universal joint 45 as illustrated in FIG. 17. However, the form of the universal joint is not limited to the illustrated form. Any form of the universal joint 45 may be employed as long as the shaft members are coupled to be freely folded at an arbitrary midway position and rotation around the shafts can be transmitted in the form. Therefore, another scheme such as a ball joint, for example, can be employed as another form of the universal joint 45.

In such a manner, the distal end 35*j* of the first shaft member (UD) 35C out of the rotation shaft members is formed into a so-called ball point shape in the third embodiment of the present disclosure. The second shaft member (RL) 36C out of the rotation shaft members is configured to be foldable and rotatable at a predetermined position on the shaft, as a configuration including two shaft members (36Ca and 36Cb) and the universal joint 45.

The center axis Ax of the bending operation knob 9C is fixed with a fixing screw 43 in a state where the center axis Ax is disposed to be inclined by a predetermined angle in a predetermined direction with respect to an operation knob end surface E1 of the operation section main body 3Ca similarly as in the aforementioned first and second embodiments. An inclination center O here serves as a folding point of the universal joint 45.

At the same time, the center axis Ax1 of the pulleys (33C and 34C) is disposed to be parallel to a direction P (see FIG. 14) that is perpendicular to each of the longitudinal direction S (see FIG. 13) and the advancing and retreating direction T (see FIG. 12) of the switch buttons as described above.

Therefore, the rotation shaft members include a first region B1 (a region along the center axis Ax; see FIGS. 14 and 15) in which the bending operation knob 9C is axially supported in a rotatable manner and a second region B2 (a region along the center axis Ax1; see FIGS. 14 and 15) in which the pulleys (33C and 34C) are axially supported in a rotatable manner. In such a case, the first region B1 and the second region B2 are coupled in a folded form by the universal joint 45.

It is possible to obtain effects and advantages that are same as the effects and the advantages of the aforementioned first and second embodiments in the third embodiment with such a configuration. In the configuration in the third embodiment, the center axis Ax1 of the pulleys are disposed to perpendicularly intersect the operation knob end surface E1. With such a configuration, it is not necessary to employ disposition in which configuration units including the pulley unit and the following units from among the configuration units disposed inside the operation section main body 3Ca are inclined in the bending operation mechanism 30C. It is thus possible to contribute an improvement in efficiency of the member disposition inside the operation section main body 3Ca.

Third Modification

A modification as will be described below is further conceivable for the endoscope according to the third embodiment of the present disclosure.

As the endoscope in the aforementioned third embodiment, the example in which the through-hole 42a of the fixing plate member 42 is formed as a circular hole that allows the fixing screw 43 to be inserted has been described in regard to the inclination maintaining mechanism 44. However, the configuration of the through-hole 42a is not limited to the configuration example in the aforementioned third embodiment.

Figure 18:
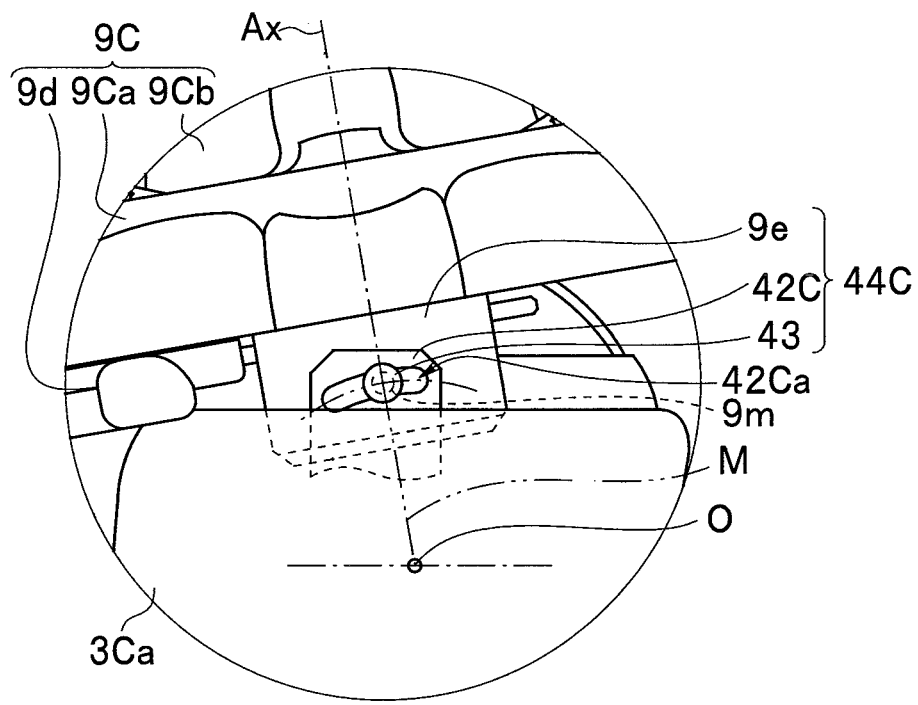
FIG. 18 is a main part enlarged view illustrating a modification (third modification) of an inclination maintaining mechanism in the endoscope in FIG. 1.

For example, FIG. 18 is a main part enlarged view illustrating a modification (third modification) of the inclination maintaining mechanism in the endoscope. Note that illustration of some configuration members is omitted in FIG. 18.

An inclination maintaining mechanism 44C illustrated as a third modification is also equipped with an angle adjustment function with which it is possible to adjust an inclination angle of the center axis Ax of the bending operation knob 9C within a predetermined range in addition to the function of maintaining the inclination angle. Therefore, the inclination maintaining mechanism 44C also functions as an angle adjustment mechanism.

In other words, the inclination maintaining mechanism 44C includes a fixing plate member 42C, a fixing screw 43, and a fixed member 9e as illustrated in FIG. 18. Among the components, only a configuration of the fixing plate member 42C is different from the configuration in the inclination maintaining mechanism 44 in the aforementioned third embodiment.

In the third modification, the fixing plate member 42C includes a penetrating groove 42Ca as a configuration with which the through-hole 42a is replaced. The penetrating groove 42Ca is a penetrating groove with an arc shape provided in the fixing plate member 42C.

Here, the penetrating groove 42Ca is formed along an arc including, as a radius, a virtual line M connecting an inclination center O when the center axis Ax of the bending operation knob 9C is caused to be inclined and a center point of a female screw hole section 9m of the fixed member 9e when a state where the bending operation knob 9C is incorporated in the operation section main body 3Ca is achieved. In such a case, the virtual line M is on a line that coincides with the center axis Ax of the bending operation knob 9C.

In the third modification with such a configuration, the center axis Ax of the bending operation knob 9C is inclined by a predetermined angle in a predetermined direction first in a state where the fixing screw 43 is loosened. Here, the fixing screw 43 moves within a range of the arc length of the penetrating groove 42Ca along the penetrating groove 42Ca as the bending operation knob 9C is inclined.

In other words, a moving direction of the fixing screw 43 is guided by the penetrating groove 42Ca. In other words, the fixing screw 43 functions as a guide member that smoothly guides swinging of the center axis Ax of the bending operation knob 9C by moving along the penetrating groove 42Ca. Here, the penetrating groove 42Ca functions as a guide groove that guides the movement of the fixing screw 43.

In such a case, the inclination range of the center axis Ax of the bending operation knob 9C is defined by the arc length of the penetrating groove 42Ca. In such a manner, the center axis Ax of the bending operation knob 9C is set at a desired angular position.

The center axis Ax of the bending operation knob 9C is set at the desired inclination angle, and the fixing screw 43 is then fastened. In such a case, the fixing screw 43 functions as a holding member that fixes and maintains the center axis Ax of the bending operation knob 9C at the desired inclination angle.

Through such a procedure, the inclination angle of the center axis Ax of the bending operation knob 9C can freely and steplessly be adjusted to the desired angle within a range of the arc length of the penetrating groove 42Ca.

Note that it is possible to arbitrarily set the adjustment range of the inclination angle of the center axis Ax of the bending operation knob 9C by appropriately setting the arc length of the penetrating groove 42Ca.

Also, the configuration of the third modification can be applied to the aforementioned second embodiment as well in a completely same manner.

Fourth Modification

Figure 19:
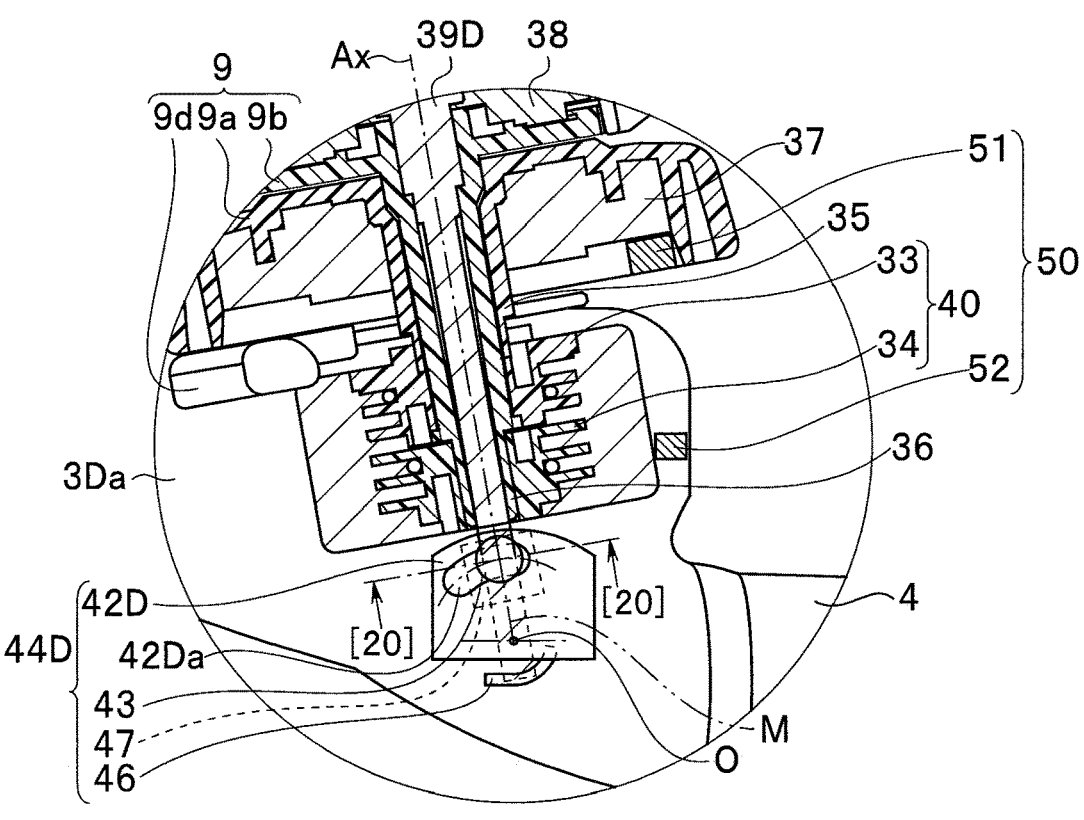
FIG. 19 is a main part enlarged view illustrating another modification (fourth modification) of the inclination maintaining mechanism in the endoscope in FIG. 1 in a view from above the operation section.
Figure 20:
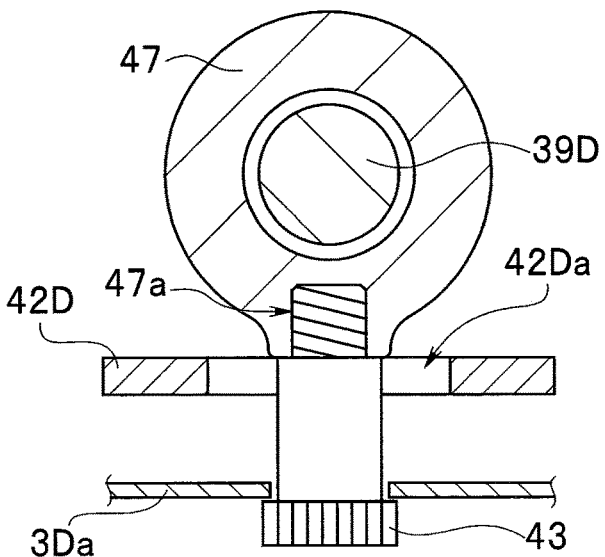
FIG. 20 is a conceptual diagram conceptually illustrating a section along a line [20]-[20] in FIG. 19.

A configuration that is same as the configuration of the inclination maintaining mechanism illustrated in the aforementioned third modification can also be applied to the aforementioned first embodiment. For example, FIGS. 19 and 20 are diagrams illustrating another modification (fourth modification) of the inclination maintaining mechanism in the endoscope. Out of the drawings, FIG. 19 is a main part enlarged view of the inclination maintaining mechanism in the fourth modification in a view from above the operation section (a diagram corresponding to FIGS. 3, 9, and 12). Illustration of some configuration members is omitted in FIG. 19 as well. FIG. 20 is a conceptual diagram illustrating a section along a line [20]-[20] in FIG. 19.

An inclination maintaining mechanism 44D illustrated as the fourth modification is a configuration example in a case where the configuration that is substantially same as the configuration of the inclination maintaining mechanism 44C in the aforementioned third modification is applied to the endoscope (see FIG. 4) in the aforementioned first embodiment. In other words, the inclination maintaining mechanism 44D also has an angle adjustment function in addition to the function of maintaining the inclination angle. Therefore, the inclination maintaining mechanism 44D also functions as the angle adjustment mechanism.

The inclination maintaining mechanism 44D in the fourth modification includes a fixing plate member 42D, a fixing screw 43, a guide rail member 46, and a cover member 47 as illustrated in FIG. 19.

The fixing plate member 42D is located in an internal fixing section (not illustrated) of an operation section main body 3Da. The fixing plate member 42D is disposed to sandwich a vicinity of a distal end of a fixing shaft 39D. Here, the fixing plate member 42D is a member that supports the center axis Ax of the bending operation knob 9C such that the center axis Ax can be inclined in a predetermined direction around a predetermined position as a center, which is an end section of the fixing shaft 39D, on the side (the side of the distal end) where the bending operation knob 9C is not provided. In such a case, the center position at which the center axis Ax of the bending operation knob 9 is caused to be inclined is indicated as an inclination center O.

Note that the fixing plate member 42D may be configured by providing a ball bearing or the like at the inclination center O of the center axis Ax of the bending operation knob 9C. The cover member 47 is provided at a predetermined site in the vicinity of the distal end of the fixing shaft 39D. The cover member 47 is provided as a receiving member for the fixing screw 43, which will be described later.

A penetrating groove 42Da into which the fixing screw 43 is caused to be inserted is formed in the fixing plate member 42D. The penetrating groove 42Da is formed in a substantially same form as the form of the penetrating groove 42Ca in the aforementioned third modification.

The fixing screw 43 that is caused to be inserted into the penetrating groove 42Da is screwed into a female screw hole 47*a* provided in the cover member 47 as illustrated in FIG. 20. In such a case, the cover member 47 functions as a receiving member that receives screw fitting of the fixing screw 43 with the fixing plate member 42D sandwiched.

The guide rail member 46 is a guide member that is disposed to abut a distal end surface of the fixing shaft 39D and smoothly guides swinging of the center axis Ax (fixing shaft 39D), and is also a support member that supports the fixing shaft 39D. Here, the swinging of the center axis Ax is caused around the inclination center O in the vicinity of the distal end of the fixing shaft 39 as a center point.

Note that the fixing screw 43 is located with an operation head section exposed from the outer surface of the operation section main body 3Da as illustrated in FIG. 20. With such a configuration, the user can directly perform a rotating operation on the head section of the fixing screw 43 with fingers.

Furthermore, the inclination maintaining mechanism 44D that also functions as the angle adjustment mechanism may be configured to include inclination amount detection devices 50 including sensors that detect the inclination of the center axis Ax of the bending operation knob 9 in the fourth modification.

The inclination amount detection devices 50 are provided inside the operation section main body 3Da. Specifically, the inclination amount detection devices 50 are provided in the internal fixing section of the operation section main body 3Da and the internal fixing section of the bending operation knob 9.

The inclination amount detection device 50 includes, for example, a magnet 51, a magnetic sensor 52, and the like. A permanent magnet or the like is used as the magnet 51, and the magnet 51 is fixed at a predetermined position inside the UD bending operation knob 9*a*.

The magnetic sensor 52 is an electronic circuit including a sensor element that is configured by using, for example, a hall element or the like. The magnetic sensor 52 detects the inclination of the center axis Ax of the bending operation knob 9 by detecting a magnetic flux density of the magnet 51. The magnetic sensor 52 is fixed at a predetermined position inside the operation section main body 3Da, which is a position that substantially faces the position where the magnet 51 is located.

With such a configuration, the magnetic flux density decreases as the magnet 51 is separated from the magnetic sensor 52 with the inclination of the bending operation knob 9, for example. Thus, the inclination amount detection device 50 detects that the inclination of the bending operation knob 9 has increased.

Similarly, the magnetic flux density increases as the magnet 51 approaches the magnetic sensor 52 with the inclination of the bending operation knob 9, for example. Thus, the inclination amount detection device 50 detects that the inclination of the bending operation knob 9 has decreased.

The inclination amount detection device 50 detects the inclination of the bending operation knob 9 in such a manner. Here, data of the detection results acquired by the inclination amount detection device 50 is outputted to a processor device (not illustrated) to which the endoscope is connected, predetermined data processing is performed by the processor device, and the data is then outputted to a monitor device (not illustrated) in a predetermined display form. In such a manner, the user can easily check the inclination setting state of the bending operation knob 9 by checking the monitor device and can conveniently perform setting.

Note that although the magnet 51 and the magnetic sensor 52 are illustrated as the configuration of the inclination amount detection device 50, the configuration is not limited to the configuration, and a non-contact sensor device in another form may be applied.

The center axis Ax of the bending operation knob 9 (a rotation shaft and a fixing shaft) is caused to swing within the range of the arc length of the penetrating groove 42Da and is set at a desired angle in a state where the fixing screw 43 is loosened first, similarly as in the third modification in the fourth modification with such a configuration as well.

Here, the fixing screw 43 of the rotation shaft (fixing shaft) moves along the penetrating groove 42Da, and the distal end surface smoothly slides along the guide rail member 46. In such a manner, the center axis Ax of the bending operation knob 9 swings within the predetermined range defined by the arc length of the penetrating groove 42Da. After the center axis Ax is set to a desired angle, the fixing screw 43 is fastened. Note that the setting of the desired inclination angle is performed while the display on the monitor device, for example, is checked.

It is thus possible to freely and steplessly set the inclination angle of the center axis Ax of the bending operation knob 9 to a desired angle within the range of the arc length of the penetrating groove 42Da.

Fifth Modification

Figure 21:
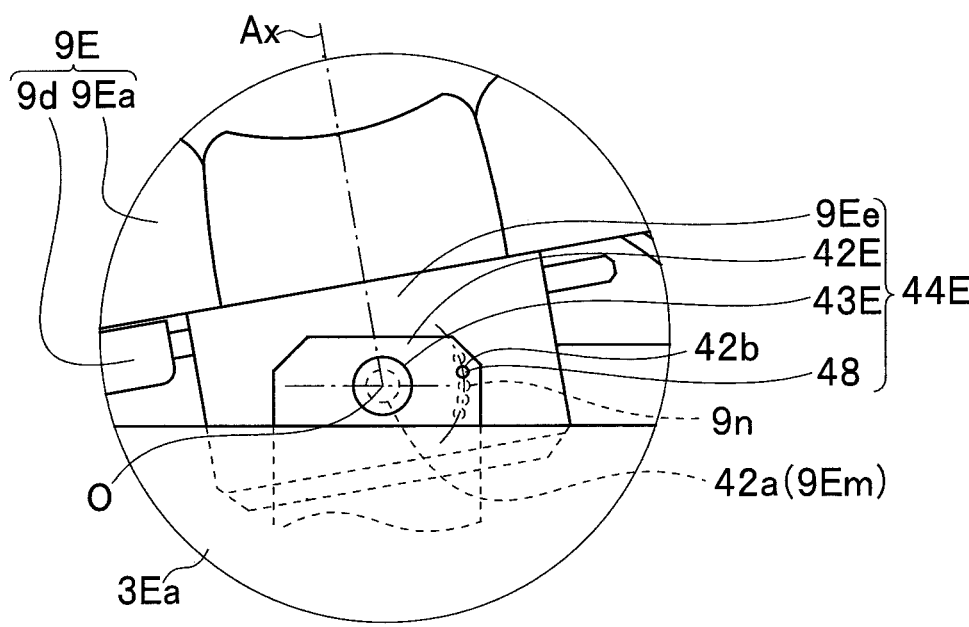
FIG. 21 is a main part enlarged view illustrating another modification (fifth modification) of the inclination maintaining mechanism in the endoscope in FIG. 1.
Figure 22:
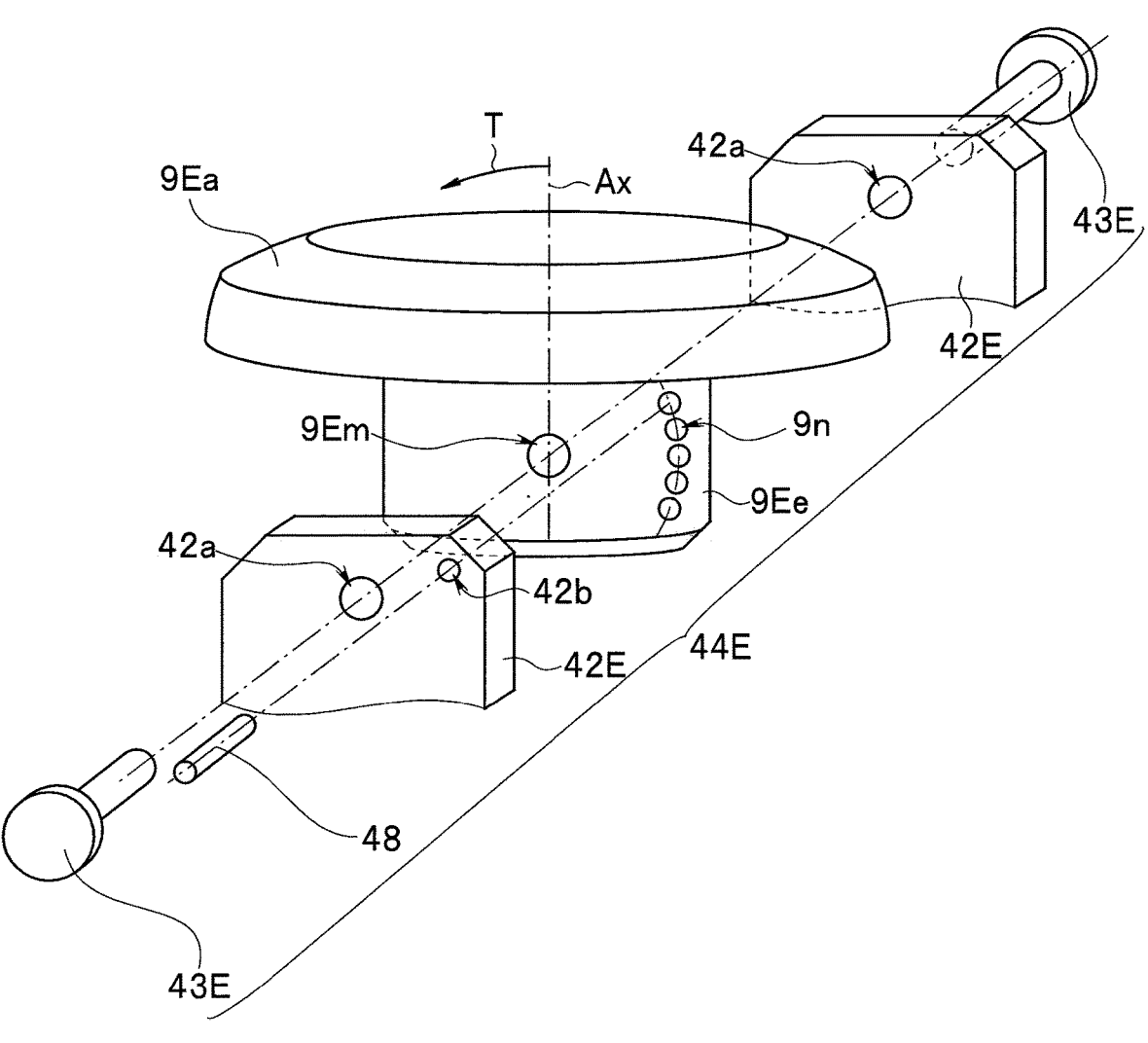
FIG. 22 is a schematic view illustrating main configuration members of the inclination maintaining mechanism according to the fifth modification in FIG. 21.

FIGS. 21 and 22 are diagrams illustrating another modification (fifth modification) of the inclination maintaining mechanism in the endoscope. Out of the drawings, FIG. 21 is a main part enlarged view of the inclination maintaining mechanism in the fifth modification. FIG. 22 is a schematic view illustrating main configuration members of the inclination maintaining mechanism in the fifth modification.

An inclination maintaining mechanism 44E illustrated as the fifth modification is an illustrative example configured by adding a predetermined angle adjustment function to the inclination maintaining mechanism 44 in the aforementioned second embodiment (see FIG. 9).

In the fifth modification, the inclination maintaining mechanism 44E also has an angle adjustment function in addition to the function of maintaining the inclination angle.

Therefore, the inclination maintaining mechanism 44E also functions as an angle adjustment mechanism.

The inclination maintaining mechanism 44E in the fifth modification includes fixing plate members 42E, support shaft pins 43E, a lock pin 48, and a fixed member 9Ee as illustrated in FIGS. 21 and 22.

The fixing plate members 42E are located at an internal fixing section (not illustrated) of an operation section main body 3Ea. Two fixing plate members 42E are disposed to face the center axis Ax with the fixed member 9Ee sandwiched. Here, the fixed member 9Ee is formed integrally with a bending operation knob 9E. Therefore, the fixed member 9Ee rotates in a same direction with a rotating operation of the bending operation knob 9E around the center axis Ax of the bending operation knob 9E.

Through-holes 42a into which the support shaft pins 43E are inserted are formed in a substantially center region in the fixing plate member 42E. The through-holes 42a have a diameter that allows the support shaft pins 43E to be inserted in a loose fit state. In other words, the diameter of the through-holes 42a is larger than the diameter of the support shaft pins 43E.

Note that when the two fixing plate members 42E are disposed at positions where the fixing plate members 42E face each other with the fixed member 9Ee sandwiched, each through-hole 42a is disposed to face each other. The support shaft pins 43E inserted into the respective through-holes 42a are fitted into fitting holes 9Em formed at positions at which the fitting holes 9Em face each other, on the outer circumferential surface of the fixed member 9Ee.

Here, the support shaft pins 43E are pin members configured to have head sections and rod-shaped sections. In such a case, the rod-shaped section is inserted into the through-holes 42a and is fitted to the fitting holes 9Em of the fixed member 9Ee. The head portion restricts a depth of fitting of the support shaft pins 43E into the fitting holes 9Em. Here, the two support shaft pins 43E are disposed on a same axis when the support shaft pins 43E are fitted into the respective fitting holes 9Em.

The bending operation knob 9 is supported to be rotatable about the support shaft pins 43E with the support shaft pins 43E used as rotation shafts, by each support shaft pin 43E being inserted into the through-hole 42a of each fixing plate member 42E and being fitted into the fixing hole 9Em of the fixed member 9Ee.

Also, a second through-hole 42b into which the lock pin 48 is inserted is formed at a predetermined position in the fixing plate member 42E. Note that the second through-hole 42b is provided only predetermined one of the two fixing plate members 42E.

The lock pin 48 after being inserted into the second through-hole 42b is fitted into any one of a plurality of fitting holes 9n formed at facing positions on the outer circumferential surface of the fixed member 9Ee. In other words, the plurality of fitting holes 9n are provided as holes for allowing the lock pin 48 to be inserted through the fixed member 9Ee. The plurality of fitting holes 9n are disposed such that the plurality of fitting holes 9n are aligned at predetermined intervals in the circumferential direction on an arc including, as a center, the inclination center O which is the center point of the through-hole 42a and having a predetermined radius.

Also, when the center axis Ax of the bending operation knob 9E is inclined in the predetermined direction (the direction along a reference sign T in FIG. 22), the lock pin 48 after being inserted into the second through-hole 42b is inserted and fitted into any one of the plurality of fitting holes 9n, and the inclination angle of the bending operation knob 9E is then fixed. Therefore, it is possible to select a desired inclination angle by arbitrarily selecting the fitting hole 9n into which the lock pin 48 is to be fitted. In such a case, it is possible to perform adjustment in a stepwise manner corresponding to the number of the plurality of installed fitting holes 9n.

If the lock pin 48 and the fitting hole 9n are caused to be fitted in the state where the bending operation knob 9E is set to the desired inclination angle, the set inclined state is maintained (locked state). It is possible to release the inclination maintained state merely by pulling the lock pin 48 out of the fitting hole 9n in such a state.

In such a manner, the inclination maintaining mechanism 44E illustrated in the fifth modification functions as the angle adjustment mechanism that can adjust the inclination angle of the bending operation knob 9E in a stepwise manner and also configures a locking release mechanism that switches an inclined state fixed and maintained (locked) state and a fixation released (released) state of the bending operation knob 9E by inserting and pulling out the lock pin 48.

In the thus configured fifth modification, it is possible to adjust the inclination angle of the center axis Ax of the bending operation knob 9E in a stepwise manner to the desired angle within the range of the plurality of fitting holes 9n.

Sixth Modification

Figure 23:
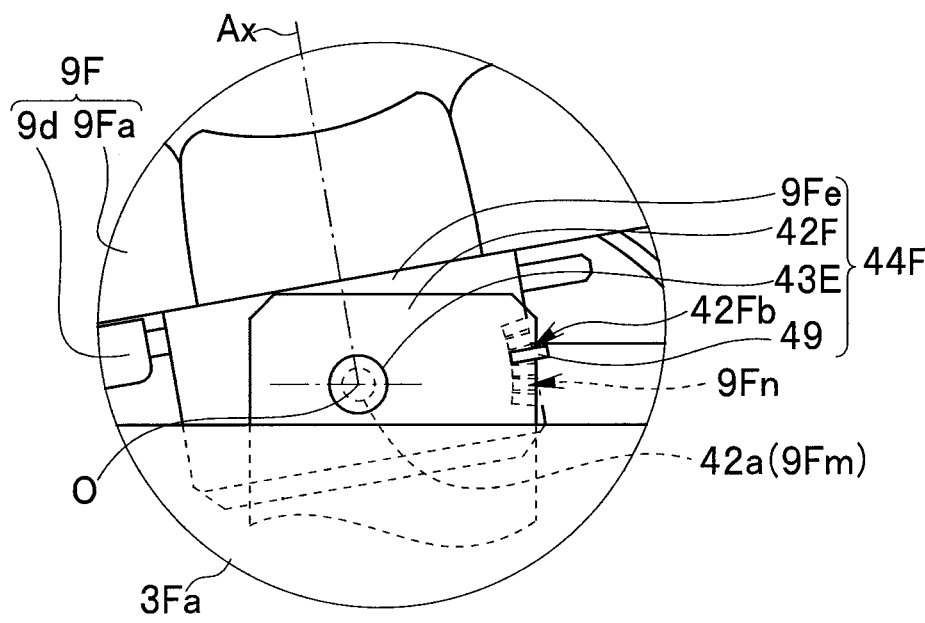
FIG. 23 is a main part enlarged view illustrating a different modification (sixth modification) of the inclination maintaining mechanism in the endoscope in FIG. 1.
Figure 24:
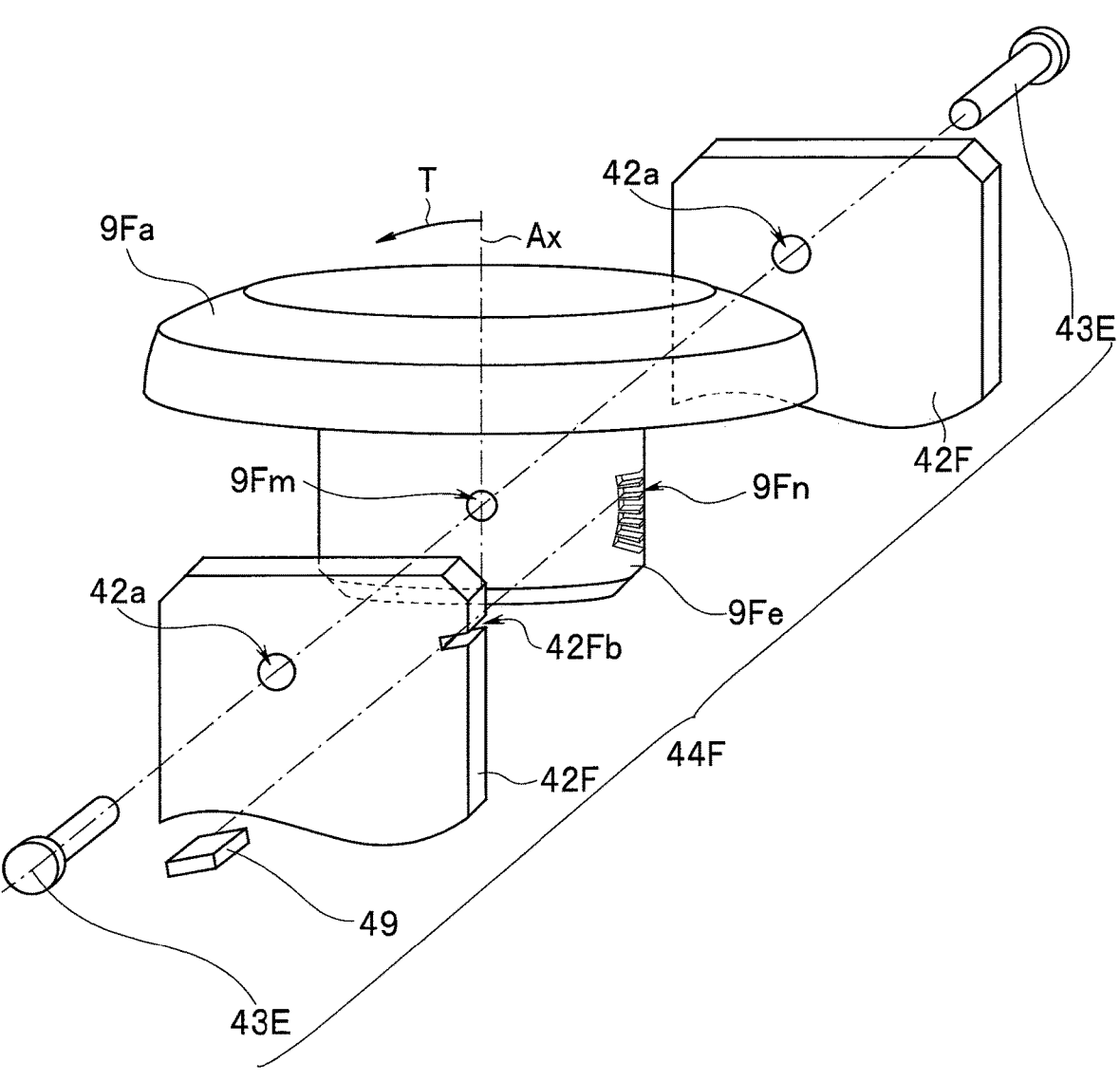
FIG. 24 is a schematic view illustrating main configuration members of the inclination maintaining mechanism according to the sixth modification in FIG. 23.

FIGS. 23 and 24 are diagrams illustrating a different modification (sixth modification) of the inclination maintaining mechanism in the endoscope. Out of the drawings, FIG. 23 is a main part enlarged view of the inclination maintaining mechanism in the sixth modification. FIG. 24 is a schematic view illustrating main configuration members of the inclination maintaining mechanism in the sixth modification.

An inclination maintaining mechanism 44F illustrated as a sixth modification is another illustrative example configured by adding a predetermined angle adjustment function to the inclination maintaining mechanism 44 in the aforementioned second embodiment (see FIG. 9). In other words, the configuration of the sixth modification is basically the same as the configuration of the aforementioned fifth modification.

The sixth modification is same as the fifth modification in that the inclination maintaining mechanism 44F also has an angle adjustment function in addition to the function of maintaining the inclination angle. Therefore, the inclination maintaining mechanism 44F also functions as an angle adjustment mechanism in the sixth modification. In the sixth modification, the configuration of the angle adjustment function is slightly different.

The inclination maintaining mechanism 44F in the sixth modification includes fixing plate members 42F, a support shaft pin 43E, a lock key 49, and a fixed member 9Fe as illustrated in FIGS. 23 and 24.

A key groove 42Fb into which the lock key 49 is caused to be inserted is formed at a predetermined position in the peripheral portion of the fixing plate member 42F. Note that the key groove 42Fb is provided in predetermined one of the two fixing plate members 42F.

The lock key 49 after being inserted into the key groove 42Fb is fitted into any one of a plurality of fitting key grooves 9Fn formed at facing positions in the outer circumferential surface of the fixed member 9Fe. In other words, the plurality of fitting key grooves 9Fn are provided as key grooves for inserting the lock key 49 into and pulling out the lock key 49 from the fixed member 9Fe. The plurality of fitting key grooves 9Fn are disposed such that the plurality of fitting key grooves 9Fn are aligned at predetermined intervals in the circumferential direction on an arc including, as a center, the inclination center O which is the center point of the through-hole 42*a* and having a predetermined radius.

When the center axis Ax of the bending operation knob 9F is caused to be inclined in the predetermined direction (the direction along a reference sign T in FIG. 24), the lock key 49 after being caused to be inserted into the key groove 42Fb is inserted and fitted into any one of the plurality of fitting key grooves 9Fn, and the desired inclination angle of the bending operation knob 9F is thus fixed. Therefore, it is possible to select a desired inclination angle by arbitrarily selecting the fitting key groove 9Fn into which the lock key 49 is to be fitted. In such a case, it is possible to perform adjustment in a stepwise manner corresponding to the number of the plurality of installed fitting key grooves 9Fn.

If the locking key 49 and the fitting key groove 9Fn are caused to be fitted in the state where the bending operation knob 9F is set at the desired inclination angle, the set inclined state is maintained (locked state). It is possible to release the inclination maintained state merely by pulling out the lock key 49 out of the fitting key groove 9Fn in the state.

In such a manner, the inclination maintaining mechanism 44F illustrated in the sixth modification functions as the angle adjustment mechanism that can adjust the inclination angle of the bending operation knob 9F in a stepwise manner and also configures a locking release mechanism that switches the inclined state fixed and maintained (locked) state and the fixation released (released) state of the bending operation knob 9F by inserting and pulling out the lock key 49.

In the thus configured sixth modification, it is possible to adjust the inclination angle of the center axis Ax of the bending operation knob 9F in a stepwise manner to a desired angle within the range of the plurality of fitting key grooves 9Fn.

Seventh Modification

Figure 25:
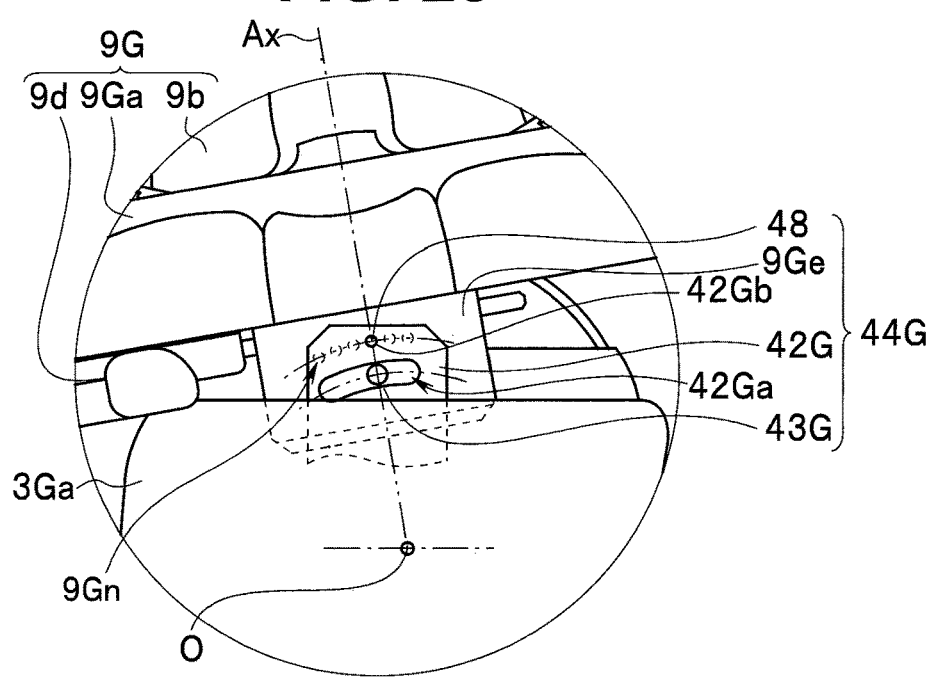
FIG. 25 is a main part enlarged view of an inclination maintaining mechanism according to a yet different modification (seventh modification) of the inclination maintaining mechanism in the endoscope in FIG. 1.
Figure 26:
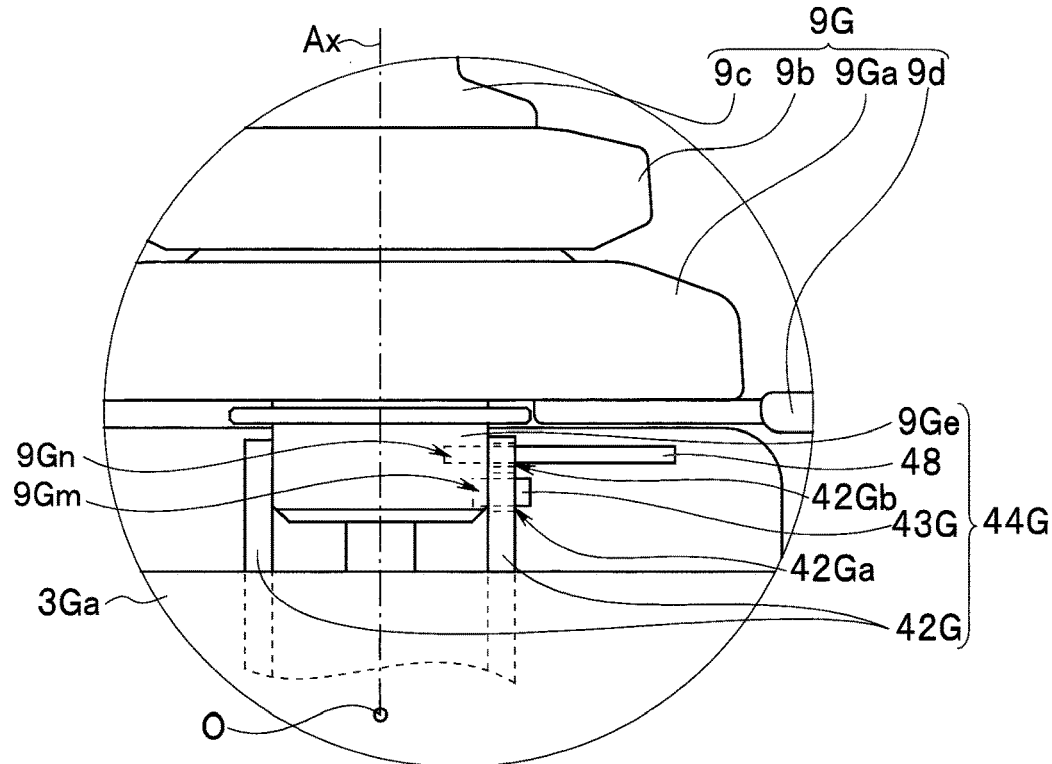
FIG. 26 is a main part enlarged view of the inclination maintaining mechanism according to the seventh modification in FIG. 25 in a view from behind the operation section.

FIGS. 25 and 26 are diagrams illustrating a yet different modification (seventh modification) of the inclination maintaining mechanism in the endoscope. Out of the drawings, FIG. 25 is a main part enlarged view of the inclination maintaining mechanism in the seventh modification. FIG. 26 is a main part enlarged view of the inclination maintaining mechanism in the seventh modification in a view from behind the operation section.

An inclination maintaining mechanism 44G illustrated as the seventh modification is an illustrative example configured by adding a predetermined angle adjustment function to the inclination maintaining mechanism 44C in the aforementioned third modification (see FIG. 18 and the like).

In the seventh modification, the inclination maintaining mechanism 44G has substantially a same configuration as the configuration of the aforementioned third modification, and details are slightly different. In other words, the seventh modification is slightly different from the configuration of the third modification in that adjustment is performed in a stepwise manner by the angle adjustment function.

The inclination maintaining mechanism 44G in the seventh modification includes fixing plate members 42G, a guide pin 43G, a lock pin 48, and a fixed member 9Ge as illustrated in FIGS. 25 and 26.

The fixing plate members 42G are located in an internal fixing section (not illustrated) of an operation section main body 3Ga. Two fixing plate members 42G are disposed to face each other to sandwich the fixed member 9Ge. Here, the fixed member 9Ge is formed integrally with the bending operation knob 9G. Therefore, the fixed member 9Ge rotates in a same direction with a rotating operation of the bending operation knob 9G around the center axis Ax of the bending operation knob 9G.

A penetrating groove 42Ga into which the guide pin 43G is caused to be inserted is formed in at least one of the two fixing plate members 42G. The penetrating groove 42Ga is a guide groove section formed in the form that is substantially same as the form in the aforementioned third embodiment. The guide pin 43G instead of the fixing screw 43 in the aforementioned third modification is inserted into the penetrating groove 42Ga. Therefore, the penetrating groove 42Ga has a diameter that allows the guide pin 43G to be inserted in a loose fit state. In other words, a width dimension of the penetrating groove 42Ga is formed to be slightly wider than a diameter of the guide pin 43G.

Also, the penetrating groove 42Ga is formed along an arc including, as a center, the inclination center O of the center axis Ax of the bending operation knob 9G, having a predetermined radius, and having a predetermined center angle. The guide pin 43G is inserted into the penetrating groove 42Ga. The guide pin 43G is fitted into a fitting hole 9Gm formed in an outer surface of the fixed member 9Ge. Here, the guide pin 43G is fixed to project outward from the outer circumferential surface of the fixed member 9Ge in a direction that perpendicularly intersects the center axis Ax of the bending operation knob 9G. The guide pin 43G is inserted into the penetrating groove 42Ga.

With such a configuration, once the bending operation knob 9G is inclined, the guide pin 43G rotates about the inclination center O. Here, the guide pin 43G moves along the penetrating groove 42Ga. In other words, the penetrating groove 42Ga functions as a guide section that guides the movement of the guide pin 42G moving with the inclination of the bending operation knob 9G.

Also, an angle adjustment pin hole 42Gb is formed in the fixing plate member 42G. The angle adjustment pin hole 42Gb is a through-hole provided at a predetermined position in a region on a side closer to the outer periphery than the arc forming the through-hole 42Ga.

Also, a plurality of pin holes 9Gn are formed at positions facing the angle adjustment pin hole 42Gb in the fixed member 9Ge. Here, the plurality of pin holes 9Gn are formed at predetermined intervals in the radial direction along an arc when the arc with a slightly larger radius than the arc forming the penetrating groove 42Ga is assumed.

When the bending operation knob 9G is incorporated in the operation section main body 3Ga and the bending operation knob 9G is inclined, any one of the plurality of pin holes 9Gn is disposed at a position that the angle adjustment pin hole 42Gb faces.

In the thus configured seventh modification, the lock pin 48 inserted into the angle adjustment pin hole 42Gb is caused to be inserted into any one of the plurality of pin holes 9Gn. In such a manner, the lock pin 48 is set such that the inclination angle of the center axis Ax of the bending operation knob 9G becomes a desired angle. At the same time, the lock pin 48 maintains and fixes the inclined state of the bending operation knob 9G at the set inclination angle position.

Therefore, it is possible to perform the setting of the inclination angle of the center axis Ax of the bending operation knob 9G and the fixing and maintaining of the inclined state of the bending operation knob 9G at the same time merely by inserting and pulling out the lock pin 48 without screw fastening.

Note that in the configuration of the seventh modification, a so-called click stop mechanism may be configured as the configuration including the angle adjustment pin hole 42Gb, the lock pin 48, and the plurality of pin holes 9Gn.

For example, the angle adjustment pin hole (42Gb) is formed as a bottomed hole with an opening directed to the disposition surface of the pin holes 9Gn. A ball member biased in a projecting direction with respect to the opening by an elastic member is accommodated inside the angle adjustment pin hole. In such a case, the opening of the angle adjustment pin hole has a smaller diameter than a diameter of the ball member. In such a manner, the ball member stays inside the angle adjustment pin hole without sticking out from the opening of the angle adjustment pin hole.

Also, the ball member is pushed back to the inside of the angle adjustment pin hole against the elastic member if an external force is applied. Therefore, the ball member freely projects and is freely dented with respect to the opening of the angle adjustment pin hole.

With such a configuration, once the fixed member 9Ge swings in response to the inclination of the bending operation knob 9G, the ball member is fitted into one of the plurality of pin holes 9Gn, and the position is maintained. Therefore, the inclination angle of the bending operation knob 9G is fixed and maintained at a predetermined angle.

Also, if an external force is applied in a direction in which the bending operation knob 9G is caused to be inclined, the ball member is fitted into an adjacent pin hole 9Gn, and a different inclination angle of the bending operation knob 9G can be set by the click stop mechanism.

Eighth Modification

Figure 27:
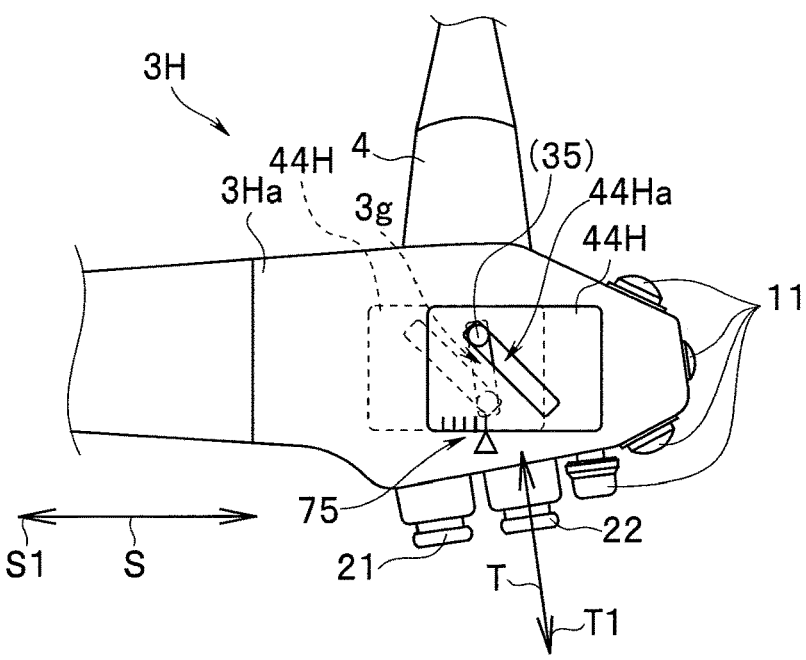
FIG. 27 is a main part enlarged view illustrating a still yet different modification (eighth modification) of the inclination maintaining mechanism in the endoscope in FIG. 1.

FIG. 27 is a diagram illustrating a still yet different modification (eighth modification) of the inclination maintaining mechanism in the endoscope. Here, FIG. 27 is a main part enlarged view of the inclination maintaining mechanism in the eighth modification. Note that the configuration members such as the bending operation knob are omitted and only main parts of the inclination maintaining mechanism are illustrated in FIG. 27.

As illustrated in FIG. 27, a main body guide long hole 3g is formed in a side surface (a surface on the side where the bending operation knob (not illustrated) is provided) of an operation section main body 3Ha of an operation section 3H. The main body guide long hole 3g is formed to extend in a direction that intersects the longitudinal direction S of the operation section 3H, which is a direction parallel to the advancing and retreating direction T of the switch buttons.

Also, a rotation shaft member 35 that is located along the center axis of the bending operation knob (not illustrated) is inserted into the main body guide long hole 3g. Therefore, the main body guide long hole 3g thus performs guiding such that a center shaft member rotating about the center axis of the bending operation knob (not illustrated) as a rotation center moves only in a predetermined direction (the direction that intersects the longitudinal direction S and is parallel to the advancing and retreating direction T of the switch buttons).

Also, an inclination axis guide member 44H that is the inclination maintaining mechanism illustrated as the eighth modification and also functions as an angle adjustment mechanism is provided at a position covering the main body guide long hole 3g in the operation section main body 3Ha. The inclination axis guide member 44H is a flat plate-shaped member as a whole and includes a moving mechanism (not illustrated) that can cause movement within a predetermined range in a predetermined direction. Here, the predetermined direction is a direction that is parallel to the longitudinal direction S of the operation section 3H. Also, a ratchet mechanism that includes a ratchet member capable of causing intermittent sliding within a predetermined range in a predetermined direction (the direction that follows the longitudinal direction S) and stopping, a click stop mechanism, or the like is applied as the moving mechanism of the inclination axis guide member 44H, for example.

The inclination axis guide member 44H includes a guide long hole 44 Ha that intersects the main body guide long hole 3g at a predetermined angle. In such a case, the guide long hole 44Ha and the main body guide long hole 3g intersect each other at an acute angle in the direction in which the switch buttons are located. The rotation shaft member (35) of the bending operation knob (not illustrated) inserted into the main body guide long hole 3g and projecting outward is inserted into the guide long hole 44Ha.

In the thus configured eighth modification, it is assumed that when the inclination axis guide member 44H is located at the position indicated by a solid line in FIG. 27, for example, the rotation shaft member (35) is in a substantially upright state with respect to an outer surface of the operation section main body 3Ha.

If the inclination axis guide member 44H is caused to slide and move in a direction of an arrow S1 in FIG. 27 from the state, then the rotation shaft member (35) is inclined in a direction of an arrow T1 in FIG. 27, which is the advancing and retreating direction T of the switch buttons, while being guided by the main body guide long hole 3g and the guide long hole 44Ha.

The stop position of the inclination axis guide member 44H is maintained in a stepwise manner by the ratchet mechanism or the click stop mechanism. Therefore, the sliding movement is caused to stop when the inclination axis guide member 44H is disposed in the vicinity of a desired position. Then, the inclination axis guide member 44H stops at a predetermined position defined by the ratchet mechanism or the click stop mechanism. The inclination axis guide member 44H maintains the position. The bending operation knob is thus maintained in a predetermined inclined state (or predetermined tilted state).

Note that an index and graduation 75 indicating the stop position of the inclination axis guide member 44H in the sliding direction are provided in the operation section main body 3Ha and the inclination axis guide member 44H. The user can easily check the inclination set state of the bending operation knob by checking the index and the graduation 75.

According to the inclination axis guide member 44H in the eighth modification, it is thus possible to realize a mechanism that has both the inclination maintaining function and the angle adjustment function with a simpler configuration.

Ninth Modification

Figure 28:
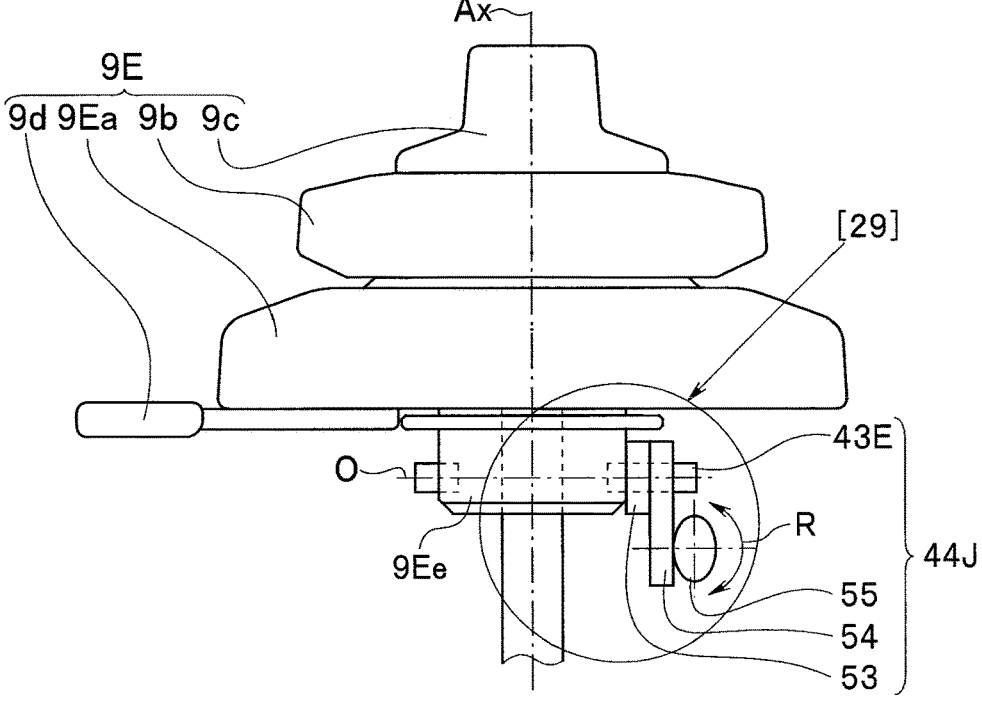
FIG. 28 is a conceptual diagram illustrating yet another modification (ninth modification) of the inclination maintaining mechanism in the endoscope in FIG. 1.
Figure 29:
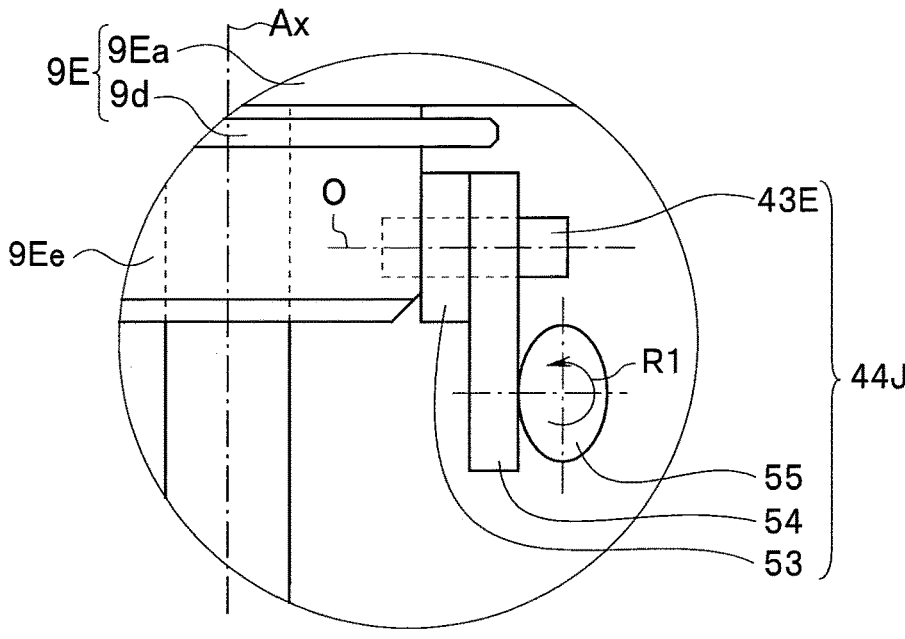
FIG. 29 is a main part enlarged view (released state) illustrating a range indicated by a reference sign [29] in FIG. 28 in an enlarged manner.
Figure 30:
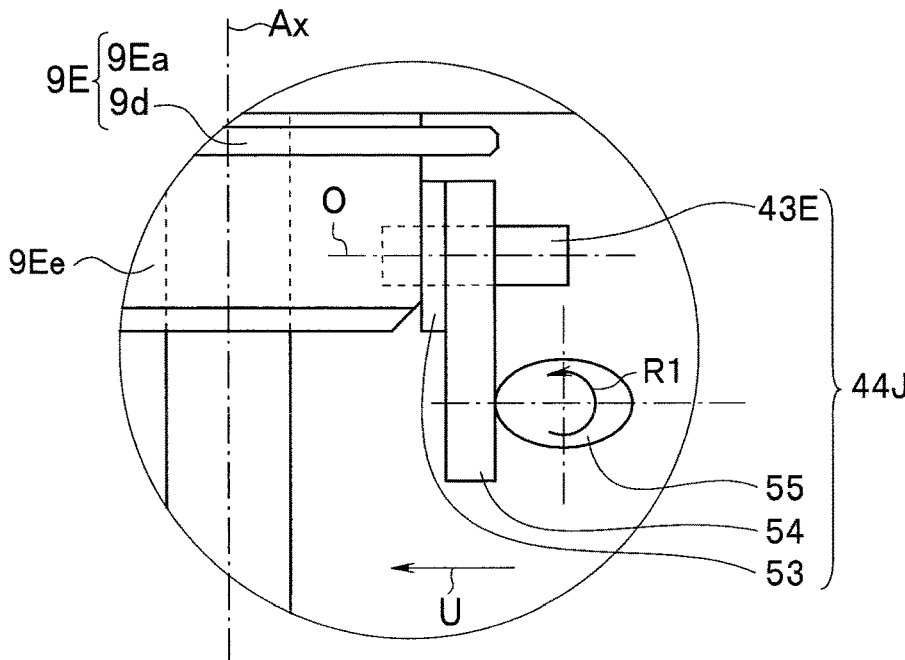
FIG. 30 is a main part enlarged view (fixed state) illustrating the range indicated by the reference sign [29] in FIG. 28 in an enlarged manner.

FIGS. 28 to 30 are diagrams illustrating a yet another modification (ninth modification) of the inclination maintaining mechanism in the endoscope. Among the drawings, FIG. 28 is a conceptual diagram of the inclination maintaining mechanism in the ninth modification. FIGS. 29 and 30 are main part enlarged views illustrating a range indicated by a reference sign [29] in FIG. 28 in an enlarged manner.

Note that FIGS. 29 and 30 illustrate effects of the ninth modification. In other words, FIG. 29 illustrates a released state and FIG. 30 illustrates a fixed state of the inclination maintaining mechanism. FIGS. 28 to 30 conceptually illustrate only main configuration members in order to avoid complication of the drawings.

A basic configuration of the ninth modification is substantially same as the forms illustrated in the aforementioned fifth and sixth modifications (the forms in which the inclination center O is included in the fixed member 9Ee; see FIGS. 21 to 24). Therefore, the same configuration members as the configuration members in the aforementioned fifth and sixth modifications will be denoted by same reference signs, and the following description will be given.

An inclination maintaining mechanism 44J illustrated in the ninth modification has a configuration with which it is possible to perform maintaining and releasing of the inclined state of the center axis Ax of the bending operation knob 9E by increasing and decreasing a pressure to be applied to the fixed member 9Ee.

The inclination maintaining mechanism 44J illustrated as the ninth modification is an angle fixing mechanism configured to include a support shaft pin 43E, a pressure welding part 53, a pressure transmission part 54, a pressure generating part 55, and the like. The angle fixing mechanism configured to fix the operation knob 9 at a predetermined angle.

The support shaft pin 43E is a shaft member that rotatably supports the fixed member 9Ee. The pressure welding part 53 is a flexible part that is made of a material with elasticity such as a rubber part, for example, and applies a pressure to the fixed member 9Ee while protecting the fixed member 9Ee by being deformed by receiving the applied pressure.

The pressure transmission part 54 is a rigid part that receives the applied pressure and efficiently transmits the pressure to the pressure welding part 53. The pressure generating part 55 is a part that generates a predetermined pressing force by coming into contact with and pressing the pressure transmission part 54 and releases the pressing force by being separated from the pressure transmission part 54 and releasing the contact.

The pressure generating part 55 is configured by employing a cam mechanism in the configuration of the ninth modification illustrated in FIG. 28. The cam of the pressure generating part 55 rotates in a direction of an arrow R in FIG. 28. Therefore, when the cam of the pressure generating part 55 is in the state illustrated in FIGS. 28 and 29, the pressure generating part 55 is not generating a pressing force, and the pressure generating part 55 is not pressing the pressure transmission part 54 and the pressure welding part 53. Therefore, the bending operation knob 9E is rotatable about the support shaft pin 43E here. In other words, the bending operation knob 9E is in a state where the bending operation knob 9E can be freely inclined within the predetermined range here.

Here, the center axis Ax of the bending operation knob 9E is brought into a predetermined inclined state. The pressure generating part 55 is caused to rotate in a direction of an arrow R1 in FIG. 29 while the state is maintained. Then, the pressure generating part 55 presses the pressure transmission part 54. In such a manner, the pressure transmission part 54 moves in a direction of an arrow U in FIG. 30. Here, the pressure transmission part 54 applies a pressure to the pressure welding part 53 by the pressure transmission part 54 moving in a direction of an arrow U.

The pressure welding part 53 receives the pressing force caused by the pressure transmission part 54, is compressed, and comes into contact with and applies a pressure to the outer circumferential surface of the fixed member 9Ee. The inclination maintaining mechanism 44J is brought into the state illustrated in FIG. 30. Rotation of the fixed member 9Ee around the inclination center O is thus restricted, and the fixed member 9Ee is brought into a fixed state. Therefore, the inclined state of the bending operation knob 9E is maintained here.

On the other hand, if the pressure generating part 55 is returned to the state in FIG. 29 by causing the pressure generating part 55 to further rotate in the direction of the arrow R1 or by causing the pressure generating part 55 to rotate in a direction opposite to the direction of the arrow R1 in the state illustrated in FIG. 30, the pressing force of the pressure transmission part 54 caused by the pressure generating part 55 is released. Then, the pressure transmission part 54 moves in a direction away from the fixed member 9Ee. The pressure applied to the pressure welding part 53 is thus released. The compressed state of the pressure welding part 53 is also thus released. The state achieved here is the released state of the inclination maintaining mechanism 44J.

According to the ninth modification, the inclination maintaining mechanism 44J that is also an angle adjustment mechanism thus applies the pressure or releases the applied pressure by bringing the pressure welding part 53 into contact with the fixed member 9Ee or separating the pressure welding part 53 from the fixed member 9Ee. The inclination maintaining mechanism 44J can thus fix and maintain the inclined state of the center axis Ax of the bending operation knob 9E or release the fixed state.

Note that as a mechanism for bringing the pressure welding part 53 into contact with the fixed member 9Ee or separating the pressure welding part 53 from the fixed member 9Ee, various forms such as a form in which a screw mechanism illustrated in an eleventh modification (see FIGS. 33 and 34), which will be described later, is employed in addition to the cam mechanism (see FIGS. 28 to 30) illustrated in the aforementioned ninth modification and another cam mechanism illustrated in the next tenth modification (see FIGS. 31 and 32), for example, are conceivable.

Tenth Modification

Figure 31:
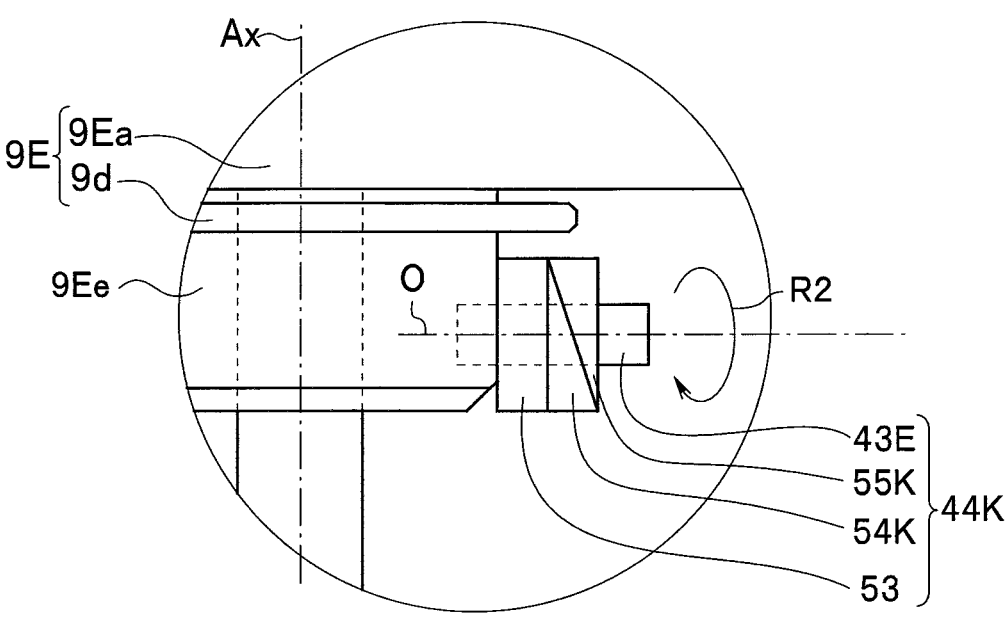
FIG. 31 is a conceptual diagram (released state) illustrating still yet another different modification (tenth modification) of the inclination maintaining mechanism in the endoscope in FIG. 1.
Figure 32:
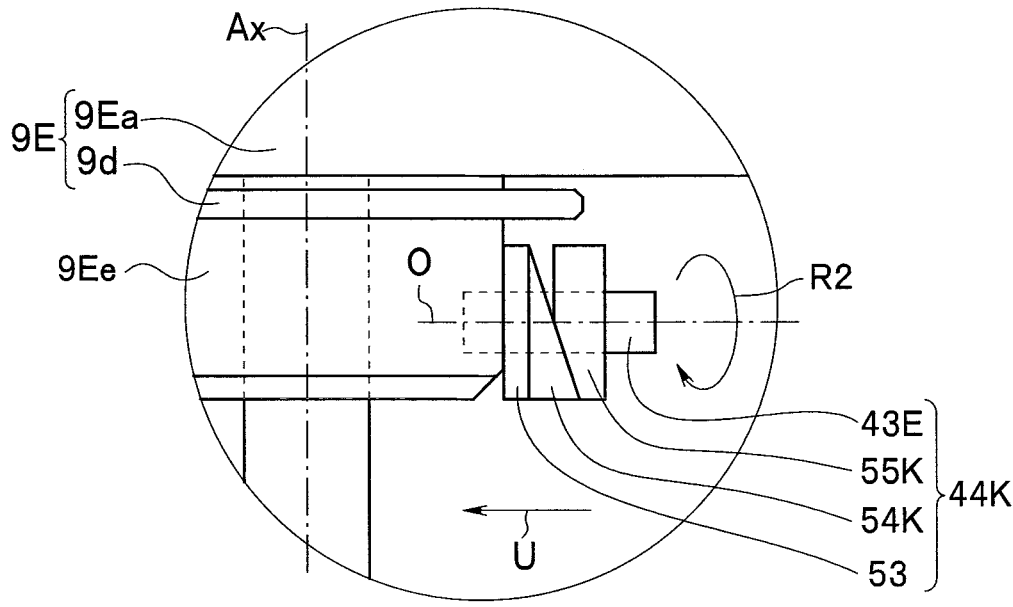
FIG. 32 is a conceptual diagram illustrating a fixed state of the inclination maintaining mechanism in FIG. 31.

FIGS. 31 and 32 are main part enlarged views conceptually illustrating still yet another different modification (tenth modification) of the inclination maintaining mechanism in the endoscope. Out of the drawings, FIG. 31 illustrates a released state and FIG. 32 illustrates a fixed state of the inclination maintaining mechanism. Note that FIGS. 31 and 32 conceptually illustrate only main configuration members in order to avoid complication of the drawings.

A basic configuration of the tenth modification is substantially same as the configuration in the form (see FIGS. 28 to 30) illustrated in the aforementioned ninth modification.

An inclination maintaining mechanism 44K illustrated in the tenth modification is same as the inclination maintaining mechanism in the ninth modification in that the inclination maintaining mechanism 44K has a configuration with which it is possible to maintain and release the inclined state of the center axis Ax of the bending operation knob 9E with the pressure to be applied to the fixed member 9Ee.

The inclination maintaining mechanism 44K illustrated as the tenth modification is an angle fixing mechanism configured to include a support shaft pin 43E, a pressure welding part 53, a pressure transmission part 54K, a pressure generating part 55K, and the like.

The support shaft pin 43E and the pressure welding part 53 are same as the support shaft pin and the pressure welding part in the aforementioned ninth modification. The pressure transmission part 54K is a rigid part that receives an applied pressure and efficiently transmits the pressure to the pressure welding part 53. The pressure transmission part 54K is formed to have an inclination cam surface on the surface facing the pressure generating part 55K.

The pressure generating part 55K causes a predetermined pressing force to be generated by coming into contact with and pressing the pressure transmission part 54K. On the other hand, the pressure generating part 55K is a part that releases a pressing force by separating from and releasing contact with the pressure transmission part 54K.

In the tenth modification, the pressure generating part 55K is configured by employing a cam mechanism. The cam of the pressure generating part 55K presses the pressure transmission part 54K and the pressure welding part 53 by rotating in a direction of an arrow R2 (around the support shaft pin 43E) in FIG. 31. Also, the pressing of the pressure transmission part 54K and the pressure welding part 53 is released by rotating in a direction opposite to the direction of the arrow R2.

Effects of the thus configured tenth modification are same as the effects of the aforementioned ninth modification. It is also possible to obtain same advantages as the advantages of the ninth modification with the configuration of the tenth modification as well.

Eleventh Modification

Figure 33:
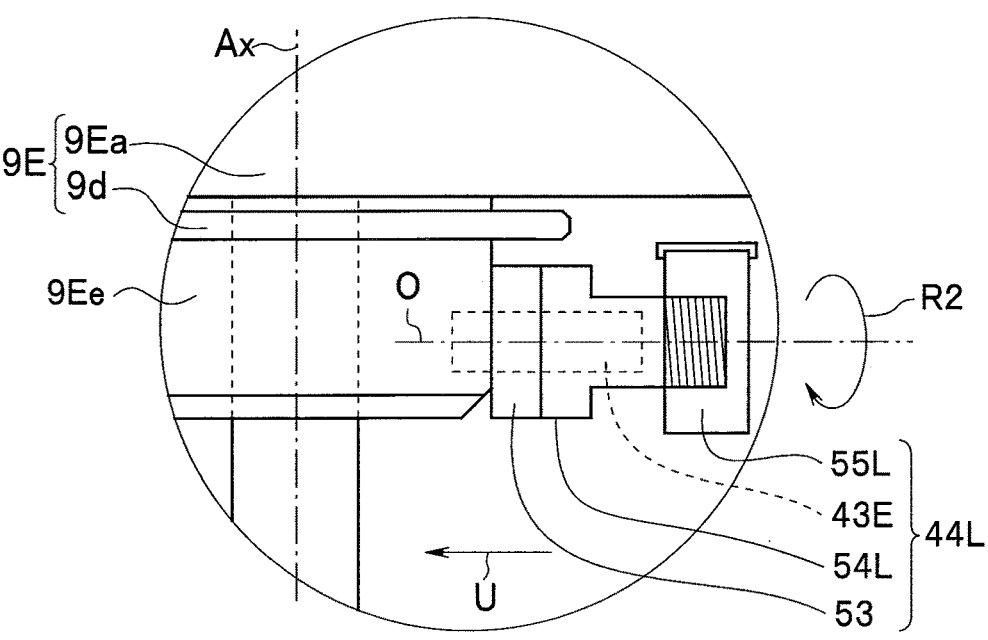
FIG. 33 is a conceptual diagram (released state) illustrating yet another different modification (eleventh modification) of the inclination maintaining mechanism in the endoscope in FIG. 1.
Figure 34:
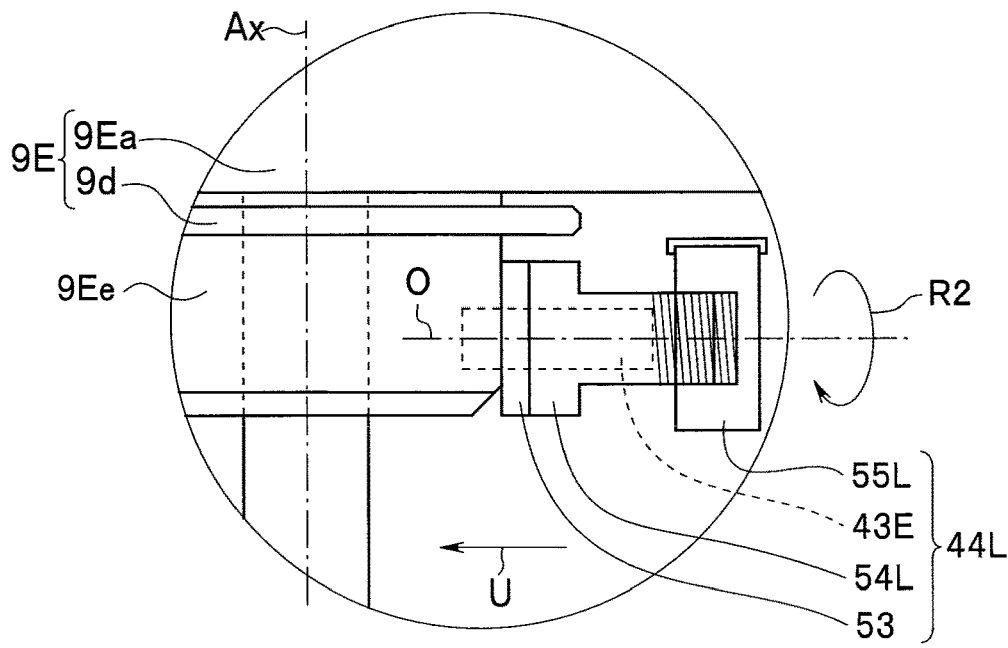
FIG. 34 is a conceptual diagram illustrating a fixed state of the inclination maintaining mechanism in FIG. 33.

FIGS. 33 and 34 are main part enlarged views conceptually illustrating yet another different modification (eleventh modification) of the inclination maintaining mechanism in the endoscope. Out of the drawings, FIG. 33 illustrates a released state and FIG. 34 illustrates a fixed state of the inclination maintaining mechanism. Note that FIGS. 33 and 34 conceptually illustrate only main configuration members in order to avoid complication of the drawings.

A basic configuration of the eleventh modification is substantially same as the configuration in the form illustrated in each of the aforementioned ninth modification (see FIGS. 28 to 30) and tenth modification (see FIGS. 31 and 32).

An inclination maintaining mechanism 44L illustrated in the eleventh modification is same as the inclination maintaining mechanisms in the ninth modification and the tenth modifications in that the inclination maintaining mechanism 44L has a configuration with which it is possible to maintain and release the inclined state of the center axis Ax of the bending operation knob 9E with the pressure to be applied to the fixed member 9Ee.

The inclination maintaining mechanism 44L illustrated as the eleventh modification is an angle fixing mechanism configured to include a support shaft pin 43E, a pressure welding part 53, a pressure transmission part 54L, a pressure generating part 55L, and the like.

The support shaft pin 43E and the pressure welding part 53 are same as support shaft pins and the pressure welding parts in the aforementioned ninth modification and tenth modification. The pressure transmission part 54L is a rigid part that receives an applied pressure and efficiently transmit the pressure to the pressure welding part 53. The pressure transmission part 54L is formed to include, at a first end, a plane that comes into contact with and presses the pressure welding part 53 and include, at a second end, a male screw section that is screwed into a female screw section of the pressure generating part 55L.

The pressure generating part 55L includes the female screw section that is fitted onto the male screw section of the pressure transmission part 54L and is fixed to an internal fixing section (not illustrated) of the operation section main body to be rotatable about the long axis (screw axis) and in the direction along the arrow U.

In other words, the pressure generating part 55L rotates in the direction of the arrow R2 (around the support shaft pin 43E) in FIG. 33 in a state where the female screw section is screwed onto the male screw section of the pressure transmission part 54L. Here, the pressure generating part 55L is fixed in the direction of the arrow U and thus causes the pressure transmission part 54L to move in the direction of the arrow U in FIG. 33.

With such a configuration, the pressure generating part 55L causes a predetermined pressing force to be generated by bringing the pressure transmission part 54L into contact with the pressure welding part 53 and pressing the pressure transmission part 54L. On the other hand, the pressure generating part 55L releases the pressing force by causing the pressure transmission part 54L to be separated from the pressure welding part 53.

In such a manner, the pressure generating part 55L is configured by employing the screw mechanism in the eleventh modification. The screw of the pressure generating part 55L presses the pressure transmission part 54L and the pressure welding part 53 by rotating in the direction of the arrow R2 in FIG. 33. The pressing of the pressure transmission part 54L and the pressure welding part 53 is released by rotating in the direction opposite to the direction of the arrow R2.

Effects of the thus configured eleventh modification are substantially same as the effects of the aforementioned ninth modification and tenth modification. It is also possible to obtain the same effects as the effects of the ninth modification and the tenth modification with the configuration of the eleventh modification as well.

Note that the cam mechanism or the screw mechanism configuring the inclination maintaining mechanisms that are the angle fixing mechanisms illustrated in the ninth to eleventh modifications can be caused to operate by operating an operator provided in the operation section main body.

Here, an eccentric lever-type operator, a dial-type operator, and the like are conceivable as the operator of the angle fixing mechanism, for example. In such a case, various forms as illustrated in FIGS. 35 to 38 are conceivable as configuration examples of the eccentric lever-type operator. Each of the form as illustrated in FIGS. 39 and 40 is conceivable as a configuration example of the dial-type operator.

Figure 37:
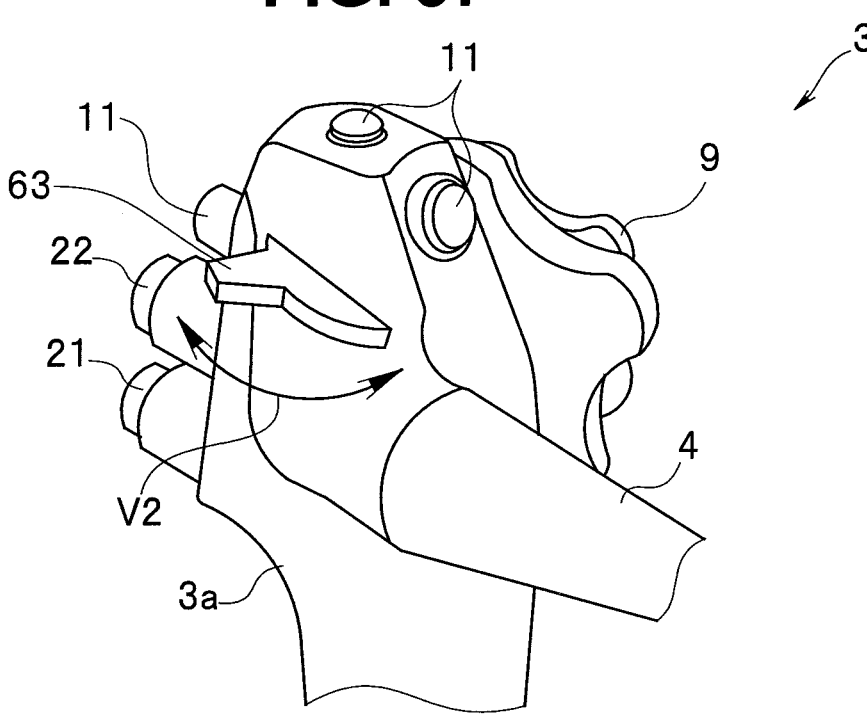
FIG. 37 is a diagram illustrating a configuration example of an eccentric lever-type operator (third operator).
Figure 38:
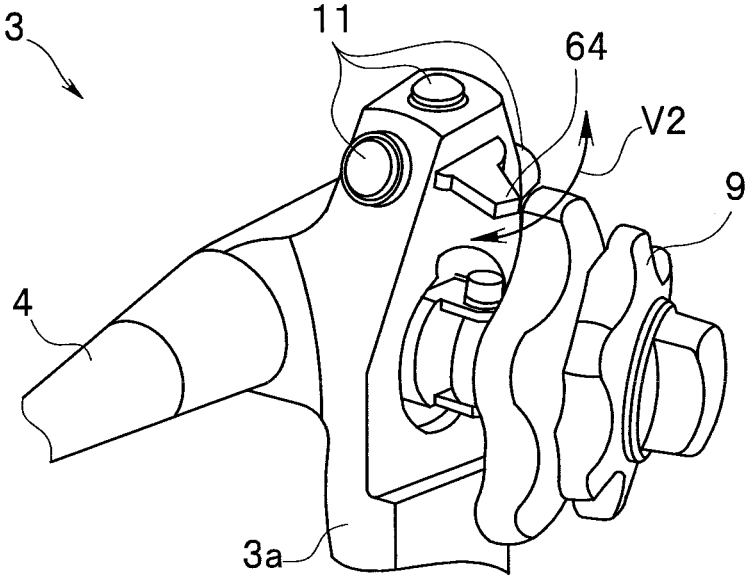
FIG. 38 is a diagram illustrating a configuration example of an eccentric lever-type operator (fourth operator).
Figure 39:
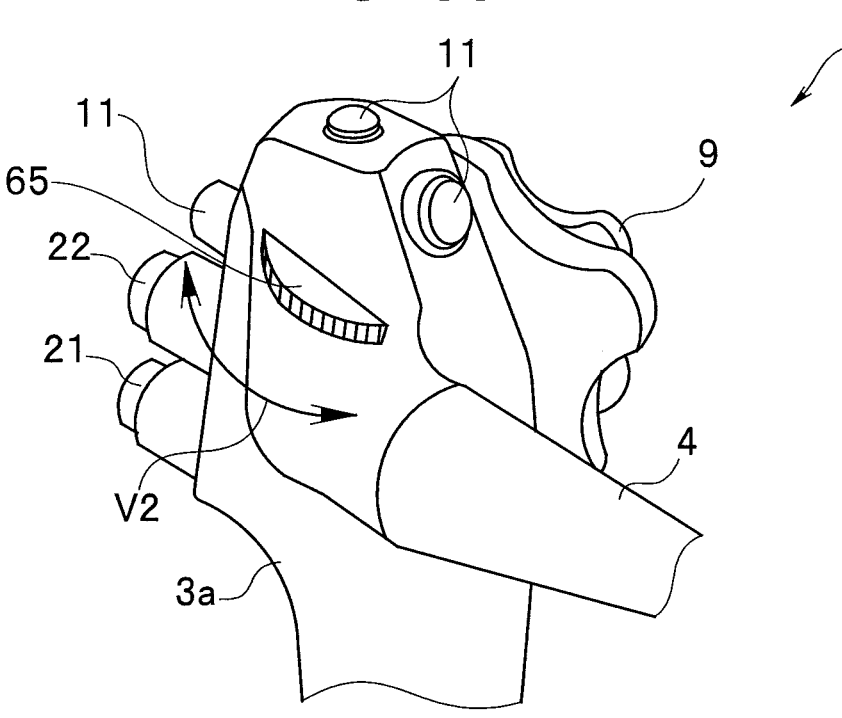
FIG. 39 is a diagram illustrating a configuration example of a dial-type operator (fifth operator) that can be applied to the inclination maintaining mechanisms in FIGS. 28 to 34.
Figure 40:
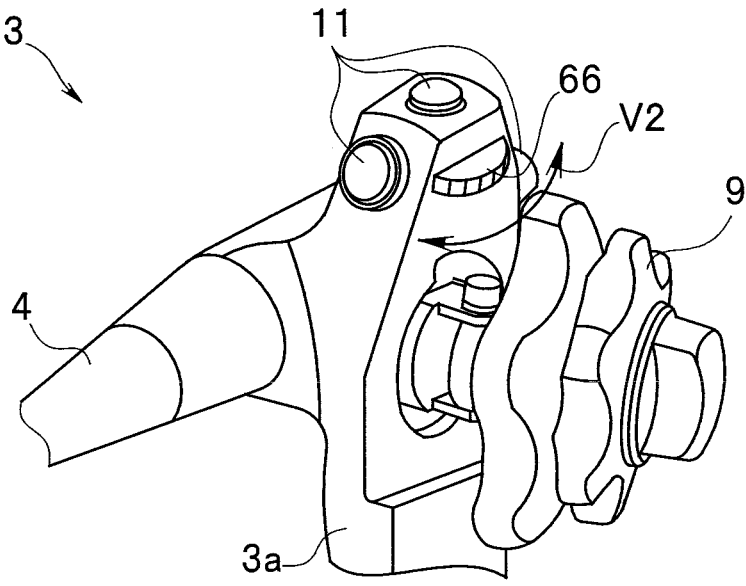
FIG. 40 is a diagram illustrating a configuration example of a dial-type operator (sixth operator).

FIGS. 35 to 40 are diagrams illustrating operators that can be applied to the cam mechanism or the screw mechanism configuring the inclination maintaining mechanism that is an angle fixing mechanism. Among the drawings, FIGS. 35 to 38 illustrate each of configuration examples of an eccentric lever-type operator. FIGS. 39 and 40 illustrate each of configuration examples of a dial-type operator.

Figure 35:
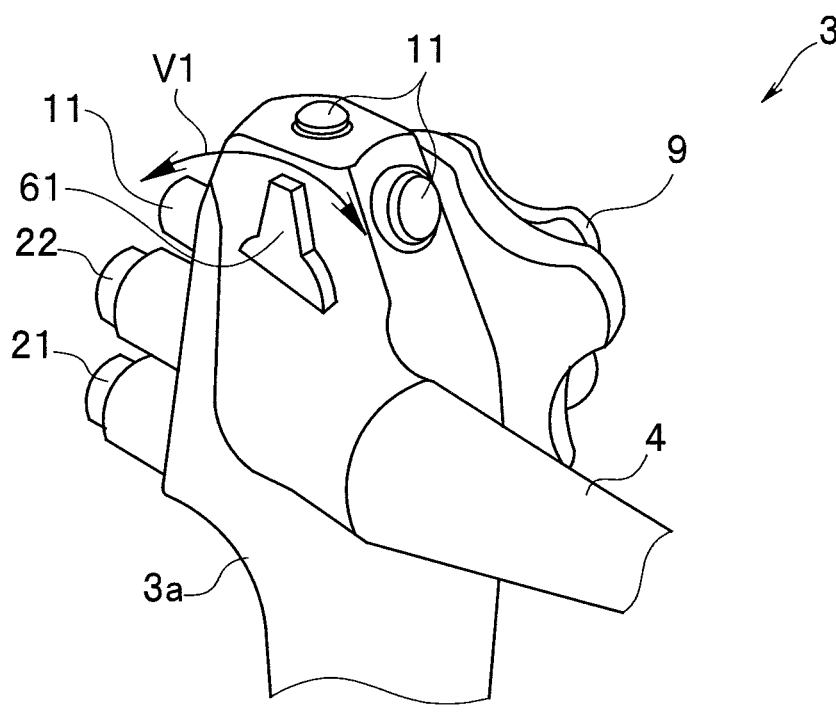
FIG. 35 is a diagram illustrating a configuration example of an eccentric lever-type operator (first operator) that can be applied to the inclination maintaining mechanisms in FIGS. 28 to 34.

A first operator 61 illustrated in FIG. 35 is an eccentric lever-type operator. The first operator 61 is provided in parallel to a side surface on a side on which the palm of the left hand is brought into contact when the user grasps the operation section main body 3a of the operation section 3. Here, the first operator 61 is located to be swingable in a direction of an arrow V illustrated in FIG. 35. In such a case, the swinging direction (a direction of an arrow V1) of the first operator 61 is a direction that is parallel to the advancing and retreating direction of the switch buttons.

Figure 36:
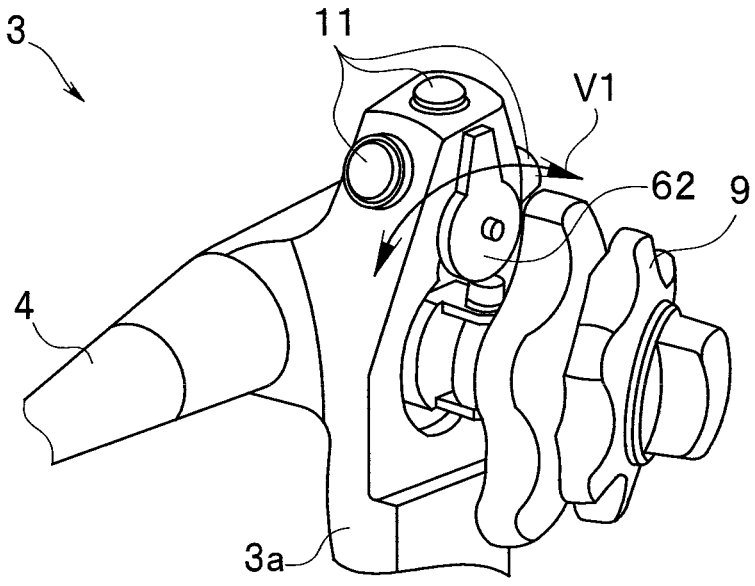
FIG. 36 is a diagram illustrating a configuration example of an eccentric lever-type operator (second operator).

The second operator 62 illustrated in FIG. 36 is an eccentric lever-type operator. The second operator 62 is provided to be parallel to the surface on the side on which the bending operation knob 9 is located in the operation section main body 3a of the operation section 3. Here, the second operator 62 is located to be swingable in the direction of the arrow V1 illustrated in FIG. 36. In such a case, the swinging direction (the direction of the arrow V1) of the second operator 62 is a direction that is parallel to the advancing and retreating direction of the switch buttons.

A third operator 63 in FIG. 37 is an eccentric lever-type operator. The third operator 63 is provided to project outward in the perpendicularly intersecting direction in the side surface on the side on which the palm of the left hand is brought into contact when the user grasps the operation section main body 3a of the operation section 3. Here, the third operator 63 is located to be swingable in a direction of an arrow V2 illustrated in FIG. 37. In such a case, the swinging direction (the direction of the arrow V2) of the third operator 63 is a direction that is parallel to the advancing and retreating direction of the switch buttons.

A fourth operator 64 illustrated in FIG. 38 is an eccentric lever-type operator. The fourth operator 64 is provided to project outward in the perpendicularly intersecting direction in the side surface on the side on which the bending operation knob 9 is located in the operation section main body 3a of the operation section 3. Here, the fourth operator 64 is located to be swingable in the direction of the arrow V2 illustrated in FIG. 38. In such a case, the swinging direction (the direction of the arrow V2) of the fourth operator 64 is a direction that is parallel to the advancing and retreating direction of the switch buttons.

A fifth operator 65 illustrated in FIG. 39 is a dial-type operator. The fifth operator 65 is provided to project outward in the perpendicularly intersecting direction in the side surface on the side on which the palm of the left hand is brought into contact when the user grasps the operation section main body 3a of the operation section 3. Here, the fifth operator 65 is located to be rotatable in the direction of the arrow V2 illustrated in FIG. 39. In this case, the swinging direction (the direction of the arrow V2) of the fifth operator 65 is a direction that is parallel to the advancing and retreating direction of the switch button.

A sixth operator 66 illustrated in FIG. 40 is a dial-type operator. The sixth operator 66 is provided to project outward in the perpendicularly intersecting direction in the side surface on the side on which the bending operation knob 9 is located in the operation section main body 3a of the operation section 3. Here, the sixth operator 66 is located to be rotatable in the direction of the arrow V2 illustrated in FIG. 40. In such a case, the swinging direction (the direction of the arrow V2) of the sixth operator 66 is a direction that is parallel to the advancing and retreating direction of the switch buttons.

Note that although illustration is omitted, a configuration with the same disposition as the disposition of the aforementioned first operator 61 (see FIG. 35) or the aforementioned second operator 62 (see FIG. 36) may be employed in the case of the dial-type operator as well.

Also, a configuration in which the inclination maintaining mechanism that is the angle fixing mechanism is caused to operate by using a known operation member, for example, an RL bending fixation knob 9c or a UD bending fixation lever 9d instead of providing the operator (FIGS. 35 to 40) as described above in the operation section main body may be employed.

Twelfth Modification

Incidentally, the endoscope in each embodiment of the present disclosure is configured such that the center axis Ax of the bending operation knob is disposed to be inclined in the direction in which the bending operation knob approaches on the side on which the switch button is located with respect to the surface (operation knob end surface) on which the bending operation knob is located in the operation section main body. In the case of such a configuration, a gap is formed between the operation knob end surface of the operation section main body and the lower surface of the bending operation knob in the surroundings of the bending operation knob on the side (the side on which the switch buttons are not provided) opposite to the direction in which the center axis Ax of the bending operation knob is inclined.

Thus, a configuration achieved by focusing the gap formed between the operation knob end surface of the operation section main body and the lower surface of the bending operation knob in the case where the center axis Ax of the bending operation knob in the endoscope is configured to be inclined will be illustrated in each of the following modifications.

Figure 41:
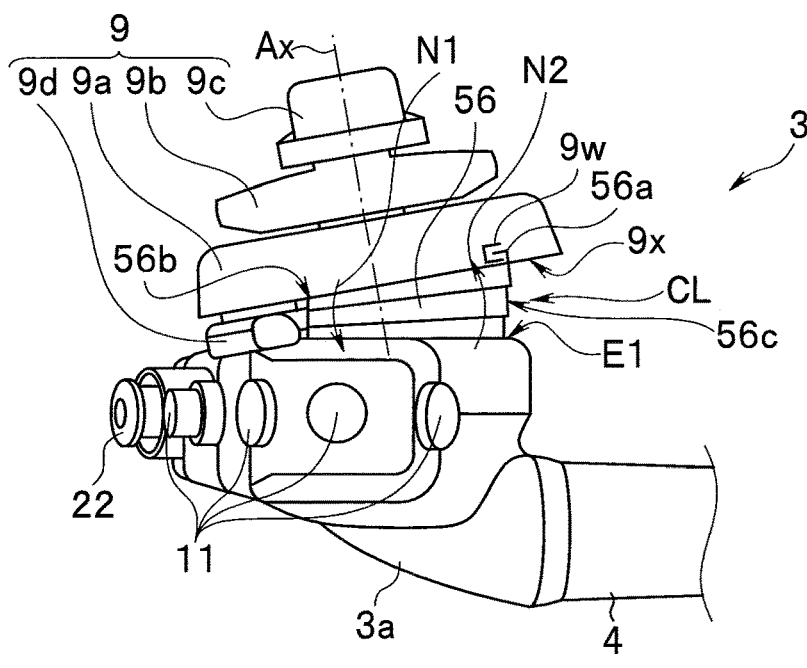
FIG. 41 is a schematic view illustrating a modification (twelfth modification) of the operation section in the endoscope in FIG. 1.

FIG. 41 is a main part enlarged view schematically illustrating a modification (twelfth modification) of the operation section in the endoscope.

The operation section 3 illustrated as the twelfth modification has a configuration in which the center axis Ax of the bending operation knob 9 is disposed to be inclined on the side on which the switch button (22) is located with respect to the operation knob end surface E1 of the operation section main body 3a as illustrated in FIG. 41. In such a case, the operation section main body 3a is adapted such that a sleeve member 56 which is a gap treating member is located to cover a part of the outer surface of the operation section main body 3a. Here, a gap CL formed between the operation knob end surface E1 of the operation section main body 3a and the lower surface 9x of the bending operation knob 9 corresponds to the part of the outer surface of the operation section main body 3a.

The sleeve member 56 is a configuration unit that is formed such that a plurality of members of short tubular shapes with different outer diameters are continuously connected in a shutter form and the sleeve member 56 can freely stretch and contract. The sleeve member 56 is formed by working a resin material such as a plastic plate, for example. The sleeve member 56 is disposed a space between the operation section main body 3a and the operation knob 9.

One surface of the sleeve member 56 is fixed to the operation knob end surface E1 of the operation section main body 3a. The other surface of the sleeve member 56 is rotatably fixed to the lower surface 9x of the bending operation knob 9. Therefore, a claw-shaped section 56 is formed in an outer peripheral portion of the other surface (the surface facing the lower surface 9x of the bending operation knob 9), for example, of the sleeve member 56. The claw-shaped section 56a engages with an engaged section 9w provided inside the UD bending operation knob 9a of the bending operation knob 9. The sleeve member 56 is thus rotatable with respect to the UD bending operation knob 9a of the bending operation knob 9.

The thus configured sleeve member 56 that is located to fill the gap CL stretches and contracts in accordance with the size of the gap CL changing with the inclination of the bending operation knob 9. In such a manner, the sleeve member 56 blocks at least a part of the gap CL and causes the gap CL to contract in accordance with the inclination of the bending operation knob 9.

Note that the sleeve member 56 has a structure in which the distal end 56*c* is lifted and opened by the proximal end 56*b* being pressed in a direction of an arrow N1 in FIG. 41 when the bending operation knob 9 is inclined.

Separately, the sleeve member 56 may have a structure in which the proximal end 56*b* is pressed by the distal end 56*c* being pulled and opened in the direction of the arrow N2 in FIG. 41 when the bending operation knob 9 is inclined.

According to the thus configured twelfth modification, the gap CL is covered, and the internal configurations can thus be covered, by providing the sleeve member 56 to fill the gap CL formed by the bending operation knob 9 being located in an inclined manner.

Thirteenth Modification

Figure 42:
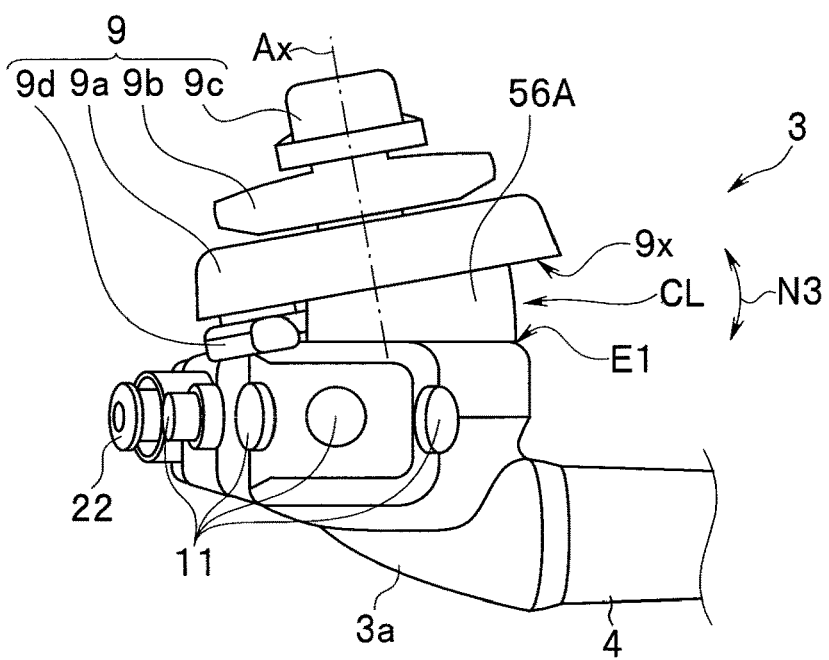
FIG. 42 is a schematic view illustrating another modification (thirteenth modification) of the operation section in the endoscope in FIG. 1.

FIG. 42 is a main part enlarged view schematically illustrating another modification (thirteenth modification) of the operation section in the endoscope.

The operation section 3 illustrated as the thirteenth modification basically has a substantially same configuration as the configuration of the aforementioned twelfth modification. The operation section main body 3*a* in the thirteenth modification is different only in a configuration of a sleeve member 56A which is a gap treating member provided to cover a part of the outer surface of the operation section main body 3*a*. Therefore, only parts that are different from the parts in the twelfth modification will be described below in detail in the following description.

The sleeve member 56A which is the gap treating member is worked and formed into a sleeve shape by using an elastic member such as a rubber material, for example. In the thirteenth modification, the sleeve member 56A is located to fill the gap CL as illustrated in FIG. 42.

One surface of the sleeve member 56A is fixed to the operation knob end surface E1 of the operation section main body 3*a*. The other surface of the sleeve member 56A is rotatably fixed to the lower surface 9*x* of the bending operation knob 9. The configuration to do so is substantially same as the configuration of the aforementioned twelfth modification.

The thus configured sleeve member 56A stretches and contracts in a direction of an arrow N3 in FIG. 42 due to an elastic force of the sleeve member 56A in accordance with the size of the gap CL changing with the inclination of the bending operation knob 9. In such a manner, the sleeve member 56A blocks at least a part of the gap CL and causes the gap CL to contract in accordance with the inclination of the bending operation knob 9.

It is possible to obtain the same effects as the effects of the twelfth modification in the thus configured thirteenth modification as well. According to the thirteenth modification, it is possible to further contribute to water proofness of the operation section main body 3*a*.

Fourteenth Modification

Figure 43:
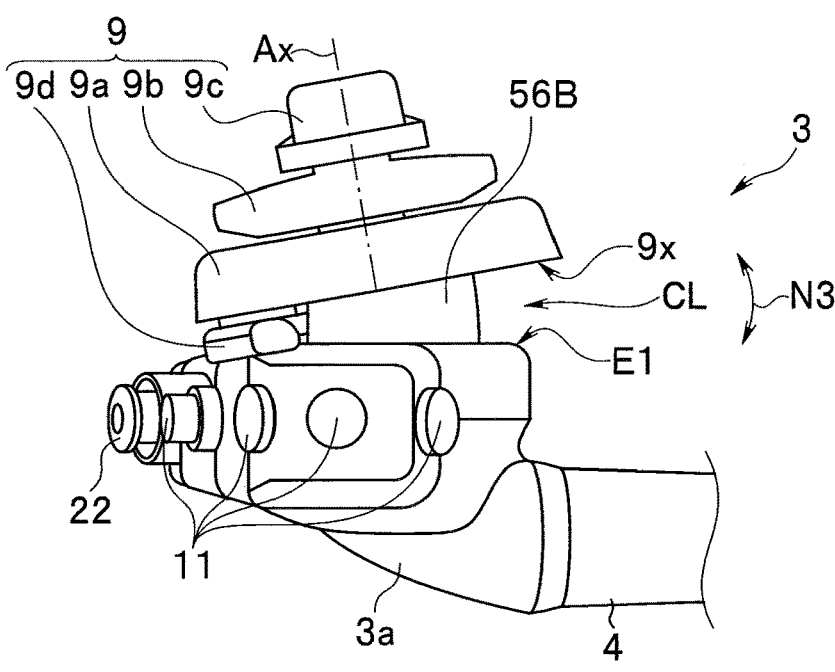
FIG. 43 is a schematic view illustrating another modification (fourteenth modification) of the operation section in the endoscope in FIG. 1.

FIG. 43 is a main part enlarged view schematically illustrating another modification (fourteenth modification) of the operation section in the endoscope.

The operation section 3 illustrated as the fourteenth modification basically has a substantially same configuration as the configuration of the aforementioned thirteenth modification. The operation section main body 3*a* in the fourteenth modification is different in a configuration of a sleeve member 56B which is a gap treating member provided to cover a part of the outer surface of the operation section main body 3*a*. Therefore, only parts that are different from the parts in the twelfth modification will be described in detail in the following description.

The sleeve member 56B which is a gap treating member is configured as a gap treating member by filling the gap CL with a gel-like member, for example. Therefore, a protector member with a substantially cylindrical shape or the like is provided around the rotation shaft (not illustrated) of the bending operation knob 9. The surroundings of the protector member are filled with the gel-like member, and the gel-like member stretches or contracts in a direction of an arrow N3 in FIG. 43 due to an elastic force of the gel-like member in accordance with the size of the gap CL when the bending operation knob 9 is inclined.

Note that the gel-like member is configured not to come into direct contact with the rotation shaft by providing the protector member. In the fourteenth modification, the sleeve member 56B is located to fill the gap CL as illustrated in FIG. 43.

It is possible to obtain the same effects and advantages as the effects and the advantages of the thirteenth modification by the thus configured fourteenth modification as well.

Fifteenth Modification

Figure 44:
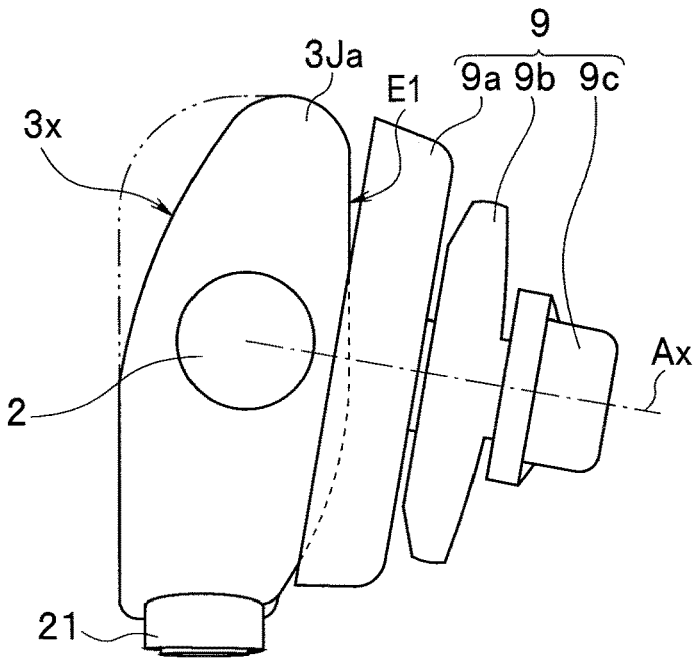
FIG. 44 is a schematic view illustrating a modification (fifteenth modification) of an operation section main body in the endoscope in FIG. 1.

FIG. 44 is a schematic view illustrating a modification (fifteenth modification) of the operation section main body in the endoscope. FIG. 44 illustrates an assumed case in which the operation section main body is seen in the longitudinal direction from the side of the insertion section.

An operation section main body 3Ja illustrated as the fifteenth modification basically has a substantially same configuration as the configuration illustrated in each of the aforementioned embodiments and the like. The fifteenth modification is slightly different only in an outer shape of the operation section main body 3Ja.

The operation section main body 3Ja in the fifteenth modification includes a bending operation knob 9 in a form in which a center axis Ax is caused to be inclined in a predetermined direction similarly to the illustrative example in each of the aforementioned embodiments. In such a case, the operation section main body 3Ja is formed such that the side surface with which the palm of the left hand is brought into contact at the time of utilization is inclined by a predetermined angle with respect to the operation knob end surface E1 of the bending operation knob 9.

In other words, the operation section main body 3Ja is provided with an inclined surface 3*x* with a shape with which the sectional area contracts toward the side on which the switch button (21) is not provided when seen from the side of the insertion section 2 in the longitudinal direction of the operation section.

According to the fifteenth modification, employing of the thus configured operation section main body 3Ja facilitates an access of fingers to the bending operation knob 9 by providing the inclined surface 3*x* even for the bending operation knob 9 in the inclined form. It is thus possible to contribute to an improvement in operability of the endoscope.

Sixteenth Modification

Figure 45:
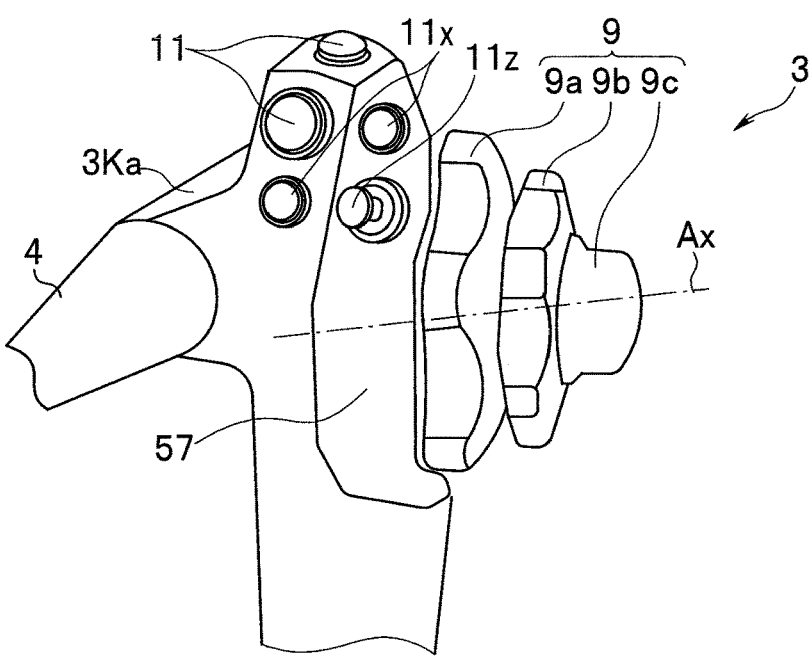
FIG. 45 is a schematic view illustrating another modification (sixteenth modification) of the operation section main body in the endoscope in FIG. 1.

FIG. 45 is a schematic view illustrating another modification (sixteenth modification) of the operation section main body in the endoscope.

An operation section main body 3Ka illustrated as the sixteenth modification basically has a substantially same configuration as the configuration illustrated in each of the aforementioned embodiments and the like. The sixteenth modification is further different in an outer shape of the operation section main body 3Ka.

The operation section main body 3Ka in the sixteenth modification is provided with a wall section 57 to cause a gap between the operation section main body 3Ka and the bending operation knob 9 to contract on the side on which the switch buttons are not provided, in the surroundings of the bending operation knob 9.

The wall section 57 is a site formed to fill the gap formed between the operation knob end surface of the operation section main body 3Ka and the lower surface of the bending operation knob 9 by employing a form in which the center axis Ax of the bending operation knob 9 is inclined in the operation section main body 3Ka. The wall section 57 is a part of an outer wall of the operation section main body 3Ka.

In such a case, the wall section 57 may be configured to be further provided with operators 11*x* and 11*z* to perform operations of functions different from the functions of the switch buttons (21, 22, 11, and the like).

Here, a press button-type operator is illustrated as the operator 11*x* illustrated in FIG. 45. A joystick-type operator is illustrated as the operator 11*z* illustrated in FIG. 45. Note that the operators that can be additionally located are not limited only to the illustrated forms and operators in other various forms can be applied.

In the thus configured sixteenth modification, the form is achieved in which the gap generated between the operation section main body 3Ka and the bending operation knob 9 by the bending operation knob 9 being located in an inclined manner is filled with the wall section 57 which is formed by a part of the operation section main body 3Ka. It is thus possible to protect incorporated parts by filling the gap. At the same time, it is possible to enlarge the surface area of the operation section main body 3Ka and thereby to use the surface area to install yet additional operators.

Seventeenth Modification

Figure 46:
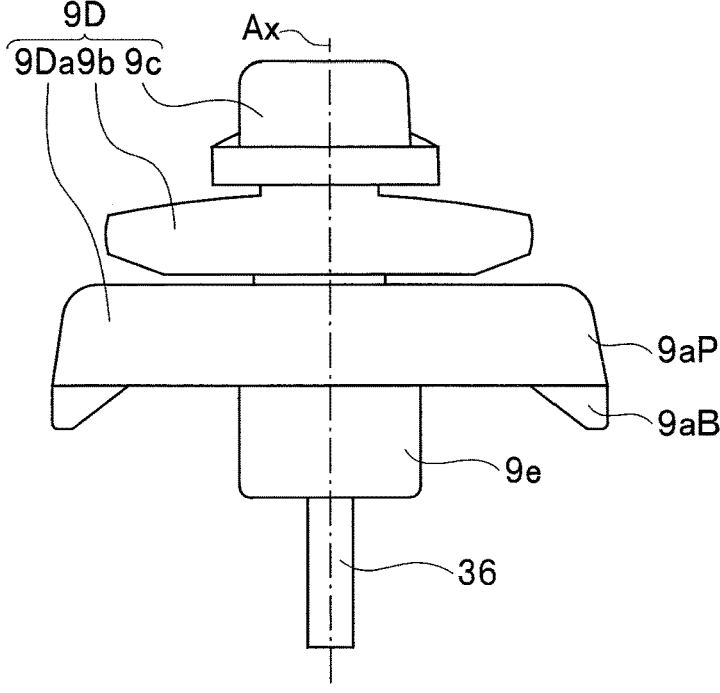
FIG. 46 is a schematic view illustrating a modification (seventeenth modification) of a bending operation knob in the endoscope in FIG. 1.

FIG. 46 is a schematic view illustrating a modification (seventeenth modification) of the bending operation knob in the endoscope.

A bending operation knob 9D illustrated as the seventeenth modification basically has a substantially same configuration as the configuration of the bending operation knob in each of the aforementioned embodiments and the like. The seventeenth modification is slightly different only in a configuration of a UD bending operation knob 9Da which is a first operation knob in a bending operation knob 9D.

The UD bending operation knob 9Da in the seventeenth modification includes an extended projecting section (protruding portion) 9*a*B which is an extended section obtained by extending downward the distal end of the projecting section 9*a*P of the outer peripheral portion. The extended projecting section 9*a*B is an extended section obtained by extending at least a part of the surface of the UD bending operation knob 9Da on the side of the outer periphery in a direction that is parallel to the rotation center axis (36). The operation knob 9 can include the protruding portion 9*a*B protruding along the center axis Ax of the operation knob 9.

According to the seventeenth modification, the area of the site where the fingers come into contact with the UD bending operation knob 9Da when the user operates the knob increases, and it is thus possible to perform an operation with a small amount of force, even with the bending operation knob 9D in the inclined form by employing the thus configured UD bending operation knob 9Da. Therefore, it is thus possible to contribute to an improvement in operability of the endoscope.

Also, since the bending operation knob 9D is inclined, the site where the fingers come into contact with the bending operation knob 9D is disposed at a position separated from the operation section main body on the side of the thumb, in particular. In such a case, it becomes easy to place the thumb on the UD bending operation knob 9Da if the extended projecting section 9*a*B is provided. It is thus possible to contribute to an improvement in operability of the endoscope.

Eighteenth Modification

Figure 47:
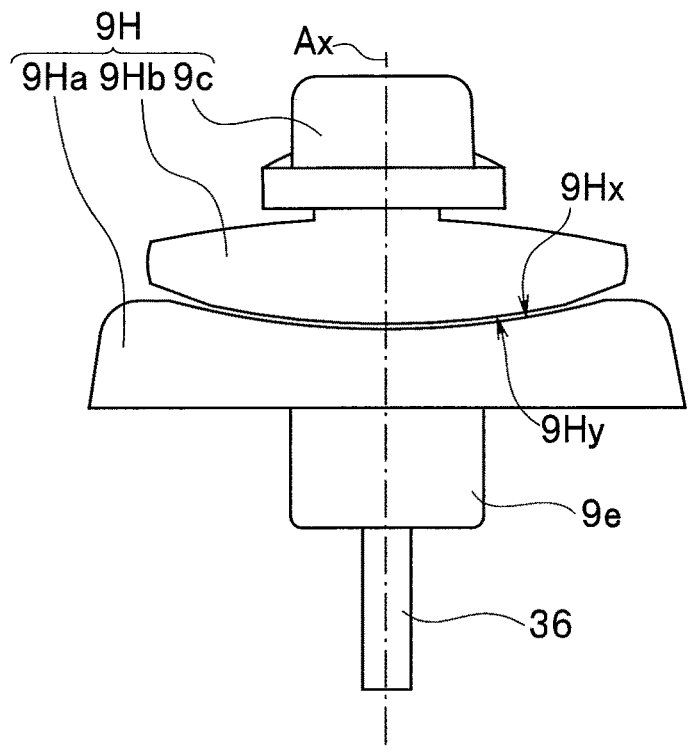
FIG. 47 is a schematic view illustrating another modification (eighteenth modification) of the bending operation knob in the endoscope in FIG. 1.

FIG. 47 is a schematic view illustrating another modification (eighteenth modification) of the bending operation knob in the endoscope.

A bending operation knob 9H illustrated as the eighteenth modification basically has a substantially same configuration as the configuration of the bending operation knob in each of the aforementioned embodiments and the like. The eighteenth modification is slightly different only in configurations of a UD bending operation knob 9Ha which is a first operation knob and an RL bending operation knob 9Hb which is a second operation knob, in the bending operation knob 9H.

The UD bending operation knob 9Ha in the eighteenth modification is formed to have a recessed section 9Hx with a shape recessed further inward in the direction along the rotation center axis (36) than the outer peripheral region in a substantially center region. Correspondingly, the RL bending operation knob 9Hb is formed to have a projecting section 9Hy with a shape projecting further outward in the direction along the rotation center axis (36) than the outer peripheral region in the substantially center region.

The projecting section 9Hy of the RL bending operation knob 9Hb is disposed in an accommodated form in the recessed section 9Hx of the UD bending operation knob 9Ha when the bending operation knob 9H is brought into an assembled state. In other words, at least a part of the outer surface in the substantially center region of the RL bending operation knob 9Hb is accommodated inside the recessed section 9Hx.

According to the thus configured eighteenth modification, it is possible to shorten a distance between the UD bending operation knob 9Ha and the RL bending operation knob 9Hb in the direction along the center axis Ax in the bending operation knob 9H. Therefore, an access of the fingers to the two operation knobs (9Ha and 9Hb) of the bending operation knob 9H is facilitated at the time of utilization.

Nineteenth Modification

Figure 48:
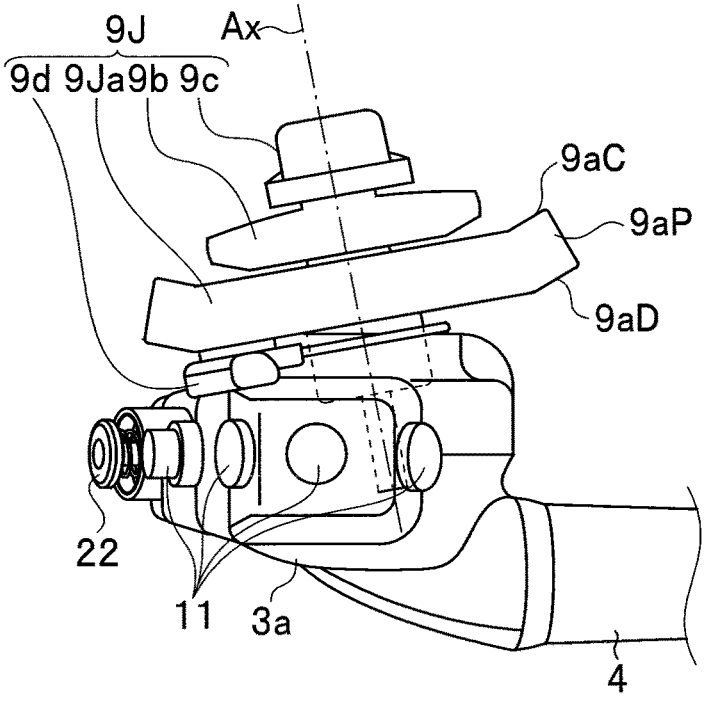
FIG. 48 is a schematic view illustrating another modification (nineteenth modification) of the bending operation knob in the endoscope in FIG. 1.

FIG. 48 is a schematic view illustrating another modification (nineteenth modification) of the bending operation knob in the endoscope.

A bending operation knob 9J illustrated as the nineteenth modification basically has a substantially same configuration as the configuration of the bending operation knob in each of the aforementioned embodiments and the like. The nineteenth modification is slightly different only in a configuration of a UD bending operation knob 9Ja which is a first operation knob in the bending operation knob 9J.

The UD bending operation knob 9Ja in the nineteenth modification includes a notch section 9aD obtained by cutting a part of a surface (the lower surface of the UD bending operation knob 9Ja) on the side facing the operation section main body 3a in the distal end outer peripheral portion of the projecting section 9aP of the outer peripheral portion. Furthermore, the UD bending operation knob 9Ja includes a thick section (protruding portion) 9aC which is a site corresponding to the notch section 9aD and is formed by raising upward a part of the surface (the upper surface of the UD bending operation knob 9Ja) separated from the operation section main body 3a. The operation knob 9 can include the protruding portion 9aC protruding along the center axis Ax of the operation knob 9.

According to the nineteenth modification, it is possible to avoid interference of the outer peripheral portion of the UD bending operation knob 9Ja with the switch buttons by providing the notch section 9aD even with the bending operation knob 9J in the inclined form by employing the thus configured UD bending operation knob 9Ja.

Since a region between the bending operation knob 9J and the switch button (22) is thus sufficiently secured, operability is not inhibited, when the user touches the bending operation knob 9J with the fingers and performs an operation. It is thus possible to contribute to an improvement in operability of the endoscope.

Twentieth Modification

Figure 49:
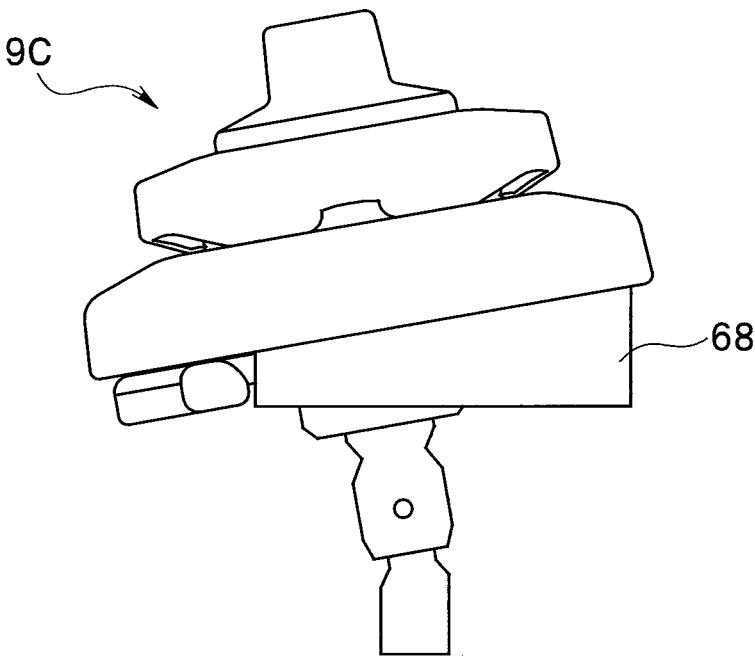
FIG. 49 is a schematic view illustrating a different modification (twentieth modification) of the bending operation knob in the endoscope in FIG. 1.

FIG. 49 is a schematic diagram illustrating a different modification (twentieth modification) of the bending operation knob in the endoscope.

A bending operation knob 9C illustrated as the twentieth modification basically has a substantially same configuration as the configuration applied to the aforementioned third embodiment. The twentieth modification is different in that the bending operation knob 9C is configured to be attachable/detachable to and from the operation section main body (not illustrated) and an angle defining base member 68 is further included.

The angle defining base member 68 is a gap treating member provided to cover a part (a gap part generated by the bending operation knob being inclined) of the outer surface of the operation section main body when the bending operation knob 9C is attached to the operation section main body, by being attached to the side of the lower surface of the bending operation knob 9C.

The angle defining base member 68 is rotatably attached to the bending operation knob when the angle defining base member 68 is attached to the side of the lower surface of the bending operation knob 9C. A plurality of angle defining base members 68 are prepared in accordance with an inclination set angle of the bending operation knob.

According to the thus configured twentieth modification, it is possible to easily perform desired inclination angle setting of the bending operation knob by appropriately detaching the bending operation knob 9C from the operation section main body, selecting the angle defining base member 68 corresponding to a desired inclination angle, attaching the angle defining base member 68 to the bending operation knob 9C, and assembling the bending operation knob 9C to the operation section main body.

Note that the twentieth modification assumes that the angle defining base member 68 is configured as a separate element from the bending operation knob 9C and is utilized by being appropriately attached or detached. However, the angle defining base member 68 is not limited to such a configuration example. As another configuration example, the angle defining base member 68 may be configured integrally with the bending operation knob 9C, for example. In such a case, the bending operation knob 9C and the angle defining base member 68 for performing predetermined angle setting are configured as a set, and it is possible to omit the time and effort for the assembly.

Twenty First Modification

Incidentally, the form in which the pulleys included in the bending operation mechanism are also caused to be inclined when the center axis of the bending operation knob is located in an inclined manner is employed in the aforementioned first and second embodiments. In the case of such a configuration, loosening may occur in the long members (bending wires) extending from the pulleys.

Thus, a configuration of a bending wire auto tension mechanism for curbing loosening of the long members (bending wires) in a case where the center axis Ax of the bending operation knob in the endoscope is inclined and the pulleys of the bending mechanism are also configured to be inclined will be described in each of the following modifications.

Figure 50:
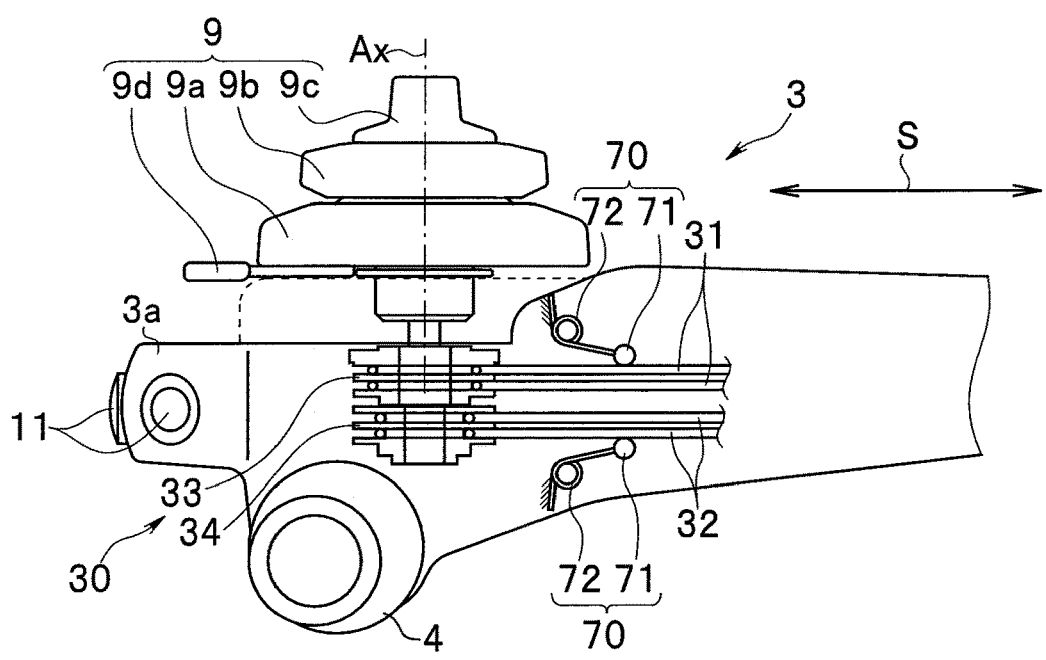
FIG. 50 is a schematic view illustrating a modification (twenty first modification) of a bending wire auto tension mechanism in the endoscope in FIG. 1.

FIG. 50 is a schematic diagram illustrating a modification (twenty first modification) of the bending wire auto tension mechanism in the endoscope.

The endoscope 1 illustrated as the twenty first modification basically has a substantially same configuration as the configurations of the aforementioned first and second embodiments. Therefore, illustration and description of the detailed configuration of the endoscope 1 will be omitted, and only parts related to the bending wire auto tension mechanism will be described in detail.

The endoscope 1 illustrated in the twenty first modification includes a bending wire auto tension mechanism (wire tension mechanism) 70 inside the operation section main body 3a. The bending wire auto tension mechanism 70 is a tension adjustment mechanism that reduces slacks of the bending wires (31 and 32) by applying a predetermined tension to the bending wires (31 and 32) which are long members extending from the pulleys (33 and 34) included in the bending operation mechanism 30. The wire tension mechanism 70 is configured to apply a predetermined tension to the wire 31 or 32.

A biasing mechanism of the bending wire auto tension mechanism 70 illustrated in the twenty first modification is illustrated in a configuration example including a contactor 71 and a torsion spring (helical spring) 72.

The contactor 71 is a part that comes into contact with the bending wires (31 and 32) and transmits a tension force (biasing force) of the torsion spring 72 to the bending wires (31 and 32). The torsion spring 72 is a biasing member that constantly biases the bending wires (31 and 32) with a predetermined tension. Therefore, one end of the torsion spring 72 is fixed to the internal fixing section of the operation section main body 3a, while the other end is fixed to the contactor 71.

The bending wire auto tension mechanism 70 includes a pair of biasing mechanisms (71 and 72) corresponding to the pair of bending wires (the first bending wire (UD) 31 and the second bending wire (RL) 32).

In the bending wire auto tension mechanism 70 illustrated by the twenty first modification, the pair of biasing mechanisms (71 and 72) are located at mutually facing positions with the pair of bending wires (31 and 32) sandwiched. The pair of torsion springs 72 are configured to constantly apply a biasing force such that part of the pair of bending wires (31 and 32; the two long members) disposed to be adjacent to each other approaches each other.

According to the thus configured twenty first modification, it is possible to curb loosening of the bending wires even in the case of the form in which the center axis of the bending operation knob including the pulleys are inclined.

Twenty Second Modification

Figure 51:
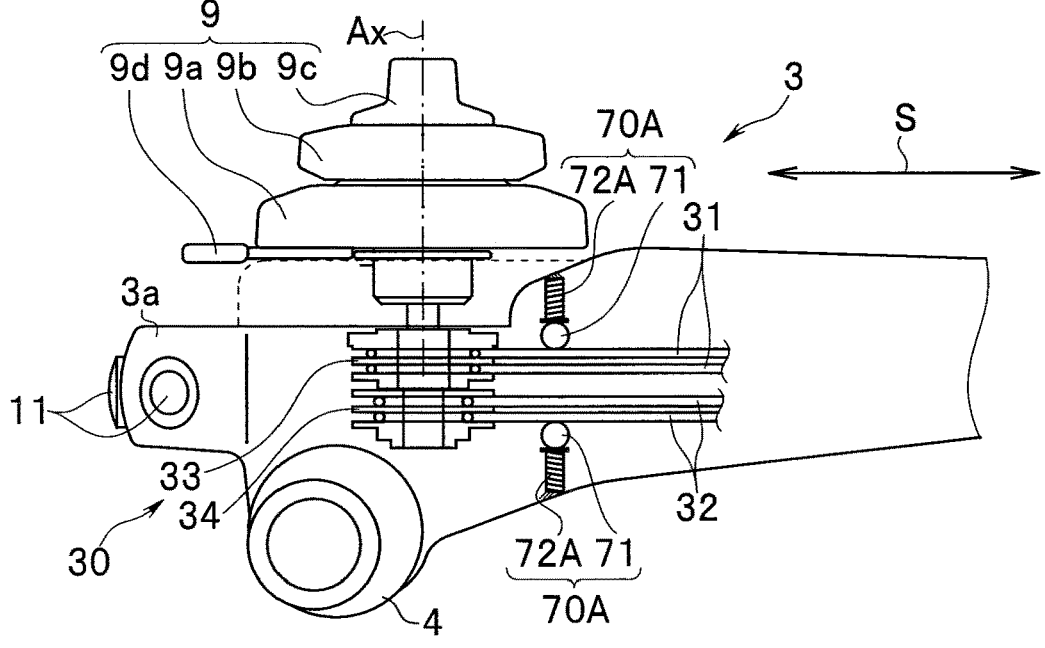
FIG. 51 is a schematic view illustrating another modification (twenty second modification) of the bending wire auto tension mechanism in the endoscope in FIG. 1.

FIG. 51 is a schematic diagram illustrating another modification (twenty second modification) of the bending wire auto tension mechanism in the endoscope.

A biasing mechanism of a bending wire auto tension mechanism 70A illustrated as the twenty second modification is illustrated in a configuration example including a contactor 71 and a coil spring 72A.

The contactor 71 is the same part as the part used in the twenty first modification. The coil spring 72A is a biasing member that constantly biases the bending wires (31 and 32) with a predetermined tension. Therefore, one end of the coil spring 72A is fixed to the internal fixing section of the operation section main body 3a, while the other end is fixed to the contactor 71.

The bending wire auto tension mechanism 70A includes a pair of biasing mechanisms (71 and 72A) corresponding to the pair of bending wires (the first bending wire (UD) 31 and the second bending wire (RL) 32).

The bending wire auto tension mechanism 70A illustrated by the twenty second modification is different only in that the coil spring 72A is applied instead of the torsion spring 72 in the aforementioned twenty first modification.

In the bending wire auto tension mechanism 70A illustrated by the twenty second modification, the pair of biasing mechanisms (71 and 72A) are located at mutually facing positions with the pair of bending wires (31 and 32) sandwiched. The pair of coil springs 72A are same as the springs in the aforementioned twenty first modification in that the pair of coil springs 72A are configured to constantly apply a biasing force such that parts of the pair of bending wires (31 and 32; the two long members) disposed to be adjacent to each other approach each other. Effects and advantages of the thus configured twenty second modification are same as the effects and the advantages of the aforementioned twenty first modification.

Twenty Third Modification

Figure 52:
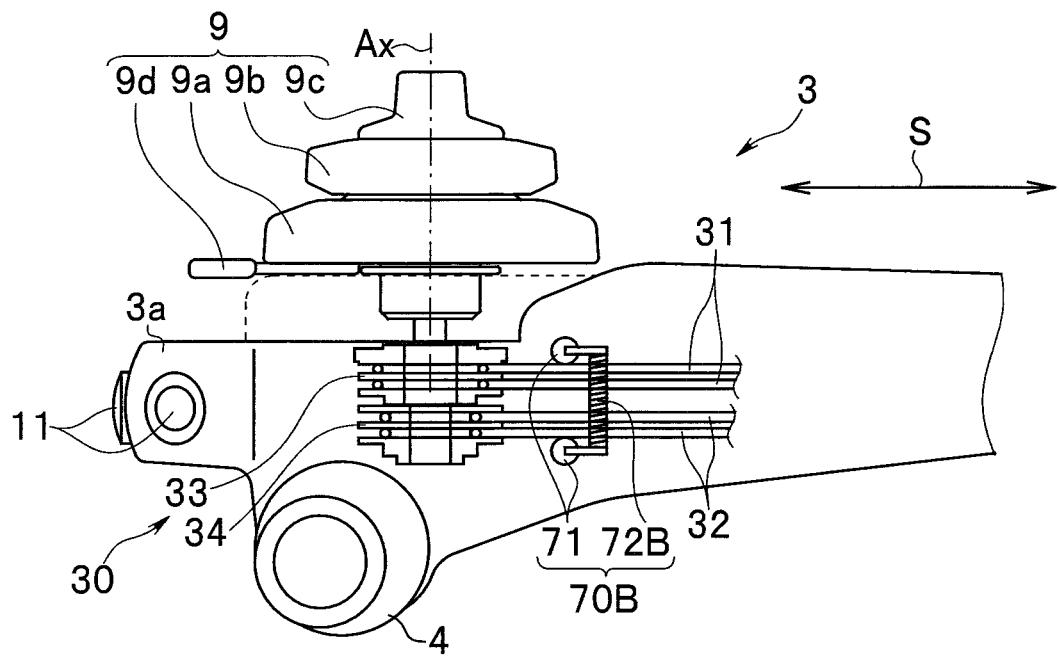
FIG. 52 is a schematic view illustrating another modification (twenty third modification) of the bending wire auto tension mechanism in the endoscope in FIG. 1.

FIG. 52 is a schematic diagram illustrating another modification (twenty third modification) of the bending wire auto tension mechanism in the endoscope.

A biasing mechanism of a bending wire auto tension mechanism 70B illustrated as the twenty third modification is illustrated in a configuration example including contactors 71 and a coil spring 72B.

The contactors 71 are same parts as the parts used in the twenty first and twenty second modifications. The coil spring 72B is a biasing member that constantly biases the bending wires (31 and 32) with a predetermined tension.

In such a case, the coil spring 72B is a stringent coil spring. One end of the coil spring 72B is fixed to one of contactors 71 corresponding to the first bending wire (UD) 31, and the other end is fixed to the other contactor 71 corresponding to the second bending wire (RL) 32. With such a configuration, the coil spring 72B is constantly biased in a direction in which the pair of contactors 71 are caused to approach each other.

In the bending wire auto tension mechanism 70B illustrated by the twenty third modification, the pair of contactors 71 are located at mutually facing positions with the pair of bending wires (31 and 32) sandwiched. A biasing force is constantly applied to the pair of contactors 71 such that parts of the pair of bending wires (31 and 32; the two long members) disposed to be adjacent to each other are caused to approach each other with the coil spring 72B. Effects and advantages of the thus configured twenty third modification are substantially same as the effects and the advantages of the aforementioned twenty first and twenty second modifications.

Twenty Fourth Modification

Incidentally, some endoscopes has a configuration with which it is possible to cause a predetermined treatment instrument to be inserted into a treatment instrument insertion channel inserted into and disposed inside the insertion section and to cause the distal end part of the treatment instrument to project forward from the distal end opening provided at the distal end section of the endoscope.

According to the endoscope with such a configuration, it is possible to perform a treatment inside the body cavity by using the treatment instrument by causing the treatment instrument to be inserted into the treatment instrument insertion channel of the insertion section in a state where the insertion section is inserted into the body cavity of the subject.

Some endoscope of such a type further includes a configuration unit for changing an advancing direction of the treatment instrument that is caused to project outward from the distal end opening of the insertion section, which is a so-called treatment instrument raising base (forceps elevator). A treatment instrument raising operation lever which is an operation member for performing a raising operation of the treatment instrument raising base is typically located coaxially with the center axis of the bending operation knob on the operation section main body. The treatment instrument raising operation lever acts on the treatment instrument raising base through a treatment instrument raising mechanism (not illustrated) inside the operation section main body.

On the other hand, some image pickup optical system provided inside the distal end section of the insertion section in the endoscope includes a so-called zoom optical system that is configured to enable variable magnification. Some zoom lever which is an operation member for performing a zooming operation of the zoom optical system is also located coaxially with the center axis of the bending operation knob on the operation section main body. The zoom lever acts on the zoom optical system through a zoom mechanism (not illustrated) included in an image pickup optical mechanism inside the operation section main body or inside the distal end section of the insertion section.

In such a manner, a configuration example described below is conceivable in a case where the configuration in each of the aforementioned embodiments, that is, the configuration in which the bending operation knob is inclined with respect to the operation knob end surface of the operation section main body is applied to the endoscope including the treatment instrument raising operation lever or the zoom lever.

Figure 53:
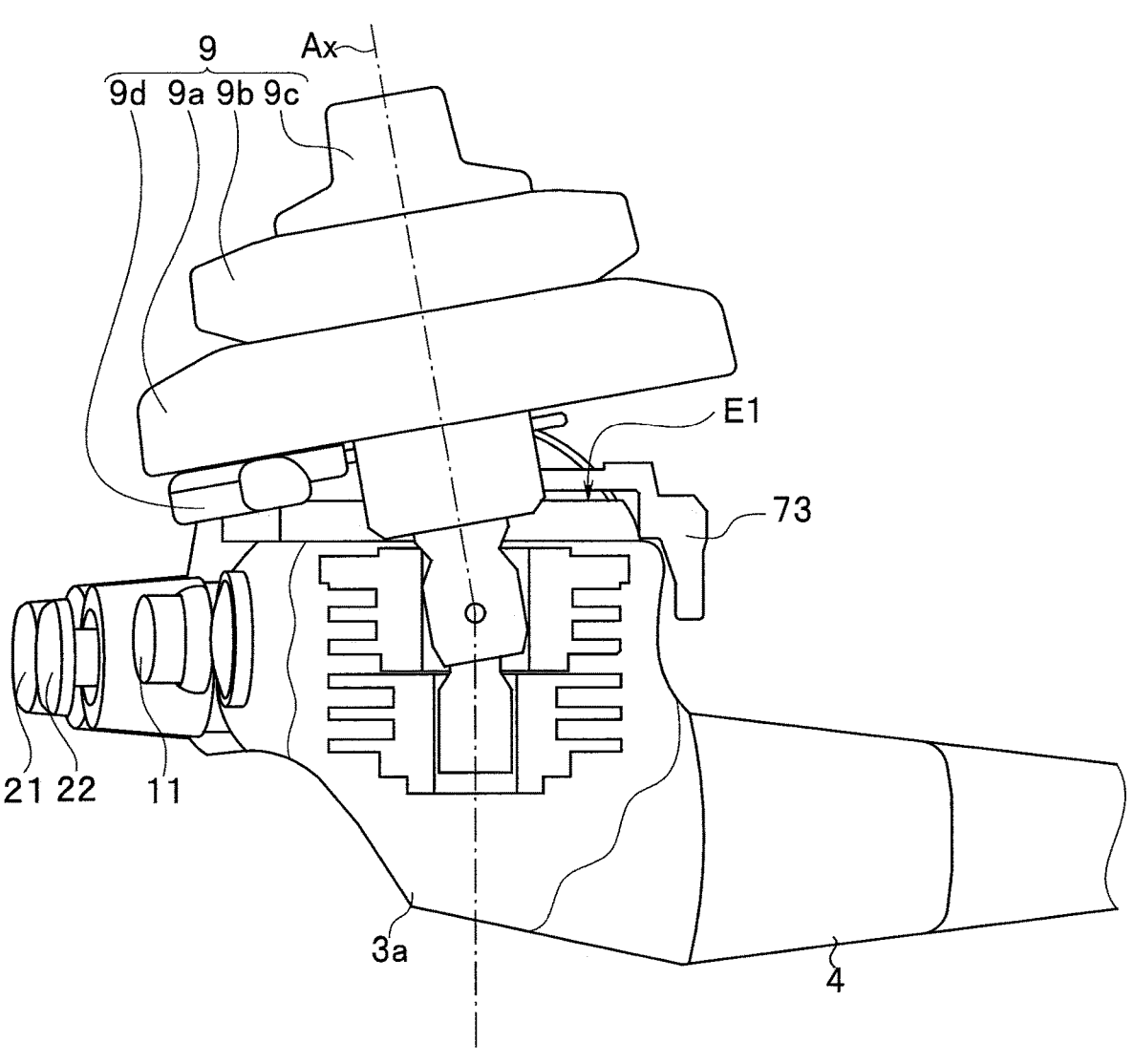
FIG. 53 is a schematic view illustrating a modification (twenty fourth modification) of an operation lever in an endoscope including a treatment instrument raising operation lever or a zoom lever.

FIG. 53 is a schematic view illustrating a configuration example (twenty fourth modification) of the operation lever in the endoscope including the treatment instrument raising operation lever or the zoom lever.

As illustrated in FIG. 53, the twenty fourth modification is a configuration example in which a lever operation member 73 which is the treatment instrument raising operation lever or the zoom lever is disposed to be substantially parallel to the operation knob end surface E1 of the operation section main body 3a when the center axis Ax of the bending operation knob 9 is configured to be inclined with respect to the operation section main body 3a as illustrated in FIG. 53. In such a case, the lever operation member 73 is configured as a separated element from the bending operation knob 9.

In the configuration example of the twenty fourth modification, it is possible to realize the configuration without changing the disposition or changing the structure of the internal configuration mechanism (the treatment instrument raising mechanism or the zoom mechanism) that operates in conjunction with the lever operation member 73.

Twenty Fifth Modification

Figure 54:
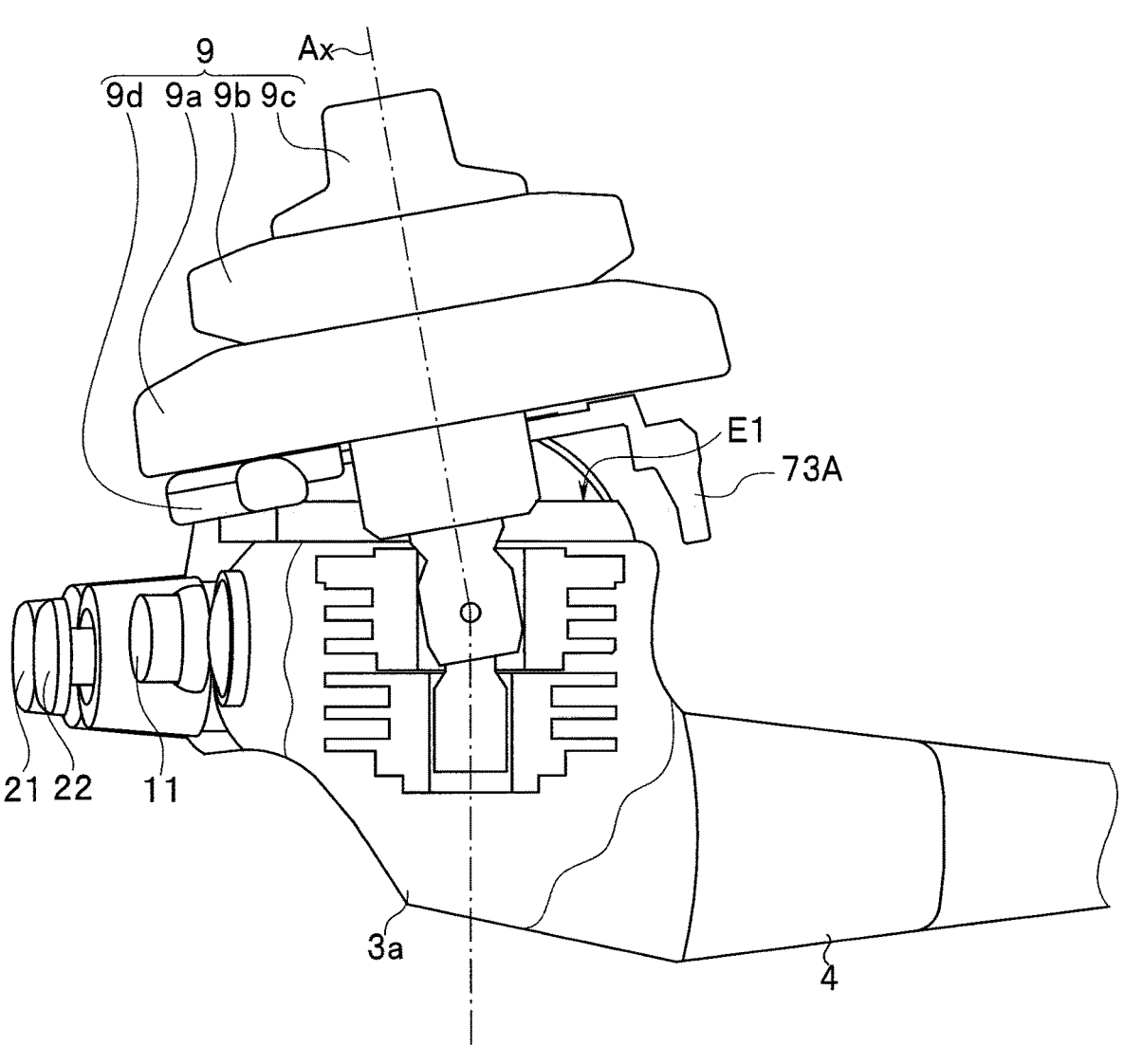
FIG. 54 is a schematic view illustrating a modification (twenty fifth modification) of the operation lever in the endoscope including the treatment instrument raising operation lever or the zoom lever.

FIG. 54 is a schematic diagram illustrating a configuration example (twenty fifth modification) of the operation lever in the endoscope including the treatment instrument raising operation lever or the zoom lever.

As illustrated in FIG. 54, the twenty fifth modification is an example of a form in which a lever operation member 73A that is the treatment instrument raising operation lever or the zoom lever is inclined with respect to the operation knob end surface E1 of the operation section main body 3a similarly to the bending operation knob 9 when the center axis Ax of the bending operation knob 9 is configured to be inclined with respect to the operation section main body 3a. In such a case, the lever operation member 73A is configured integrally with the bending operation knob 9.

In the configuration example of the twenty fifth modification, a positional relationship between the bending operation knob 9 and the lever operation member 73A does not change from the positional relationship in the case of the configuration in which the bending operation knob 9 is not inclined. According to the twenty fifth modification, operability of the endoscope is thus not inhibited, and it is possible to secure same operability as the operability of the configuration in the related art.

Note that although FIGS. 53 and 54 described above illustrate the configuration example using the configuration of the aforementioned third embodiment, the present disclosure is not limited to the configuration examples. It is also possible to employ the configuration in which the treatment instrument raising operation lever or the zoom lever is included in the configurations of the first embodiment or the second embodiment and each of the modifications, for example, in addition to the configuration examples.

Although the gastrointestinal endoscope has been illustrated as the endoscope in each of the embodiments of the present disclosure, the present disclosure is not limited to the examples and can also be applied similarly to endoscopes in other forms. Also, although the present embodiments have been described by exemplifying a single-use endoscope, the present disclosure is not limited to the examples, and the present disclosure can also be applied to an endoscope in a so-called reusable form that is repeatedly used by performing predetermined cleaning and sterilization treatment after utilization, for example.

It is a matter of course that the present disclosure is not limited to the aforementioned embodiments and various modifications and applications can be carried out without departing from the gist of the present disclosure. Furthermore, the aforementioned embodiments include disclosures in various stages, and various disclosures can be extracted by appropriately combining a plurality of disclosed configuration requirements. For example, in a case where the problem to be solved by the disclosure can be solved and the advantages of the disclosure can be obtained even if some configuration requirements are deleted from all the configuration requirements described in each of the aforementioned embodiments, the configurations obtained by deleting the configuration requirements can be extracted as the disclosures. Moreover, components in different embodiments may be appropriately combined. The disclosure is limited only by the accompanying claims and is not limited by specific embodiments.

Example 1. An endoscope comprising:

an insertion section that is inserted into a subject from a side of a distal end;

an operation section main body that is provided continuously from a side of a proximal end of the insertion section and is grasped by a user;

an operation knob that is disposed in the operation section main body and performs an operation of moving the side of the distal end of the insertion section; and a switch button that is provided in the operation section main body and performs advancing and retreating motions to perform other operations of the insertion section, wherein a center axis of the operation knob is disposed to be inclined to form an acute angle with respect to a direction that is perpendicular to each of a longitudinal direction of the operation section main body and an advancing and retreating direction of the switch button in a view in the longitudinal direction.

Example 2. The endoscope according to Example 1, wherein the center axis of the operation knob is disposed to be inclined in a direction in which the operation knob approaches a side where the switch button is provided.

Example 3. The endoscope according to Example 2, wherein the center axis of the operation knob is disposed to be inclined by not less than 1 degree and not more than 30 degrees with respect to the direction that is perpendicular to each of the longitudinal direction and the advancing and retreating direction of the switch button.

Example 4. The endoscope according to Example 3, wherein the center axis of the operation knob is disposed to be inclined by not less than 5 degrees and less than 10 degrees with respect to the direction that is perpendicular to each of the longitudinal direction and the advancing and retreating direction of the switch button.

Example 5. The endoscope according to Example 1, wherein the operation knob is configured to include at least a first operation knob and a second operation knob from a side close to the operation section main body along the center axis of the operation knob, a distance between a line that passes through a switch button end surface and is parallel to the advancing and retreating direction of the switch button and an end surface of the first operation knob is longer on a side where the switch button is not provided than on a side where the switch button is provided in a view in the longitudinal direction, and a distance between the line that passes through the switch button end surface and is parallel to the direction in which the switch button advances and retreats and an end surface of the second operation knob is longer on the side where the switch button is not provided than on the side where the switch button is provided in a view in the longitudinal direction.

Example 6. The endoscope according to Example 1, wherein the center axis of the operation knob is disposed to be further inclined toward a side where the insertion section is provided in a view in the direction that is perpendicular to each of the longitudinal direction and the direction in which the switch button advances and retreats.

Example 7. The endoscope according to Example 1, wherein an end surface of the switch button is provided with a tapered surface that is inclined with respect to the direction in which the switch advances and retreats in a view in the longitudinal direction.

Example 8. The endoscope according to Example 7, wherein an outline of a taper of the end surface of the switch button is parallel to the center axis of the operation knob in a view in the longitudinal direction.

Example 9. The endoscope according to Example 2, wherein a part of a component configuring the switch button is hidden by an end surface of the operation knob in a view in the direction in which the switch button advances and retreats.

Example 10. The endoscope according to Example 1, wherein a bending section that is bent in a direction intersecting the longitudinal direction is provided on the side of the distal end of the insertion section, the operation section main body is provided with a pulley around which a long member that pulls the bending section and causes the bending section to be bent through an operation of the operation knob is wound, and a rotation shaft of the pulley is set to be parallel to or coaxial with the center axis of the operation knob.

Example 11. The endoscope according to Example 1, wherein a bending section that is bent in a direction intersecting the longitudinal direction is provided on the side of the distal end of the insertion section, the operation section main body is provided with a pulley around which a long member that pulls the bending section and causes the bending section to be bent through an operation of the operation knob is wound; a rotation shaft of the pulley is set to be parallel to a direction perpendicular to each of the longitudinal direction and the direction in which the switch button advances and retreats, and a universal joint is provided between a shaft member that is provided along the center axis of the operation knob and transmits a force of the operation knob to the pulley and the pulley.

Example 12. The endoscope according to Example 1, wherein the operation knob includes at least a first operation knob and a second operation knob from a side close to the operation section main body along the center axis of the operation knob, a bending section that is bent in a direction intersecting the longitudinal direction is provided on the side of the distal end of the insertion section, and the operation section main body is provided with pulleys around which a long member that pulls the bending section and causes the bending section to be bent through an operation of the operation knob is wound, and as the pulleys, at least a first pulley that establishes connection to the first operation knob and a second pulley that establishes connection to the second operation knob are provided.

Example 13. The endoscope according to Example 1, wherein the switch button is an air feeding or water feeding button that performs an operation of giving and receiving a fluid between the operation section and the distal end of the insertion section.

Example 14. The endoscope according to Example 1, wherein the endoscope is a gastrointestinal endoscope that is used for a gastrointestinal system.

Example 15. The endoscope according to Example 1, wherein the endoscope is a single-use endoscope that is discarded after a single use.

Example 16. An endoscope comprising:
an insertion section that is inserted into a subject from a side of a distal end;
an operation section main body that is provided continuously from a side of a proximal end of the insertion section and is grasped by a user;
an operation knob that is disposed in the operation section main body and performs an operation of moving the side of the distal end of the insertion section; and
a switch button that is provided in the operation section main body and performs advancing and retreating motions to perform other operations of the insertion section,
wherein a center axis of the operation knob is disposed to be inclined with respect to a direction that is perpendicular to each of a longitudinal direction and an advancing and retreating direction of the switch button in a view in the longitudinal direction.

Example 17. An operation section for an endoscope comprising:
an operation section main body that is grasped by a user to perform an operation;
a connection member to an insertion section that includes a site operating in response to the operation of the user and is inserted into a subject from a side of a distal end;
an operation knob that is disposed in the operation section main body to perform an operation of moving the side of the distal end of the insertion section; and
a switch button that is provided in the operation section main body and performs advancing and retreating motions to perform operations of other functions of the insertion section,
wherein a center axis of the operation knob is disposed to be inclined to form an acute angle with respect to a direction perpendicularly intersecting a longitudinal direction and a direction perpendicularly intersecting an advancing and retreating direction of the switch button in a view in the longitudinal direction.

What is claimed is:
1. An endoscope, comprising:
an insertion section including a distal end and a proximal end, the insertion section configured for insertion into a subject; and
an operation section main body connected to the proximal end of the insertion section, the operation section main body configured to be grasped by a user,
wherein the operation section main body includes an operation knob and a switch button,
wherein the operation knob is rotatable about a center axis relative to the operation section main body to move the distal end of the insertion section,
wherein the switch button is translatable in a translating direction relative to the operation section main body, and
wherein, in a view in a longitudinal direction of the operation section main body, the center axis is configured to be tilted with respect to a direction that is perpendicular to each of the longitudinal direction of the operation section main body and the translating direction of the switch button.

2. The endoscope according to claim 1, wherein the center axis of the operation knob is configured to be tilted such that the operation knob is tilted toward a side of the operation section main body where the switch button is located.

3. The endoscope according to claim 2, wherein the operation knob is configured to be tilted to form an acute angle that is not less than 1 degree and is not more than 30 degrees.

4. The endoscope according to claim 3, wherein the acute angle is not less than 5 degrees and is less than 10 degrees.

5. The endoscope according to claim 1, wherein the operation knob includes a first operation knob and a second operation knob, the first operation knob and the second operation knob are arranged along the center axis of the operation knob with the first operation knob closer to the operation section main body than the second operation knob, wherein an imaginary line that passes through an end surface of the switch button and that is parallel to the translating direction of the switch button defines a first line, and wherein, in the view in the longitudinal direction of the operation section main body, a shortest distance between the first line and an end surface of the first operation knob is longer on a first side of the center axis of the operation knob where the switch button is not provided than on a second side of the center axis of the operation knob where the switch button is provided.

6. The endoscope according to claim 1, wherein, in a view in a direction that is perpendicular to each of the longitudinal direction of the operation section main body and the translating direction of the switch button, the center axis of the operation knob is configured to be tilted toward a location on the operation section main body where the insertion section is connected.

7. The endoscope according to claim 1, wherein, in a view in the longitudinal direction of the operation section main body, an end surface of the switch button includes a tapered surface that is inclined with respect to the translating direction of the switch button.

8. The endoscope according to claim 1, wherein the insertion section includes a bending section connecting a distal end section to a flexible tube section, wherein the bending section that is configured to bend in a direction that intersects the longitudinal direction of the operation section main body, wherein the operation section main body further includes a pulley around which a wire is wound, and wherein a rotation shaft of the pulley is parallel to or coaxial with the center axis of the operation knob.

9. The endoscope according to claim 8, further comprising a wire tension mechanism configured to apply a predetermined tension to the wire.

10. The endoscope according to claim 1, wherein the insertion section includes a bending section connecting a distal end section to a flexible tube section, wherein the bending section that is configured to bend in a direction that intersects the longitudinal direction of the operation section main body, wherein the operation section main body further includes a pulley around which a wire is wound, wherein a rotation shaft of the pulley is parallel to a direction perpendicular to each of the longitudinal direction of the operation section main body and the translating direction of the switch button, wherein a shaft member is located along the center axis of the operation knob, wherein a universal joint is provided between the shaft member and the pulley, and wherein the universal joint is configured to transmit a force from rotation of the operation knob to the pulley.

11. The endoscope according to claim 1, wherein the operation knob includes a first operation knob and a second operation knob, the first operation knob and the second operation knob are arranged along the center axis of the operation knob with the first operation knob closer to the operation section main body than the second operation knob, wherein the insertion section includes a bending section connecting a distal end section to a flexible tube section, wherein the bending section that is configured to bend in a direction that intersects the longitudinal direction of the operation section main body, wherein the operation section main body further includes a plurality of pulleys and around each pulley of the plurality of pulleys a wire is wound, wherein a first pulley of the plurality of pulleys is connected to the first operation knob and a second pulley of the plurality of pulleys is connected to the second operation knob, wherein the first operation knob is configured such that rotation of the first operation knob bends the bending section in a first direction, and wherein the second operation knob is configured such that rotation of the second operation knob bends the bending section in a second direction, the second direction different from the first direction.

12. The endoscope according to claim 1, wherein the endoscope is a single-use endoscope.

13. The endoscope according to claim 1, further comprising an angle fixing mechanism configured to fix the operation knob at a predetermined angle.

14. The endoscope according to claim 1, further comprising a sleeve member disposed a space between the operation section main body and the operation knob.

15. The endoscope according to claim 1, wherein the operation knob includes a protruding portion protruding along the center axis of the operation knob.

16. The endoscope according to claim 1, further comprising a lever provided between the operation knob and the operation section main body, the lever configured to operate the insertion section.

17. The endoscope according to claim 1, wherein the operation section main body further includes a pulley around which a wire is wound, and wherein the center axis of the operation knob is configured to be tilted with respect to a center axis of the pulley.

18. The endoscope according to claim 1, wherein the center axis of the operation knob is configured to be changed a tilted angle between a first angle and a second angle with respect to at least one of the longitudinal direction of the operation section main body and the translating direction of the switch button.

19. An operation section for an endoscope, comprising:

an operation section main body configured to be grasped by a user, wherein the operation section main body includes an operation knob and a switch button, wherein the operation knob is rotatable about a center axis relative to the operation section main body, wherein the switch button is translatable in a translating direction relative to the operation section main body, and wherein, in a view in a longitudinal direction of the operation section main body, the center axis is configured to be tilted with respect to a direction that is perpendicular to each of the longitudinal direction of the operation section main body and the translating direction of the switch button.

20. The operation section according to claim 19, further comprising:

a connection member configured to connect a distal end of the operation section main body to a proximal end of an insertion section having a distal end configured for insertion into a subject, wherein the operation knob is configured such that rotation of the operation knob about the center axis moves the distal end of the insertion section, and wherein the switch button is configured such that translation of the switch button in the translating direction executes an operation of the endoscope.

* * * * *